United States Patent
Ogita et al.

(10) Patent No.: US 10,347,847 B2
(45) Date of Patent: Jul. 9, 2019

(54) ORGANIC COMPOUND, LIGHT-EMITTING ELEMENT, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Kaori Ogita, Kanagawa (JP); Satoshi Seo, Kanagawa (JP); Hiromi Seo, Kanagawa (JP); Tatsuyoshi Takahashi, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 15/494,988

(22) Filed: Apr. 24, 2017

(65) Prior Publication Data
US 2017/0256724 A1     Sep. 7, 2017

Related U.S. Application Data

(63) Continuation of application No. 14/223,548, filed on Mar. 24, 2014, now Pat. No. 9,634,263.

(51) Int. Cl.
*H01L 51/50* (2006.01)
*H01L 51/00* (2006.01)

(52) U.S. Cl.
CPC ........ *H01L 51/0074* (2013.01); *H01L 51/006* (2013.01); *H01L 51/0061* (2013.01);
(Continued)

(58) Field of Classification Search
None
See application file for complete search history.

(56) References Cited

U.S. PATENT DOCUMENTS

| 5,510,218 A | 4/1996 | Nakata et al. |
| 8,736,157 B2 | 5/2014 | Seo et al. |

(Continued)

FOREIGN PATENT DOCUMENTS

| CN | 102190653 A | 9/2011 |
| CN | 102482215 A | 5/2012 |

(Continued)

OTHER PUBLICATIONS

Kondakova, M.E. et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.

(Continued)

Primary Examiner — Gregory D Clark
(74) Attorney, Agent, or Firm — Fish & Richardson P.C.

(57) ABSTRACT

A novel organic compound that forms an exciplex emitting light with high efficiency is provided. An organic compound with a triarylamine skeleton in which the three aryl groups of the triarylamine skeleton are a p-biphenyl group, a fluoren-2-yl group, and a phenyl group to which a dibenzofuranyl group or a dibenzothiophenyl group is bonded. By the use of the organic compound and an organic compound with an electron-transport property, an exciplex that emits light with extremely high efficiency can be formed.

16 Claims, 35 Drawing Sheets

(52) U.S. Cl.
CPC ...... *H01L 51/0072* (2013.01); *H01L 51/0073* (2013.01); *H01L 51/5016* (2013.01)

(56) References Cited

U.S. PATENT DOCUMENTS

| | | | |
|---|---|---|---|
| 8,847,367 B2 | 9/2014 | Fukumatsu et al. | |
| 8,853,680 B2 | 10/2014 | Yamazaki et al. | |
| 9,123,907 B2 | 9/2015 | Seo et al. | |
| 9,175,213 B2 | 11/2015 | Seo et al. | |
| 9,200,022 B2 | 12/2015 | Inoue et al. | |
| 9,269,920 B2 | 2/2016 | Yamazaki et al. | |
| 9,595,681 B2 | 3/2017 | Mujica-Fernaud et al. | |
| 9,604,928 B2 | 3/2017 | Shitagaki et al. | |
| 9,634,279 B2 | 4/2017 | Seo et al. | |
| 10,014,477 B2 | 7/2018 | Kato et al. | |
| 2002/0074935 A1 | 6/2002 | Kwong et al. | |
| 2004/0164292 A1 | 8/2004 | Tung et al. | |
| 2004/0219386 A1 | 11/2004 | Thoms | |
| 2005/0221124 A1 | 10/2005 | Hwang et al. | |
| 2007/0215867 A1 | 9/2007 | Kawakami et al. | |
| 2007/0215889 A1 | 9/2007 | Kawakami et al. | |
| 2008/0124572 A1 | 5/2008 | Mizuki et al. | |
| 2009/0160323 A1 | 6/2009 | Nomura et al. | |
| 2010/0230666 A1 | 9/2010 | Ohuchi et al. | |
| 2012/0146014 A1* | 6/2012 | Kato ............... | C07D 209/86 257/40 |
| 2012/0205632 A1 | 8/2012 | Shitagaki et al. | |
| 2012/0205687 A1 | 8/2012 | Yamazaki et al. | |
| 2014/0034929 A1 | 2/2014 | Hamada et al. | |
| 2014/0284578 A1 | 9/2014 | Takeda et al. | |
| 2017/0179411 A1 | 6/2017 | Shitagaki et al. | |
| 2017/0279063 A1 | 9/2017 | Seo et al. | |
| 2018/0123043 A1 | 5/2018 | Kato et al. | |
| 2018/0269410 A1 | 9/2018 | Shitagaki et al. | |

FOREIGN PATENT DOCUMENTS

| | | | |
|---|---|---|---|
| EP | 2 276 085 A1 | 1/2011 | |
| EP | 2 363 398 A1 | 9/2011 | |
| EP | 2 366 753 A1 | 9/2011 | |
| EP | 2 468 725 A1 | 6/2012 | |
| EP | 2891648 A | 7/2015 | |
| JP | 11-144875 A | 5/1999 | |
| JP | 11-184109 A | 7/1999 | |
| JP | 11-184119 A | 7/1999 | |
| JP | 2004-515895 | 5/2004 | |
| JP | 2006-278651 A | 10/2006 | |
| JP | 2011-201869 A | 10/2011 | |
| JP | 2011-204673 A | 10/2011 | |
| JP | 2012-186461 A | 9/2012 | |
| JP | 2012-212879 A | 11/2012 | |
| JP | 2012-216829 A | 11/2012 | |
| JP | 2012-227524 A | 11/2012 | |
| JP | 2012-231137 A | 11/2012 | |
| JP | 2013-539205 | 10/2013 | |
| JP | 2015-529970 | 10/2015 | |
| KR | 2010-0003632 A | 1/2010 | |
| KR | 2010-0007639 A | 1/2010 | |
| KR | 10-1029082 | 4/2011 | |
| KR | 2011-0099173 A | 9/2011 | |
| KR | 2011-0099645 A | 9/2011 | |
| KR | 2012-0011445 A | 2/2012 | |
| KR | 2012-0052993 A | 5/2012 | |
| KR | 2015-0036721 A | 4/2015 | |
| KR | 2015-0048137 A | 5/2015 | |
| WO | WO 2009/119249 A1 | 10/2009 | |
| WO | WO 2011/021520 A1 | 2/2011 | |
| WO | WO 2012/015265 A1 * | 2/2012 | ........... C07D 333/76 |
| WO | WO 2012/091471 A2 | 7/2012 | |
| WO | WO-2012/111579 | 8/2012 | |
| WO | WO-2012/127990 | 9/2012 | |
| WO | WO-2012/132809 | 10/2012 | |
| WO | WO-2012/137693 | 10/2012 | |
| WO | WO-2012/141185 | 10/2012 | |
| WO | WO 2012/177006 A2 | 12/2012 | |
| WO | WO 2013/002514 A2 | 1/2013 | |
| WO | WO 2013/032304 A2 | 3/2013 | |
| WO | WO 2013/118812 A1 | 8/2013 | |
| WO | WO 2014/015937 A1 | 1/2014 | |
| WO | WO 2014/034795 A1 | 3/2014 | |

OTHER PUBLICATIONS

Seo, J.H. et al., "Efficient Blue-Green Organic Light-Emitting Diodes Based on Heteroleptic tris-cyclometalated Iridium(III) Complexes," Thin Solid Films, Sep. 25, 2008, vol. 517, No. 5, pp. 1807-1810.

Goushi, K et al., "Efficient Organic Light-Emitting Diodes Through Up-Conversion from Triplet to Singlet Excited States of Exciplexes," Applied Physics Letters, Jul. 12, 2012, vol. 101, No. 2, pp. 023306-1-023306-4.

International Search Report re Application No. PCT/JP2014/057944, dated Apr. 28, 2014.

Written Opinion re Application No. PCT/JP2014/057944, dated Apr. 28, 2014.

* cited by examiner

ORGANIC COMPOUND, LIGHT-EMITTING ELEMENT, LIGHT-EMITTING DEVICE, DISPLAY DEVICE, ELECTRONIC DEVICE, AND LIGHTING DEVICE

This application is a continuation of copending U.S. application Ser. No. 14/223,548, filed on Mar. 24, 2014 which is incorporated herein by reference.

TECHNICAL FIELD

The present invention relates to a light-emitting element, a display device, a light-emitting device, an electronic device, and a lighting device each of which includes an organic compound as a light-emitting substance.

BACKGROUND ART

Advances are being made in application of a current excitation type light-emitting element in which an organic compound is used as a light-emitting substance, i.e., an organic EL element, to light sources, lighting, displays, and the like.

As is known, in an organic EL element, the generation ratio of excitons in a singlet excited state to excitons in a triplet excited state is 1:3. Thus, the limit value of internal quantum efficiency of fluorescence, which is emitted by conversion of a singlet excited state into light emission, is 25%, while phosphorescence, which is emitted by conversion of a triplet excited state into light emission, can have an internal quantum efficiency of 100% when energy transfer via intersystem crossing from a singlet excited state is taken into account. In view of the above, an organic EL element (also referred to as a phosphorescent light-emitting element) in which a phosphorescent material is used as a light-emitting substance is selected in many cases so that light is emitted efficiently.

To cause conversion of a triplet excited state into light emission, delayed fluorescence can also be utilized. In this case, not phosphorescence but fluorescence is obtained because reverse intersystem crossing from a triplet excited state to a singlet excited state is utilized and the light emission occurs from a singlet excited state. This is readily caused when an energy difference between a singlet excited state and a triplet excited state is small. Emission efficiency exceeding the theoretical limit of emission efficiency of fluorescence has been actually reported.

It has also been reported that an exciplex (excited complex) formed by two kinds of substances was utilized to achieve a state where an energy difference between a singlet excited state and a triplet excited state is small, whereby a high-efficiency light-emitting element was provided.

REFERENCE

Non-Patent Document

[Non-Patent Document 1] K. Goushi et al., *Applied Physics Letters*, 101, pp. 023306/1-023306/4 (2012).

DISCLOSURE OF INVENTION

However, in such a light-emitting element utilizing an exciplex, use of certain substances often prevents efficient light emission. Actually, in the history of development of organic EL elements, an exciplex has been considered to decrease efficiency and organic EL elements have been generally designed such that an exciplex is not formed.

Against this backdrop, structures for forming exciplexes that efficiently emit light have hardly been determined.

In view of the above, an object of one embodiment of the present invention is to provide a novel organic compound which forms an exciplex that efficiently emits light. Another object of one embodiment of the present invention is to provide a light-emitting element which has high emission efficiency. A further object of one embodiment of the present invention is to provide a light-emitting element which utilizes an exciplex and has high efficiency. A still further object of one embodiment of the present invention is to provide a light-emitting element which emits light from an exciplex and has high efficiency.

A yet still further object of one embodiment of the present invention is to provide a light-emitting device, a display device, an electronic device, and a lighting device each of which has high emission efficiency by using any of the above light-emitting elements.

It is only necessary that at least one of the above-described objects be achieved in the present invention.

One embodiment of the present invention for achieving any of the above objects is an organic compound with a triarylamine skeleton in which the three aryl groups of the triarylamine skeleton are a p-biphenyl group, a fluoren-2-yl group, and a phenyl group to which a dibenzofuranyl group or a dibenzothiophenyl group is bonded.

Another embodiment of the present invention is an organic compound represented by General Formula (G1).

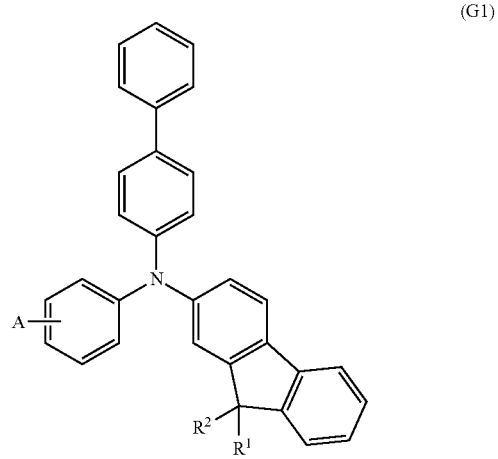

(G1)

In the formula, A represents any one of a dibenzofuranyl group and a dibenzothiophenyl group, $R^1$ and $R^2$ separately represent any one of hydrogen, an alkyl group having 1 to 6 carbon atoms, and a phenyl group. Note that when both $R^1$ and $R^2$ are phenyl groups, the phenyl groups may be bonded to each other to form a spirofluorene skeleton.

A further embodiment of the present invention is an organic compound represented by General Formula (G2).

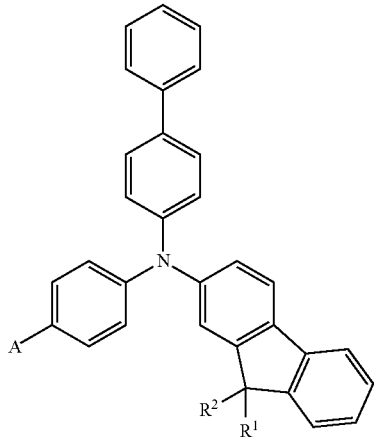
(G2)

In the formula, A represents any one of a dibenzofuranyl group and a dibenzothiophenyl group, $R^1$ and $R^2$ separately represent any one of hydrogen, an alkyl group having 1 to 6 carbon atoms, and a phenyl group. Note that when both $R^1$ and $R^2$ are phenyl groups, the phenyl groups may be bonded to each other to form a spirofluorene skeleton.

A still further embodiment of the present invention is an organic compound where the group represented by A in any of the above structures is any one of groups represented by Structural Formulae (A-1) to (A-4).

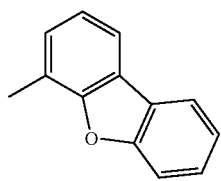
(A-1)

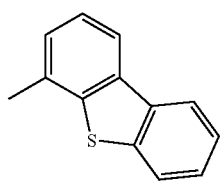
(A-2)

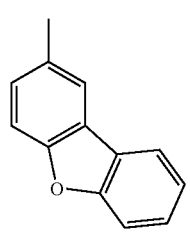
(A-3)

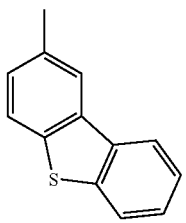
(A-4)

A yet still further embodiment of the present invention is an organic compound where the group represented by A in any of the above structures is a group represented by Structural Formula (A-1) or (A-2).

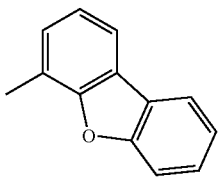
(A-1)

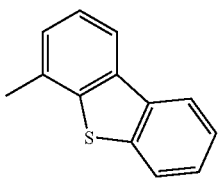
(A-2)

A yet still further embodiment of the present invention is an organic compound where the group represented by A in any of the above structures is a group represented by Structural Formula (A-1).

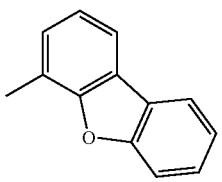
(A-1)

A yet still further embodiment of the present invention is an organic compound where $R^1$ and $R^2$ in any of the above structures separately represent any one of groups represented by Structural Formulae (R-1) to (R-12).

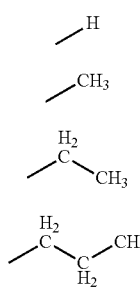

(R-1)
(R-2)
(R-3)
(R-4)

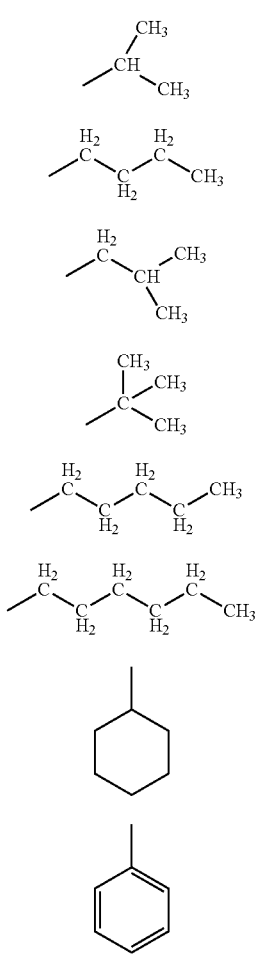

(R-5)

(R-6)

(R-7)

(R-8)

(R-9)

(R-10)

(R-11)

(R-12)

A yet still further embodiment of the present invention is an organic compound where both R¹ and R² in any of the above structures are methyl groups.

A yet still further embodiment of the present invention is an organic compound represented by Structural Formula (100).

(100)

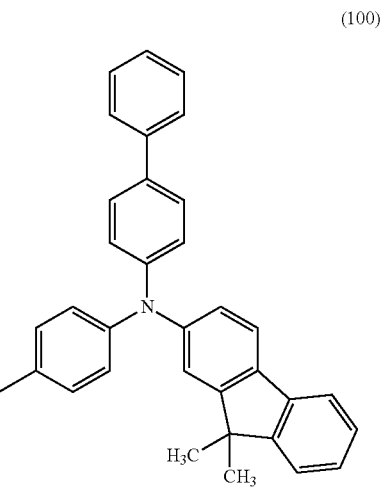

A yet still further embodiment of the present invention is a light-emitting element that includes a pair of electrodes and a layer containing an organic compound between the pair of electrodes. The layer containing the organic compound contains any of the above organic compounds.

A yet still further embodiment of the present invention is a light-emitting element that includes a pair of electrodes and a layer containing an organic compound between the pair of electrodes. The layer containing the organic compound includes at least a light-emitting layer. The light-emitting layer contains any of the above organic compounds.

A yet still further embodiment of the present invention is a light-emitting element that includes a pair of electrodes and a layer containing an organic compound between the pair of electrodes. The layer containing the organic compound includes at least a light-emitting layer. The light-emitting layer contains at least a first organic compound and a second organic compound. The first organic compound has an electron-transport property. The second organic compound is any of the above organic compounds.

A yet still further embodiment of the present invention is a light-emitting element that includes a pair of electrodes and a layer containing an organic compound between the pair of electrodes. The layer containing the organic compound includes at least a light-emitting layer. The light-emitting layer contains at least a first organic compound, a second organic compound, and a phosphorescent substance. The first organic compound has an electron-transport property. The second organic compound is any of the above organic compounds.

A yet still further embodiment of the present invention is a light-emitting element with any of the above structures, in which the first organic compound and the second organic compound form an exciplex.

A yet still further embodiment of the present invention is a light-emitting element with the above structure, in which triplet excitation energy of each of the first organic compound and the second organic compound is higher than energy equivalent to a wavelength of light emitted by the exciplex formed by the first organic compound and the second organic compound (in other words, light energy of light emitted by the exciplex formed by the first organic compound and the second organic compound).

A yet still further embodiment of the present invention is a lighting device which includes a light-emitting element having any of the above-described structures.

A yet still further embodiment of the present invention is a light-emitting device which includes a light-emitting element having any of the above-described structures and a unit which controls the light-emitting element.

A yet still further embodiment of the present invention is a display device which includes a light-emitting element having any of the above-described structures in a display portion and a unit which controls the light-emitting element.

A yet still further embodiment of the present invention is an electronic device which includes a light-emitting element having any of the above-described structures.

Note that the light-emitting device in this specification includes, in its category, an image display device using a light-emitting element. Further, the category of the light-emitting device in this specification includes a module in which a light-emitting element is provided with a connector such as an anisotropic conductive film or a tape carrier package (TCP); a module having a TCP at the tip of which a printed wiring board is provided; and a module in which an IC (integrated circuit) is directly mounted on a light-emitting element by a COG (chip on glass) method. Furthermore, the category includes a light-emitting device which is used in lighting equipment or the like.

In one embodiment of the present invention, a novel organic compound which forms an exciplex that efficiently emits light can be provided. In one embodiment of the present invention, a light-emitting element which has high emission efficiency can be provided. In one embodiment of the present invention, a light-emitting element which utilizes an exciplex and has high efficiency can be provided. In one embodiment of the present invention, a light-emitting element which emits light from an exciplex and has high efficiency can be provided. In one embodiment of the present invention, a phosphorescent light-emitting element which emits light via energy transfer from an exciplex and has high efficiency can be provided.

In one embodiment of the present invention, a light-emitting device, a display device, an electronic device, and a lighting device each having high emission efficiency can be provided.

BRIEF DESCRIPTION OF DRAWINGS

FIGS. 7A, 7B 1, 7B2, 7C, and 7D illustrate electronic devices.

BEST MODE FOR CARRYING OUT THE INVENTION

Figure 1A:
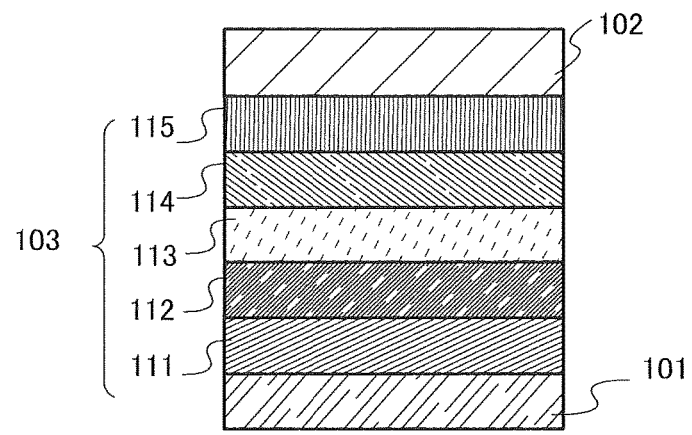
FIGS. 1A and 1B are conceptual diagrams of light-emitting elements.

Embodiments of the present invention will be explained below with reference to the drawings. Note that the present invention is not limited to the description below, and it is easily understood by those skilled in the art that various changes and modifications can be made without departing from the spirit and scope of the present invention. Accordingly, the present invention should not be interpreted as being limited to the content of the embodiments below.

Embodiment 1

As one embodiment of the present invention for achieving any of the above objects, a novel organic compound with a triarylamine skeleton in which the three aryl groups of the triarylamine skeleton are a p-biphenyl group, a fluoren-2-yl group, and a phenyl group to which a dibenzofuranyl group or a dibenzothiophenyl group is bonded will be described in this embodiment.

Three aryl groups are bonded to nitrogen of a triarylamine skeleton. In an organic compound in this embodiment, the three aryl groups are a p-biphenyl group, a fluoren-2-yl group, and a phenyl group to which a dibenzofuranyl group or a dibenzothiophenyl group is bonded.

The carbon at the 9-position of the fluoren-2-yl group may have one or two substituents, which are separately any one of an alkyl group having 1 to 6 carbon atoms and a phenyl group. When both of the substituents are phenyl groups, the phenyl groups may be bonded to each other to form a spirofluorene skeleton.

Further, the dibenzofuranyl group or the dibenzothiophenyl group may be bonded to the ortho-position, the meta-position, or the para-position of the phenyl group but is preferably bonded to the para-position in terms of reliability. The dibenzofuranyl group or the dibenzothiophenyl group is preferably bonded to the phenyl group at the 4-position or the 2-position of the dibenzofuranyl group or the dibenzothiophenyl group in terms of synthesis, and the dibenzofuranyl group or the dibenzothiophenyl group is further preferably bonded to the phenyl group at the 4-position of the dibenzofuranyl group or the dibenzothiophenyl group.

Note that in the organic compound described in this embodiment, each of the p-biphenyl group and the fluoren-2-yl group, which are the aryl groups bonded to nitrogen of the amine, has a biphenyl skeleton and does not have a terphenyl skeleton. The fluorene skeleton can be regarded as a bridged biphenyl skeleton.

Here, if the biphenyl skeleton is replaced with a terphenyl group or a group including three or more benzene skeletons, the triplet excitation level is lowered, which inhibits efficient light emission from an exciplex. Further, if a phenyl group is bonded as a substituent to a position other than the 9-position of the fluoren-2-yl group, a terphenyl skeleton is formed, which is also problematic. Note that a p-biphenyl group and a fluoren-2-yl group are preferable as substituents in terms of reliability.

The other aryl group bonded to nitrogen of the amine, i.e., the phenyl group to which a dibenzofuranyl group or a dibenzothiophenyl group is bonded, also plays an important role. If the phenyl group is replaced with a group having more benzene skeletons than a phenyl group, e.g., a biphenyl group, the biphenyl group and one of the benzene rings of the dibenzofuranyl group or the dibenzothiophenyl group form a terphenyl skeleton, which also inhibits efficient light emission from an exciplex.

The above-described organic compound can be more specifically represented by General Formula (G1).

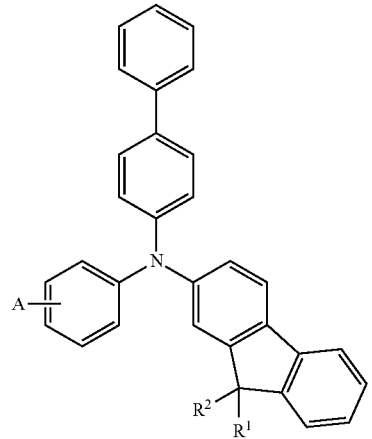

(G1)

In General Formula (G1), the phenylene group to which the group represented by A is bonded is preferably a p-phenylene group. In other words, a structure represented by General Formula (G2) is preferable.

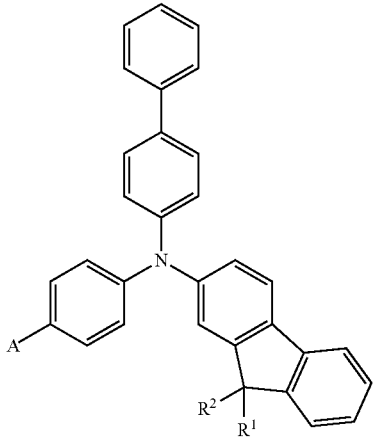

(G2)

In General Formula (G1) or (G2), A represents any one of a dibenzofuranyl group and a dibenzothiophenyl group.

The dibenzofuranyl group or the dibenzothiophenyl group is preferably any one of groups represented by Structural Formulae (A-1) to (A-4), and further preferably a group represented by Structural Formula (A-1) or (A-2).

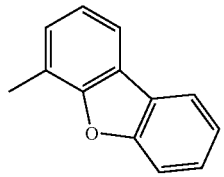

(A-1)

(A-2)
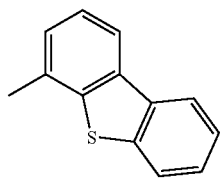

(A-3)
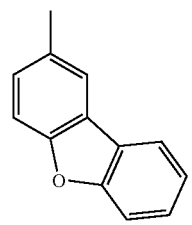

(A-4)
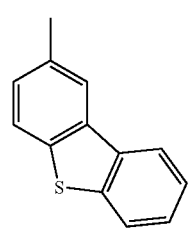

$R^1$ and $R^2$ separately represent any one of hydrogen, an alkyl group having 1 to 6 carbon atoms, and a phenyl group. When both $R^1$ and $R^2$ are phenyl groups, the phenyl groups may be bonded to each other to form a spirofluorene skeleton. Specific examples of $R^1$ and $R^2$ include groups represented by Structural Formulae (R-1) to (R-12).

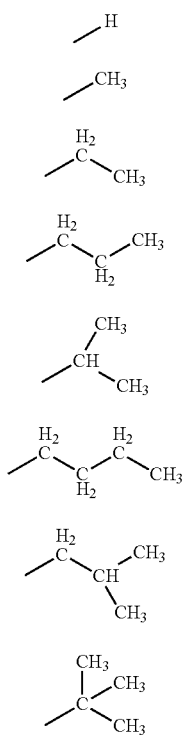

(R-1)
(R-2)
(R-3)
(R-4)
(R-5)
(R-6)
(R-7)
(R-8)

(R-9)
(R-10)
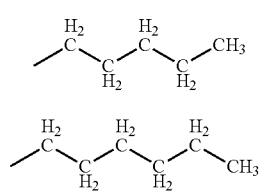

(R-11)
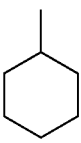

(R-12)
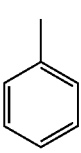

Specific examples of an organic compound having the above structure are represented by Structural Formulae (100) to (109) and (200) to (209). Note that an organic compound of one embodiment of the present invention is not limited to the examples below.

(100)
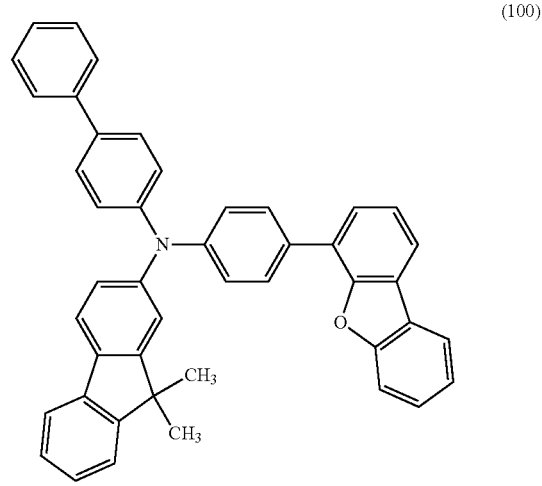

(101)
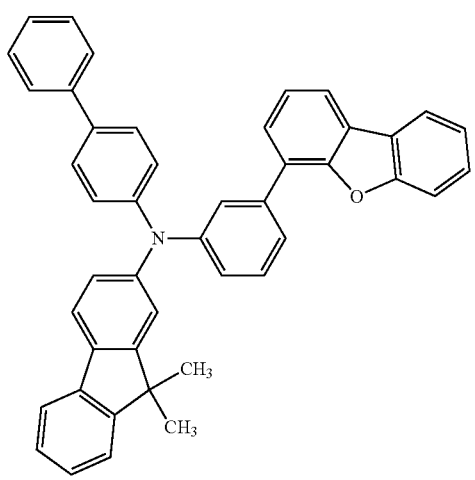

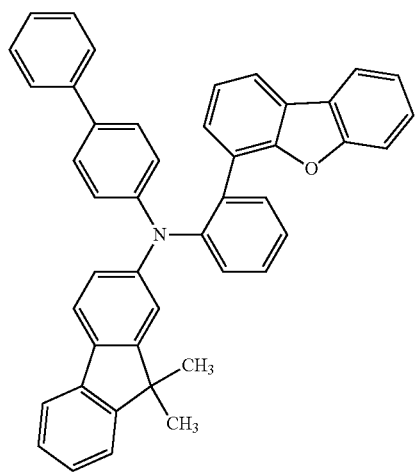
(102)
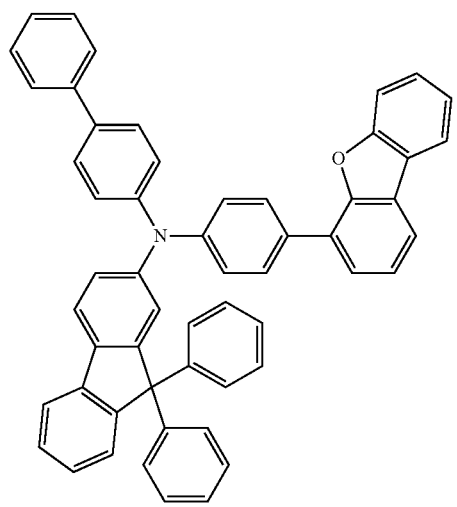
(105)
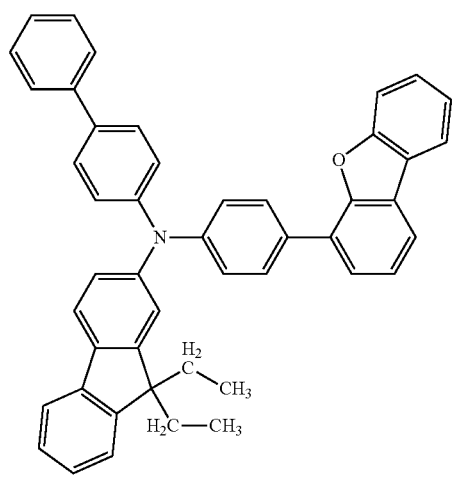
(103)
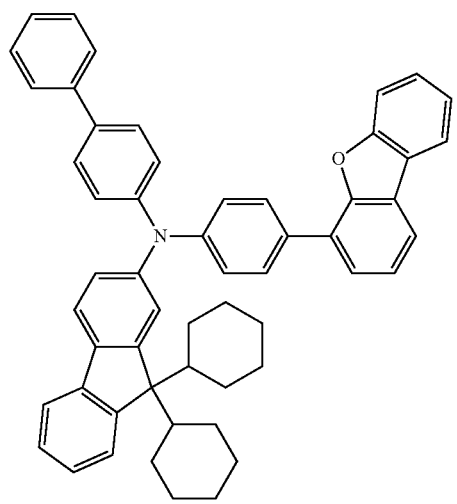
(106)
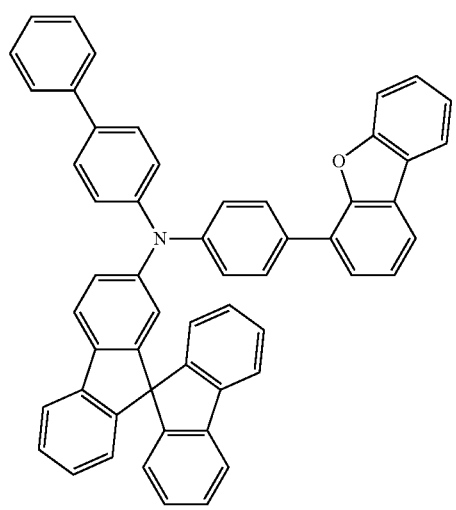
(104)
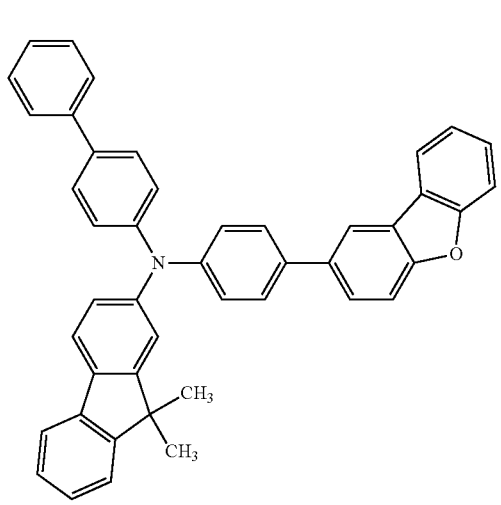
(107)

(108)
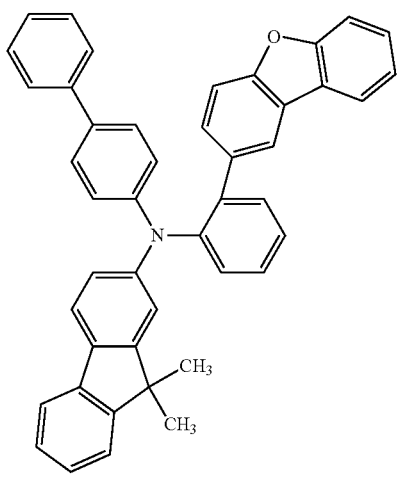
(109)
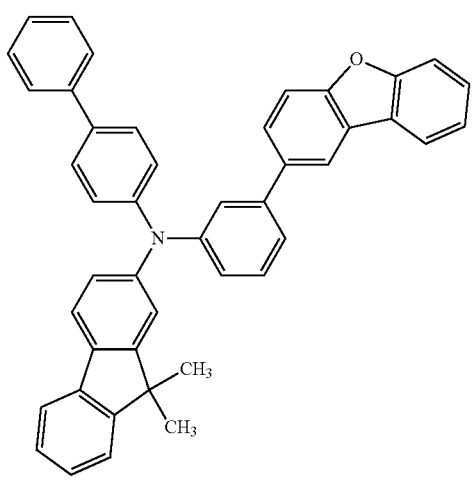
(110)
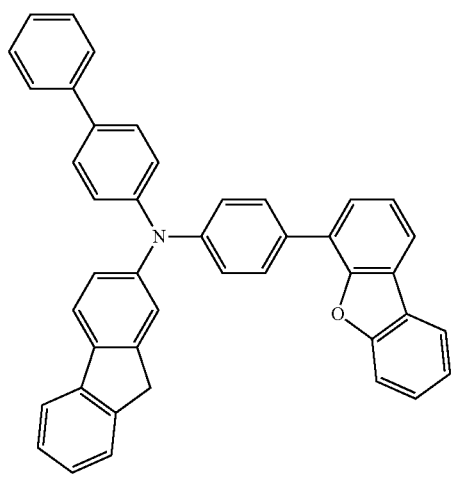
(200)
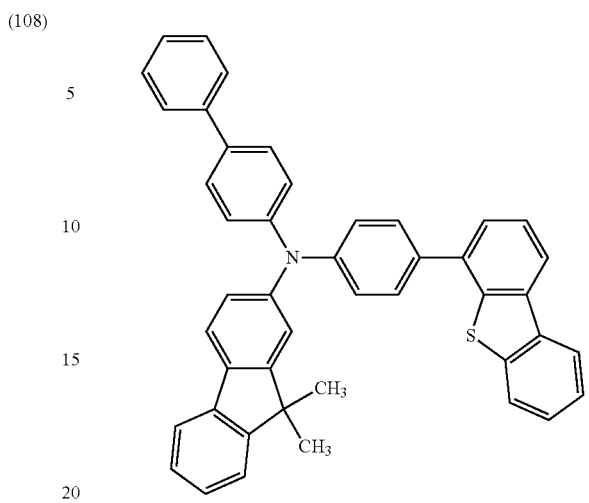
(201)
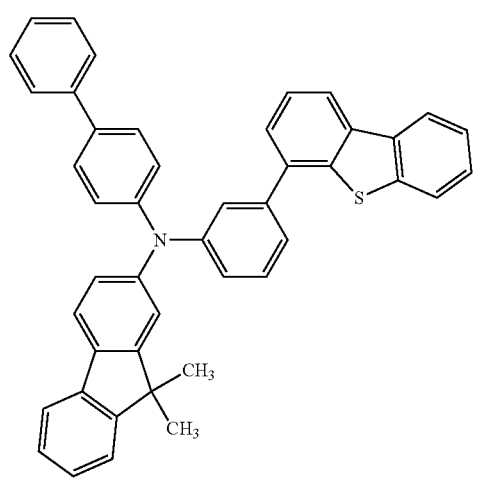
(202)
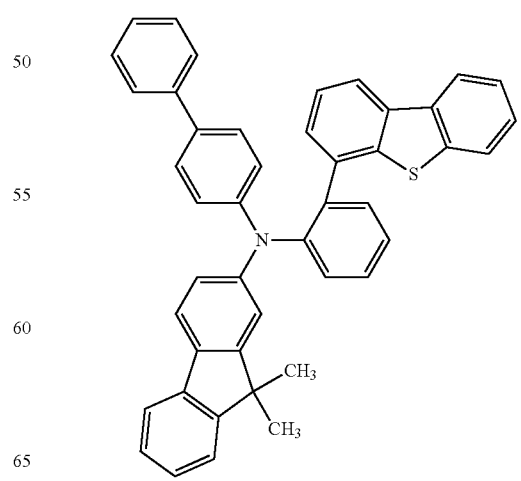

(203)
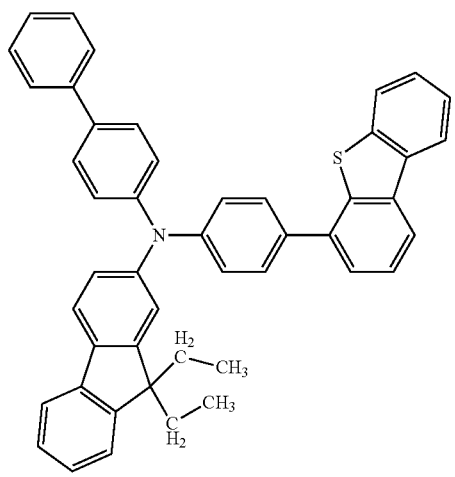
(206)
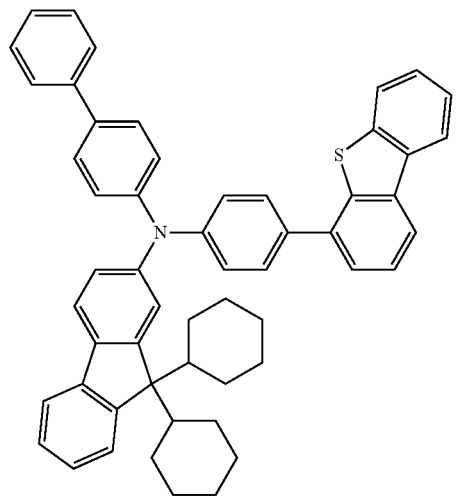
(204)
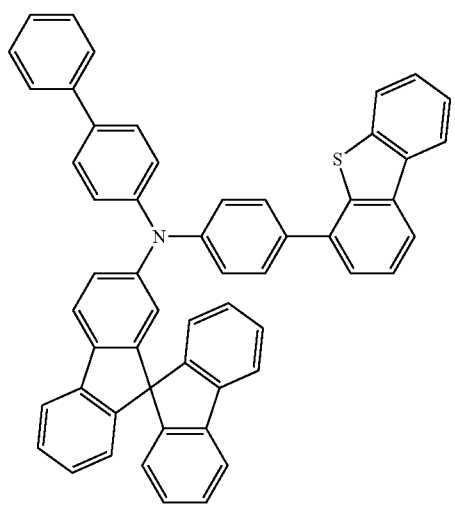
(207)
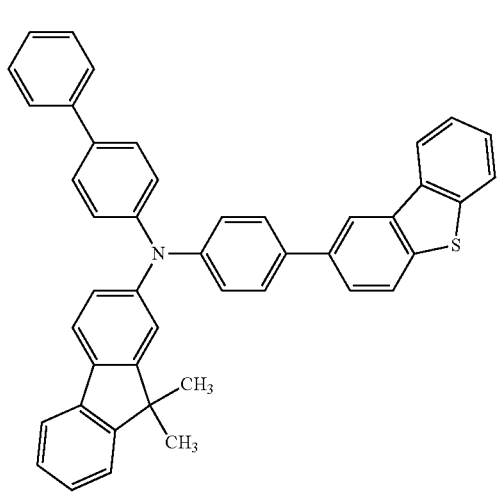
(205)
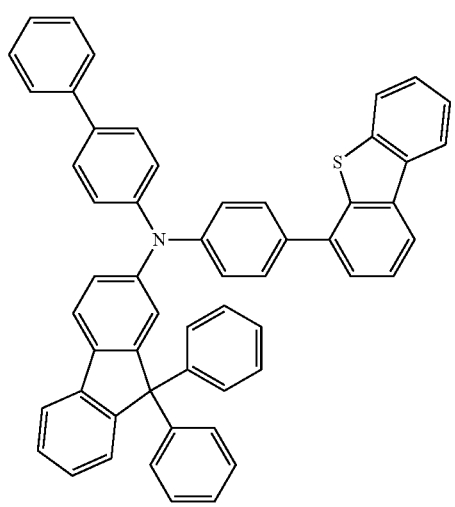
(208)
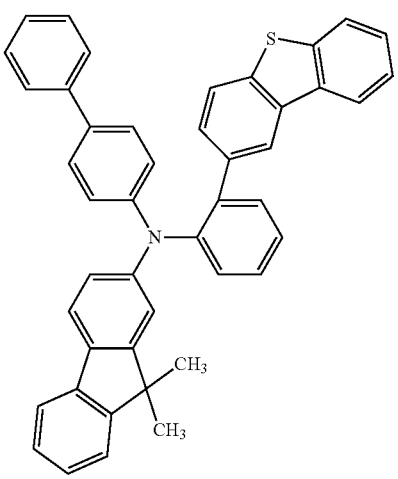

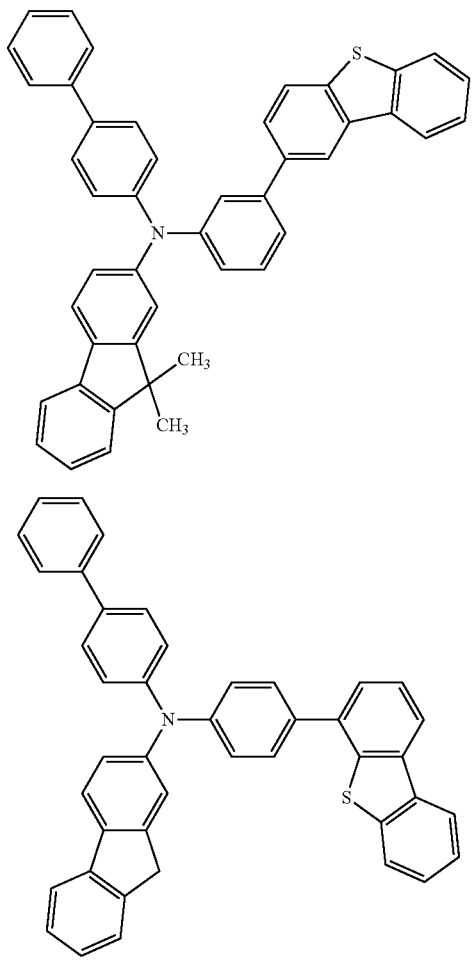

(209)

(210)

A method for synthesizing the above organic compound is described. As shown in a reaction scheme below, the organic compound represented by General Formula (G1) can be obtained by coupling of an aryl compound (a1) having a halogen group and an aryl compound (a2) having an amine.

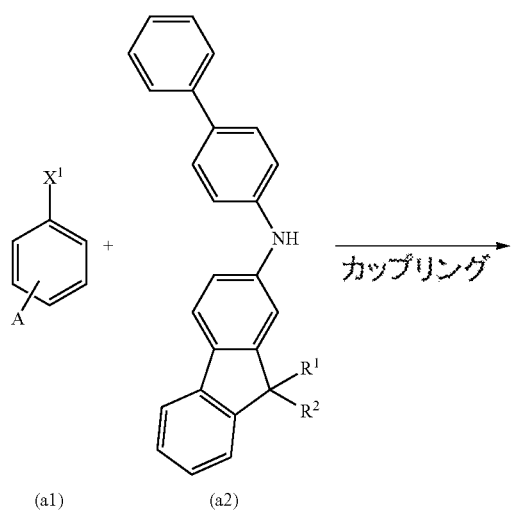

(G1)

In the synthesis scheme, A represents any one of a dibenzofuranyl group and a dibenzothiophenyl group, $R^1$ and $R^2$ separately represent any one of hydrogen, an alkyl group having 1 to 6 carbon atoms, and a phenyl group. Note that when both $R^1$ and $R^2$ are phenyl groups, the phenyl groups may be bonded to each other to form a spirofluorene skeleton. $X^1$ represents a halogen, preferably bromine or iodine, which has high reactivity, more preferably iodine.

In the synthesis scheme above, there are a variety of reaction conditions for the coupling reaction of the aryl compound having a halogen group and the aryl compound having an amine (secondary arylamine compound); for example, a synthesis method using a metal catalyst in the presence of a base can be applied.

The case where a Hartwig-Buchwald reaction is used in the synthesis scheme is described. A palladium catalyst can be used as the metal catalyst, and a mixture of a palladium complex and a ligand thereof can be used as the palladium catalyst. As the palladium complex, bis(dibenzylideneacetone)palladium(0), palladium(II) acetate, and the like are given. Examples of the ligand include tri(tert-butyl)phosphine, tri(n-hexyl)phosphine, tricyclohexylphosphine, 1,1'-bis(diphenylphosphino)ferrocene (abbreviation: DPPF), di(1-adamantyl)-n-butylphosphine, tris(2,6-dimethoxyphenyl)phosphine, and the like. Examples of a substance which can be used as the base include organic bases such as sodium tert-butoxide, inorganic bases such as potassium carbonate, tripotassium phosphate, cesium carbonate, and the like. In addition, this reaction is preferably performed in a solution, and examples of the solvent that can be used are toluene, xylene, benzene, mesitylene, and the like. However, the catalyst, ligand, base, and solvent which can be used are not limited to these examples. In addition, the reaction is preferably performed under an inert atmosphere of nitrogen, argon, or the like.

The case where an Ullmann reaction is used in the synthesis scheme is described. A copper catalyst can be used as the metal catalyst, and copper(I) iodide and copper(II) acetate are given as the copper catalyst. As an example of a substance which can be used for the base, an inorganic base such as potassium carbonate is given. The reaction is preferably performed in a solution, and examples of the solvent that can be used are 1,3-dimethyl-3,4,5,6-tetrahydro-2(1H) pyrimidinone (abbreviation: DMPU), toluene, xylene, benzene, mesitylene, and the like. However, the catalyst, base, and solvent which can be used are not limited to these examples. In addition, the reaction is preferably performed under an inert atmosphere of nitrogen, argon, or the like.

Note that a solvent having a high boiling point such as DMPU, xylene, or mesitylene is preferably used because, in an Ullmann reaction, a target substance can be obtained in a shorter time and at a higher yield when the reaction temperature is 100° C. or higher. A reaction temperature higher than 150° C. is further preferred and accordingly DMPU or mesitylene is more preferably used.

Through the above-described steps, the organic compound described in this embodiment can be synthesized.

By the use of the organic compound described in this embodiment, a light-emitting element using an exciplex as an emission center can have extremely high external quantum efficiency. A light-emitting element in which the organic compound is used as one of substances forming an exciplex that is an emission center can be driven at low voltage. Accordingly, the light-emitting element can have extremely high power efficiency. Note that the organic compound described in this embodiment has a hole-transport property, and thus it can be favorably used as a material included in a hole-transport layer.

A light-emitting element in which the exciplex is used as a substance having a function of transferring energy to a phosphorescent substance can also have high external quantum efficiency. Such a light-emitting element can be driven at low voltage and thus can have extremely high power efficiency.

Embodiment 2

In this embodiment, description is given of a structure of a light-emitting element in which the organic compound described in Embodiment 1 is used as one of two kinds of substances forming an exciplex.

As a method for converting a triplet excited state into light emission, there are a method utilizing phosphorescence, which is direct emission from a triplet excited state, and a method utilizing delayed fluorescence, which is light emitted from a singlet excited state after a triplet excited state is turned into a singlet excited state via reverse intersystem crossing.

A structure of a light-emitting element that uses a phosphorescent material and emits light with extremely high efficiency has been actually reported, which proves advantages of the utilization of a triplet excited state for light emission.

Some degree of success in a light-emitting element using a delayed fluorescence material has been achieved in recent years. However, a substance emitting delayed fluorescence with relatively high efficiency has an extremely rare state where a singlet excited state and a triplet excited state are close to each other and accordingly has a unique molecular structure; thus, the kind of such a substance is still limited.

It has been reported that an exciplex (also called excited complex) is a complex in an excited state which is formed by two kinds of molecules due to charge-transfer interaction and that the singlet excited state and the triplet excited state of an exciplex are close to each other in many cases.

Therefore, an exciplex readily emits delayed fluorescence even at room temperature and might allow a fluorescent light-emitting element to have high efficiency. Light emitted by an exciplex has a wavelength equivalent to a difference between a shallower HOMO level and a deeper LUMO level of the two kinds of substances that form the complex. Thus, light with a desired wavelength can be obtained relatively easily by selection of substances forming an exciplex.

However, positive use of light emission from an exciplex is still under investigation. There are few guidelines for selecting substances to achieve high emission efficiency, and without any guideline, a favorable light-emitting element will never be provided.

In view of the above, in this embodiment, a structure of a light-emitting element in which an exciplex is used as an emission center and which emits light with high efficiency is described.

A light-emitting element in this embodiment includes a layer containing an organic compound (the layer may also contain an inorganic compound) between a pair of electrodes, and the layer containing an organic compound at least includes a light-emitting layer. The light-emitting layer contains a first organic compound with an electron-transport property and a second organic compound with a hole-transport property.

A combination of the first organic compound and the second organic compound forms an exciplex when they are excited by a current or when a current flows therein. To form an exciplex, the HOMO level and LUMO level of the first organic compound are preferably positioned deeper than the HOMO level and LUMO level of the second organic compound, respectively.

The formation process of the exciplex is considered to be roughly classified into the following two processes.

One formation process is the process in which an exciplex is formed by the first organic compound with an electron-transport property and the second organic compound with a hole-transport property which are in the state of having carriers (cation or anion).

The other formation process is an elementary process in which one of the first organic compound with an electron-transport property and the second organic compound with a hole-transport property forms a singlet exciton and then the singlet exciton interacts with the other in the ground state to form an exciplex.

The exciplex in this embodiment may be formed by either process.

Here, when the organic compound described in Embodiment 1 is used as the second organic compound with a hole-transport property, efficient light emission from the exciplex can be obtained.

It is preferable that triplet excitation energy of each of the first organic compound and the second organic compound (energy equivalent to a difference between a triplet excited level and a singlet excited level) be higher than triplet excitation energy of the exciplex. This is because when the triplet excitation energy of each of the first organic compound and the second organic compound is lower than that of the exciplex, the triplet excitation energy of the exciplex is transferred, which inhibits efficient light emission.

Note that triplet excitation energy of an exciplex, whose singlet excited state and triplet excited state has a small energy difference, can be considered equivalent to the emission wavelength of the exciplex.

As the first organic compound with an electron-transport property, an electron-transport material having an electron mobility of $10^{-6}$ $cm^2/s$ or higher can be used mainly. Specifically, a t-electron deficient heteroaromatic compound such as a nitrogen-containing heteroaromatic compound is preferable, and for example, the following compounds can be used: heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3'-(dibenzothiophen-4-yl) biphenyl-3-yl]dibenzo[f,h]quinoxaline (abbreviation: 2mDBTBPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); and heterocyclic compounds having pyridine skeletons, such as 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above-described compounds, the heterocyclic compounds having quinoxaline skeletons or dibenzoquinoxaline skeletons, the heterocyclic compounds having diazine skeletons, and the heterocyclic compounds having pyridine skeletons have high reliability and can be preferably used. The following can also be given as the first organic compound: triaryl phosphine oxides such as phenyl-di(1-pyrenyl)phosphine oxide (abbreviation: POPy$_2$), spiro-9,9'-bifluoren-2-yl-diphenylphosphine oxide (abbreviation: SPPO1), 2,8-bis(diphenylphosphoryl)dibenzo[b,d]thiophene (abbreviation: PPT), and 3-(diphenylphosphoryl)-9-[4-(diphenylphosphoryl)phenyl]-9H-carbazole (abbreviation: PPO21); and triaryl borane such as tris[2,4,6-trimethyl-3-(3-pyridyl)phenyl]borane (abbreviation: 3TPYMB). Note that a heterocyclic compound with a diazine skeleton, specifically a heterocyclic compound with a pyrimidine skeleton, is preferably used, in which case light can be emitted with higher efficiency.

An exciplex formed by the first organic compound as described above and the second organic compound that is the organic compound in Embodiment 1 can emit light with extremely high efficiency, and accordingly, the light-emitting element in this embodiment can emit light with high efficiency. Although the theoretical limit of external quantum efficiency of a fluorescent light-emitting element is generally considered to be 5% to 7% when it is not designed to enhance extraction efficiency, a light-emitting element having external quantum efficiency higher than the theoretical limit can be easily provided by the use of the structure of the light-emitting element in this embodiment.

As described above, because the emission wavelength of an exciplex is equivalent to a difference between a shallower HOMO level and a deeper LUMO level of the first and second organic compounds, a light-emitting element emitting light with a desired wavelength can be easily provided by selection of substances each of which has an appropriate level.

In this manner, the structure in this embodiment makes it possible to provide a high-efficiency light-emitting element in which a triplet excited state can be converted into light emission. Besides, light-emitting elements with such characteristics can be provided without severe limitation on their emission wavelengths.

Note that a light-emitting layer of a light-emitting element with the structure described in this embodiment may be added with a fluorescent substance so that light emission from the fluorescent substance is provided. Because the light-emitting element uses an exciplex capable of converting a triplet excited state into a singlet excited state as a substance having a function of transferring energy, the fluorescent substance can emit light with high efficiency. Moreover, the light-emitting element can have a long lifetime because light emission is obtained from the fluorescent substance, which has stability.

Embodiment 3

In this embodiment, description is given of the light-emitting element in Embodiment 2 in which the light-emitting layer further contains a phosphorescent substance and which emits light from the phosphorescent substance. The light-emitting element in this embodiment has the same structure as the light-emitting element in Embodiment 2 except that the light-emitting layer contains the phosphorescent substance. Description of the common structures and materials is not repeated. The corresponding description in Embodiment 2 is to be referred to.

Because the light-emitting layer contains the phosphorescent substance, efficient energy transfer from an exciplex to the phosphorescent substance can be performed.

Here, to achieve high emission efficiency of a light-emitting element that uses a phosphorescent substance, energy transfer between the host material and the phosphorescent substance will be considered. Carrier recombination occurs in both the host material and the phosphorescent substance; thus, efficient energy transfer from the host material to the phosphorescent substance is necessary to increase emission efficiency.

As mechanisms of the energy transfer from the host material to the phosphorescent substance, two mechanisms have been proposed: one is Dexter mechanism, and the other is Förster mechanism. Each mechanism is described below. Here, a molecule providing excitation energy is referred to as a host molecule, while a molecule receiving the excitation energy is referred to as a guest molecule.

<<Förster Mechanism (Dipole-Dipole Interaction)>>

Förster mechanism (also referred to as Förster resonance energy transfer) does not require direct contact between molecules for energy transfer. Through a resonant phenomenon of dipolar oscillation between a host molecule and a guest molecule, energy transfer occurs. By the resonant phenomenon of dipolar oscillation, the host molecule provides energy to the guest molecule, and thus, the host molecule returns to a ground state and the guest molecule reaches an excited state. The rate constant $k_{h^* \to g}$ of Förster mechanism is expressed by Formula (1).

[Formula 1]

$$k_{h^* \to g} = \frac{9000c^4 K^2 \phi \ln 10}{128\pi^5 n^4 N \tau R^6} \int \frac{f'_h(v)\varepsilon_g(v)}{v^4} dv \qquad (1)$$

In Formula (1), v denotes a frequency, $f'_h(v)$ denotes a normalized emission spectrum of a host molecule (a fluorescence spectrum in energy transfer from a singlet excited state, and a phosphorescence spectrum in energy transfer from a triplet excited state), $\varepsilon_g(v)$ denotes a molar absorption coefficient of a guest molecule, N denotes Avogadro's number, n denotes a refractive index of a medium, R denotes an intermolecular distance between the host molecule and the guest molecule, i denotes a measured lifetime of an excited state (fluorescence lifetime or phosphorescence lifetime), c denotes the speed of light, φ denotes a luminescence quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host molecule and the guest molecule. Note that $K^2 = 2/3$ in random orientation.

<<Dexter Mechanism (Electron Exchange Interaction)>>

In Dexter mechanism (also referred to as Dexter electron transfer), a host molecule and a guest molecule are close to a contact effective range where their orbitals can overlap, and the host molecule in an excited state and the guest molecule in a ground state exchange their electrons, which leads to energy transfer. The rate constant $k_{h^* \to g}$ of Dexter mechanism is expressed by Formula (2).

[Formula 2]

$$k_{h^* \to g} = \left(\frac{2\pi}{h}\right) K^2 \exp\left(-\frac{2R}{L}\right) \int f'_h(\nu) \varepsilon'_g(\nu) d\nu \quad (2)$$

In Formula (2), h denotes a Planck constant, K denotes a constant having an energy dimension, ν denotes a frequency, $f'_h(\nu)$ denotes a normalized emission spectrum of a host molecule (a fluorescence spectrum in energy transfer from a singlet excited state, and a phosphorescence spectrum in energy transfer from a triplet excited state), $\varepsilon'_g(\nu)$ denotes a normalized absorption spectrum of a guest molecule, L denotes an effective molecular radius, and R denotes an intermolecular distance between the host molecule and the guest molecule.

Here, the efficiency of energy transfer from the host molecule to the guest molecule (energy transfer efficiency $\Phi_{ET}$) is expressed by Formula (3). In the formula, $k_r$ denotes a rate constant of a light-emission process (fluorescence in energy transfer from a singlet excited state, and phosphorescence in energy transfer from a triplet excited state), $k_n$ denotes a rate constant of a non-light-emission process (thermal deactivation or intersystem crossing), and τ denotes a measured lifetime of an excited state.

[Formula 3]

$$\Phi_{ET} = \frac{k_{h^* \to g}}{k_r + k_n + k_{h^* \to g}} = \frac{k_{h^* \to g}}{\left(\frac{1}{\tau}\right) + k_{h^* \to g}} \quad (3)$$

First, according to Formula (3), it is understood that the energy transfer efficiency $\Phi_{ET}$ can be increased by significantly increasing the rate constant $k_{h^* \to g}$ of energy transfer as compared with another competing rate constant $k_r + k_n$ (=1/τ). Then, in order to increase the rate constant $k_{h^* \to g}$ of energy transfer, based on Formulae (1) and (2), in Förster mechanism and Dexter mechanism, it is preferable that an emission spectrum of a host molecule (a fluorescence spectrum in energy transfer from a singlet excited state, and a phosphorescence spectrum in energy transfer from a triplet excited state) has a large overlap with an absorption spectrum of a guest molecule.

Here, a longest-wavelength-side (lowest-energy-side) absorption band in the absorption spectrum of the guest molecule is important in considering the overlap between the emission spectrum of the host molecule and the absorption spectrum of the guest molecule.

In this embodiment, a phosphorescent substance is used as the guest material. In an absorption spectrum of the phosphorescent substance, an absorption band that is considered to contribute to light emission most greatly is at an absorption wavelength corresponding to direct transition from a ground state to a triplet excitation state and a vicinity of the absorption wavelength, which is on the longest wavelength side. Therefore, it is considered preferable that the emission spectrum (a fluorescence spectrum and a phosphorescence spectrum) of the host material overlap with the absorption band on the longest wavelength side in the absorption spectrum of the phosphorescent substance.

For example, most organometallic complexes, especially light-emitting iridium complexes, have a broad absorption band around 500 nm to 600 nm as the absorption band on the longest wavelength side. This absorption band is mainly based on a triplet MLCT (metal to ligand charge transfer) transition. Note that it is considered that the absorption band also includes absorptions based on a triplet π-π* transition and a singlet MLCT transition, and that these absorptions overlap each other to form a broad absorption band on the longest wavelength side in the absorption spectrum. Therefore, when an organometallic complex (especially iridium complex) is used as the guest material, it is preferable to make the broad absorption band on the longest wavelength side have a large overlap with the emission spectrum of the host material as described above.

Here, first, energy transfer from a host material in a triplet excited state will be considered. From the above-described discussion, it is preferable that, in energy transfer from a triplet excited state, the phosphorescence spectrum of the host material and the absorption band on the longest wavelength side of the guest material have a large overlap.

However, a question here is energy transfer from the host molecule in the singlet excited state. In order to efficiently perform not only energy transfer from the triplet excited state but also energy transfer from the singlet excited state, it is clear from the above-described discussion that the host material needs to be designed such that not only its phosphorescence spectrum but also its fluorescence spectrum overlaps with the absorption band on the longest wavelength side of the guest material. In other words, unless the host material is designed so as to have its fluorescence spectrum in a position similar to that of its phosphorescence spectrum, it is not possible to achieve efficient energy transfer from the host material in both the singlet excited state and the triplet excited state.

However, in general, the $S_1$ level differs greatly from the $T_1$ level ($S_1$ level>$T_1$ level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used in a light-emitting element containing a phosphorescent substance, has a phosphorescence spectrum around 500 nm and has a fluorescence spectrum around 400 nm, which are largely different by approximately 100 nm. This example also shows that it is extremely difficult to design a host material so as to have its fluorescence spectrum in a position similar to that of its phosphorescence spectrum.

Also, since the $S_1$ level is higher than the $T_1$ level, the $T_1$ level of a host material whose fluorescence spectrum corresponds to a wavelength close to an absorption spectrum of a guest material on the longest wavelength side is lower than the $T_1$ level of the guest material.

Thus, an exciplex is utilized as in this embodiment, so that the efficiency of energy transfer can be enhanced.

A fluorescence spectrum of the exciplex is on a longer wavelength side than a fluorescence spectrum of the first organic compound alone or the second organic compound alone. Therefore, energy transfer from a singlet excited state can be maximized while the $T_1$ levels of the first organic compound and the second organic compound are kept higher than the $T_1$ level of the guest material. In addition, the exciplex is in a state where the $T_1$ level and the $S_1$ level are close to each other; therefore, the fluorescence spectrum and the phosphorescence spectrum exist at substantially the same position. Accordingly, both the fluorescence spectrum and the phosphorescence spectrum of the exciplex can have a large overlap with an absorption corresponding to transition of the guest molecule from the singlet ground state to the triplet excited state (a broad absorption band of the guest molecule existing on the longest wavelength side in the absorption spectrum), and thus a light-emitting element having high energy transfer efficiency can be obtained.

Carrier balance can be controlled by adjusting the mixture ratio of the first organic compound with an electron-transport property to the second organic compound with a hole-transport property. Specifically, the ratio of the first organic compound to the second organic compound (or additive) is preferably from 1:9 to 9:1. Note that in that case, the following structure may be employed: a light-emitting layer in which one kind of a phosphorescent substance is dispersed is divided into two layers, and the two layers have different mixture ratios of the first organic compound to the second organic compound. With this structure, the carrier balance in the light-emitting element can be optimized, so that the lifetime of the light-emitting element can be improved. Furthermore, in this case, one of the light-emitting layers may be a hole-transport layer and the other of the light-emitting layers may be an electron-transport layer.

A material that can be used as the phosphorescent substance is not particularly limited. Examples of a blue phosphorescent substance include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), or tris[4-(3-biphenyl)-5-isopropyl-3-phenyl-4H-1,2,4-triazolato]iridium (II) (abbreviation: Ir(iPrptz-3b)$_3$); an organometallic iridium complex having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) or tris(1-methyl-5-phenyl-3-propyl-1H-1,2,4-triazolato)iridium(III) (abbreviation: Ir(Prptz1-Me)$_3$); an organometallic iridium complex having an imidazole skeleton, such as fac-tris[1-(2,6-diisopropylphenyl)-2-phenyl-1H-imidazole]iridium (III) (abbreviation: Ir(iPrpmi)$_3$) or tris[3-(2,6-dimethylphenyl)-7-methylimidazo[1,2-f]phenanthridinato]iridium(III) (abbreviation: Ir(dmpimpt-Me)$_3$); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^2$}iridium(III) picolinate (abbreviation: Ir(CF$_3$ppy)$_2$(pic)), or bis[2-(4',6'-difluorophenyl)pyridinato-N,C$^{2'}$]iridium(III) acetylacetonate (abbreviation: FIr(acac)). Note that an organometallic iridium complex having a 4H-triazole skeleton has excellent reliability and emission efficiency and thus is especially preferable. Examples of a green phosphorescent substance include an organometallic iridium complex having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium (III) (abbreviation: Ir(tBuppm)$_3$), (acetylacetonato)bis(6-methyl-4-phenylpyrimidinato)iridium(III) (abbreviation: Ir(mppm)$_2$(acac)), bis[2-(6-tert-butyl-4-pyrimidinyl-κN3)phenyl-κC](2,4-pentanedionato-κ$^2$O,O') iridium(III) (abbreviation: Ir(tBuppm)$_2$(acac)), (acetylacetonato)bis[6-(2-norbornyl)-4-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium (III) (abbreviation: Ir(mpmppm)$_2$(acac)), or (acetylacetonato)bis(4,6-diphenylpyrimidinato)iridium(III) (abbreviation: Ir(dppm)$_2$(acac)); an organometallic iridium complex having a pyrazine skeleton, such as (acetylacetonato)bis(3,5-dimethyl-2-phenylpyrazinato)iridium(III) (abbreviation: Ir(mppr-Me)$_2$(acac)) or (acetylacetonato)bis(5-isopropyl-3-methyl-2-phenylpyrazinato)iridium(III) (abbreviation: Ir(mppr-iPr)$_2$(acac)); an organometallic iridium complex having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium (III) (abbreviation: Ir(pq)$_3$), or bis(2-phenylquinolinato-N,C$^{2'}$)iridium(II) acetylacetonate (abbreviation: Ir(pq)$_2$(acac)); and a rare earth metal complex such as tris(acetylacetonato)(monophenanthroline)terbium(III) (abbreviation: Tb(acac)$_3$(Phen)). Note that an organometallic iridium complex having a pyrimidine skeleton has distinctively high reliability and emission efficiency and thus is especially preferable. Examples of a red phosphorescent substance include an organometallic iridium complex having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), or bis[4,6-di(naphthalen-1-yl)pyrimidinato](dipivaloylmethanato)iridium(III) (abbreviation: Ir(d1npm)$_2$(dpm)); an organometallic iridium complex having a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: Ir(tppr)$_2$(dpm)), (acetylacetonato)bis[2,3-bis(4-fluorophenyl)quinoxalinato]iridium(III) (abbreviation: Ir(Fdpq)$_2$(acac)); an organometallic iridium complex having a pyridine skeleton, such as tris(1-phenylisoquinolinato-N,C$^{2'}$)iridium(III) (abbreviation: Ir(piq)$_3$) or bis(1-phenylisoquinolinato-N,C$^{2'}$)iridium(III)acetylacetonate (abbreviation: Ir(piq)$_2$(acac); a platinum complex such as 2,3,7,8,12,13,17,18-octaethyl-21H,23H-porphyrin platinum(II) (abbreviation: PtOEP); and a rare earth metal complex such as tris(1,3-diphenyl-1,3-propanedionato)(monophenanthroline)europium(III) (abbreviation: Eu(DBM)$_3$(Phen)) or tris[1-(2-thenoyl)-3,3,3-trifluoroacetonato](monophenanthroline)europium(III) (abbreviation: Eu(TTA)$_3$(Phen)). Note that an organometallic iridium complex having a pyrimidine skeleton has distinctively high reliability and emission efficiency and thus is especially preferable. Further, because an organometallic iridium complex having a pyrazine skeleton can provide red light emission with favorable chromaticity, the use of the organometallic iridium complex in a white light-emitting element improves a color rendering property of the white light-emitting element. Note that an organic compound with a benzofuropyrimidine skeleton also emits light in blue to ultraviolet regions and thus can be used as an emission center material. A compound with a benzofuropyrimidine skeleton may also be used.

The material that can be used as the phosphorescent substance may also be selected from various other substances instead of the substances given above.

A light-emitting element with the above structure has high energy transfer efficiency and thus can have high external quantum efficiency. A phosphorescent light-emitting element that emits light by utilizing energy transfer from an exciplex can be driven at low voltage. Accordingly, the light-emitting element in this embodiment can have extremely high power efficiency.

Embodiment 4

In this embodiment, a detailed example of the structure of the light-emitting element described in Embodiment 2 or 3 will be described below with reference to FIGS. 1A and 1B.

In FIG. 1A, the light-emitting element includes a first electrode 101, a second electrode 102, and a layer 103 containing an organic compound and provided between the first electrode 101 and the second electrode 102. Note that in this embodiment, the first electrode 101 functions as an anode and the second electrode 102 functions as a cathode. In other words, when voltage is applied between the first electrode 101 and the second electrode 102 so that the potential of the first electrode 101 is higher than that of the second electrode 102, light emission can be obtained. The layer 103 containing an organic compound at least includes a light-emitting layer 113. A hole-injection layer 111, a hole-transport layer 112, an electron-transport layer 114, and an electron-injection layer 115 which are illustrated in FIG. 1A are merely examples and not necessarily provided. A layer having any other function may also be provided.

The first electrode 101 functions as the anode and is preferably formed using any of metals, alloys, electrically conductive compounds with a high work function (specifically, a work function of 4.0 eV or more), mixtures thereof, and the like. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Such conductive metal oxide films are usually formed by a sputtering method, but may also be formed by application of a sol-gel method or the like. In an example of the formation method, indium oxide-zinc oxide is deposited by a sputtering method using a target obtained by adding 1 wt % to 20 wt % of zinc oxide to indium oxide. Further, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like can be used. Graphene can also be used. Note that when a composite material described later is used for a layer which is in contact with the first electrode 101 in the layer 103 containing an organic compound, an electrode material can be selected regardless of its work function.

There is no particular limitation on the stacked structure of the layer 103 containing an organic compound as long as the light-emitting layer 113 has the structure described in Embodiment 2 or 3. For example, in FIG. 1A, the layer 103 containing an organic compound can be formed by combining a hole-injection layer, a hole-transport layer, the light-emitting layer, an electron-transport layer, an electron-injection layer, a carrier-blocking layer, a charge-generation layer, and the like as appropriate. In this embodiment, the layer 103 containing an organic compound has a structure in which the hole-injection layer 111, the hole-transport layer 112, the light-emitting layer 113, the electron-transport layer 114, and the electron-injection layer 115 are stacked in this order over the first electrode 101. Materials for the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis {4-[bis(3-methylphenyl)amino]phenyl}-N,N'-diphenyl-(1,1'-biphenyl)-4,4'-diamine (abbreviation: DNTPD), a high molecular compound such as poly(3, 4-ethylenedioxythiophene)/poly(styrenesulfonic acid) (PEDOT/PSS), or the like.

Alternatively, a composite material in which a material with a hole-transport property contains an acceptor substance can be used for the hole-injection layer 111. Note that the use of such a material with a hole-transport property which contains an acceptor substance enables selection of a material used to form an electrode regardless of its work function. In other words, besides a material having a high work function, a material having a low work function can also be used for the first electrode 101. As the acceptor substance, 7,7,8,8-tetracyano-2,3,5,6-tetrafluoroquinodimethane (abbreviation: $F_4$-TCNQ), chloranil, and the like can be given. In addition, a transition metal oxide can be given. In addition, oxides of metals belonging to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easily handled.

As the material with a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ $cm^2/Vs$ or higher is preferably used. Organic compounds which can be used as the material having a hole-transport property in the composite material are specifically given below.

Examples of the aromatic amine compound include N,N'-di(p-tolyl)-N,N'-diphenyl-p-phenylenediamine (abbreviation: DTDPPA), 4,4'-bis[N-(4-diphenylaminophenyl)-N- phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

As carbazole derivatives which can be used for the composite material, the following can be given specifically: 3-[N-(9-phenylcarbazol-3-yl)-N-phenylamino]-9-phenyl-carbazole (abbreviation: PCzPCA1); 3,6-bis[N-(9-phenyl-carbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like.

In addition, examples of the carbazole derivatives which can be used for the composite material include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl,
anthracene, tetracene, rubrene, perylene, and 2,5,8,11-tetra(tert-butyl)perylene. Besides, pentacene, coronene, or the like can also be used. The aromatic hydrocarbon which has a hole mobility of $1\times10^{-6}$ cm$^2$/Vs or more and which has 14 to 42 carbon atoms is particularly preferable.

The aromatic hydrocarbon which can be used for the composite material may have a vinyl skeleton. Examples of the aromatic hydrocarbon having a vinyl group include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine (abbreviation: poly-TPD) can also be used. Note that as the material having a hole-transport property in the composite material, the organic compound described in Embodiment 1 can also be used.

By providing a hole-injection layer, a high hole-injection property can be achieved to allow a light-emitting element to be driven at a low voltage.

The hole-transport layer is a layer containing a material having a hole-transport property. Examples of the material having a hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), and the like. The substances given here have high hole-transport properties and are mainly ones having a hole mobility of $10^{-6}$ cm$^2$/Vs or more. An organic compound given as an example of the material with a hole-transport property in the composite material described above can also be used for the hole-transport layer. Moreover, a high molecular compound such as poly(N-vinylcarbazole) (abbreviation: PVK) or poly(4-vinyltriphenylamine) (abbreviation: PVTPA) can also be used. The organic compound described in Embodiment 1 can also be used. Note that the layer containing a material with a hole-transport property is not limited to a single layer, and may be a stack of two or more layers containing any of the above substances.

Although the light-emitting layer 113, which has a function of emitting light, may have any of a variety of structures and may include any of a variety of materials, it is preferable that the light-emitting layer contain the first organic compound with an electron-transport property and the second organic compound with a hole-transport property. The light-emitting layer may further contain a phosphorescent substance or a fluorescent substance. Further preferable materials, structures, and the like are as described in Embodiment 2 or 3. By having such a structure, the light-emitting element in this embodiment has extremely high external quantum efficiency. The light-emitting element also has an advantage in that its emission wavelength can be easily adjusted and thus light in desired wavelength ranges can be easily obtained with the efficiency kept high.

The electron-transport layer 114 is a layer containing a material having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here have high electron-transport properties and are mainly ones that have an electron mobility of $10^{-6}$ cm$^2$/Vs or more. Note that the above-described first organic compound with an electron-transport property may be used for the electron-transport layer 114.

The electron-transport layer 114 is not limited to a single layer, and may be a stack including two or more layers containing any of the above substances.

Between the electron-transport layer and the light-emitting layer, a layer that controls transport of electron carriers may be provided. This is a layer formed by addition of a small amount of a substance having a high electron-trapping property to the aforementioned materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

In addition, an electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. Note that a layer that is formed using a substance having an electron-transport property and contains an alkali metal or an alkaline earth metal is preferably used as the electron-injection layer 115, in which case electron injection from the second electrode 102 is efficiently performed.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Any of a variety of methods can be used to form the layer 103 containing an organic compound regardless whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light emission is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Further, to inhibit transfer of energy from an exciton generated in the light-emitting layer, preferably, the hole-transport layer and the electron-transport layer which are in contact with the light-emitting layer 113, particularly a carrier-transport layer in contact with a side closer to the light-emitting region in the light-emitting layer 113, are formed using a substance having a wider band gap than the exciplex included in the light-emitting layer.

Figure 1B:
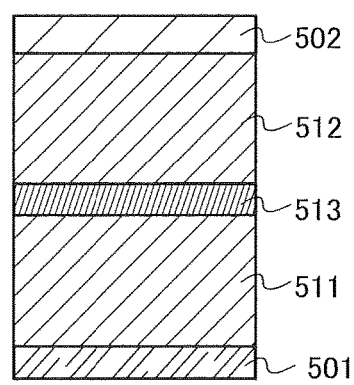

FIG. 1B shows a light-emitting element having different structure from FIG. 1A. One embodiment of a light-emitting element in which a plurality of light-emitting units are stacked (hereinafter, also referred to as a stacked-layer element) will be described with reference to FIG. 1B. This light-emitting element is a light-emitting element including a plurality of light-emitting units between a first electrode and a second electrode. One light-emitting unit has a structure similar to that of the layer 103 containing an organic compound, which is illustrated in FIG. 1A. In other words, the light-emitting element illustrated in FIG. 1A includes a single light-emitting unit; the light-emitting element illustrated in FIG. 1B includes a plurality of light-emitting units.

In FIG. 1B, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Further, the first light-emitting unit 511 and the second light-emitting unit 512 may have the same structure or different structures.

The charge-generation layer 513 includes a composite material of an organic compound and a metal oxide. As this composite material of an organic compound and a metal oxide, the composite material that can be used for the hole-injection layer and shown in FIG. 1A can be used. As the organic compound, a variety of compounds such as an aromatic amine compound, a carbazole compound, an aromatic hydrocarbon, and a high molecular compound (such as an oligomer, a dendrimer, or a polymer) can be used. An organic compound having a hole mobility of $1 \times 10^{-6}$ $cm^2/Vs$ or higher is preferably used. Note that any other substance may be used as long as the substance has a hole-transport property higher than an electron-transport property. The composite material of the organic compound and the metal oxide can achieve low-voltage driving and low-current driving because of the superior carrier-injection property and carrier-transport property. Note that in the light-emitting unit whose anode side surface is in contact with the charge-generation layer, a hole-transport layer is not necessarily provided because the charge-generation layer can also function as the hole-transport layer.

The charge-generation layer 513 may have a stacked-layer structure of a layer containing the composite material of an organic compound and a metal oxide and a layer containing another material. For example, a stacked-layer structure of a layer containing the composite material of an organic compound and a metal oxide and a layer containing a compound selected from electron-donating substances and a compound having a high electron-transport property may be formed. Moreover, a layer containing the composite material of an organic compound and a metal oxide may be stacked with a transparent conductive film.

The charge-generation layer 513 interposed between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge-generation layer 513 as long as the layer injects electrons into the first light-emitting unit 511 and holes into the second light-emitting unit 512 when a voltage is applied such that the potential of the first electrode is higher than that of the second electrode.

In FIG. 1B, the light-emitting element having two light-emitting units is described; however, one embodiment of the present invention can be similarly applied to a light-emitting element in which three or more light-emitting units are stacked. With a plurality of light-emitting units partitioned by the charge-generation layer between a pair of electrodes as in the light-emitting element illustrated in FIG. 1B, it is possible to provide a light-emitting element which can emit light with high luminance with the current density kept low and has a long lifetime. In addition, a low-power-consumption light-emitting device which can be driven at low voltage can be achieved.

The light-emitting units emit light having different colors from each other, thereby obtaining light emission of a desired color in the whole light-emitting element. For example, in a light-emitting element having two light-emitting units, the first light-emitting unit gives red and green emissions and the second light-emitting unit gives blue emission, so that the light-emitting element can emit white light as the whole element.

The above-described structure can be combined with any of the structures in this embodiment and the other embodiments.

A light-emitting element in this embodiment is preferably fabricated over a substrate of glass, plastic, or the like. As the way of stacking layers over the substrate, layers may be sequentially stacked from the first electrode 101 side or sequentially stacked from the second electrode 102 side. In a light-emitting device, although one light-emitting element may be formed over one substrate, a plurality of light-emitting elements may be formed over one substrate. With a plurality of light-emitting elements as described above formed over one substrate, a lighting device in which elements are separated or a passive-matrix light-emitting device can be manufactured. A light-emitting element may be formed over an electrode electrically connected to a thin film transistor (TFT), for example, which is formed over a substrate of glass, plastic, or the like, so that an active matrix light-emitting device in which the TFT controls the drive of the light-emitting element can be manufactured. Note that there is no particular limitation on the structure of the TFT, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

Note that this embodiment can be combined with any of the other embodiments as appropriate.

Embodiment 5

In this embodiment, a light-emitting device including the light-emitting element described in any of Embodiments 2 to 4 is described.

Figure 2A:
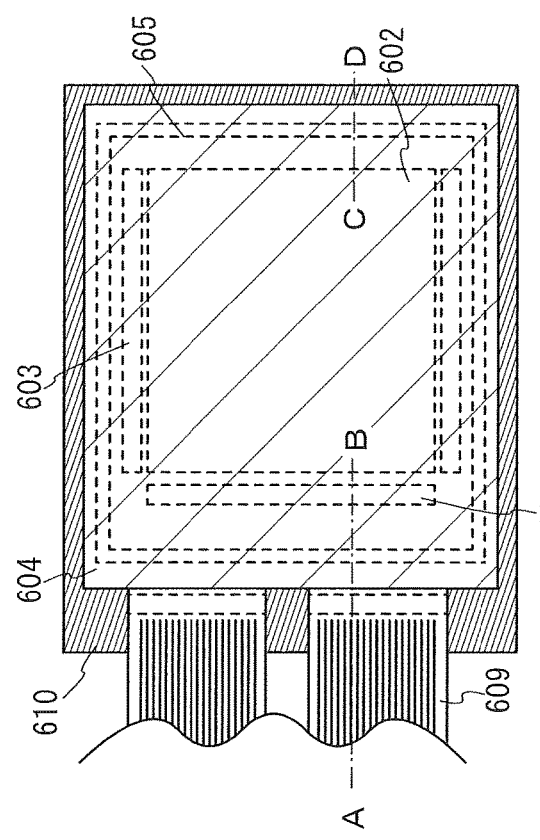
FIGS. 2A and 2B are conceptual diagrams of an active matrix light-emitting device.
Figure 2B:
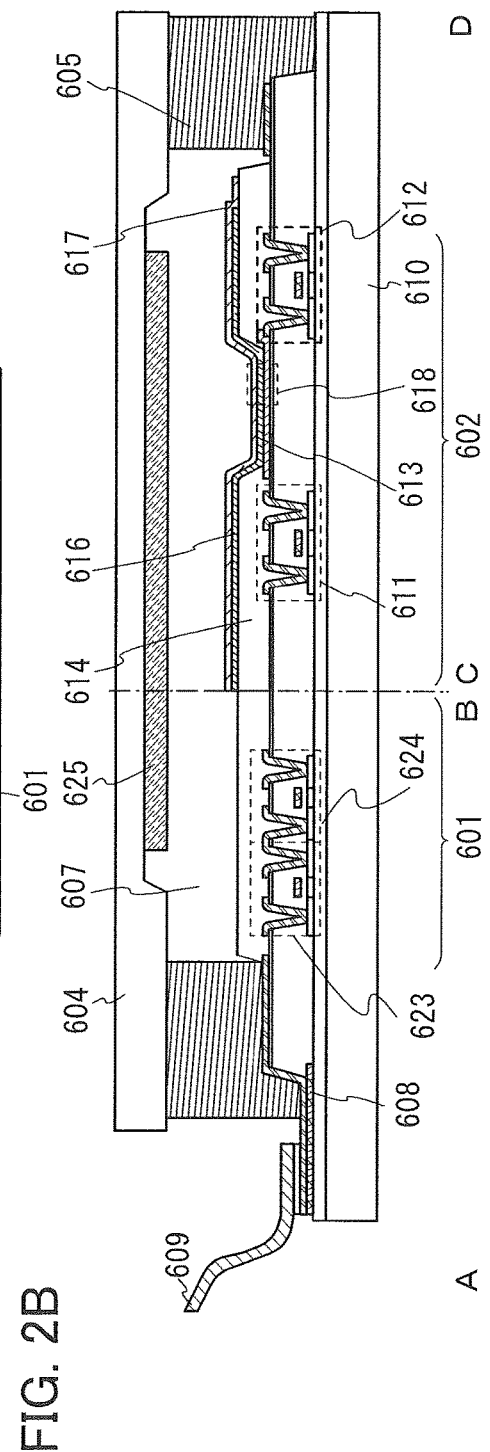

In this embodiment, the light-emitting device manufactured using the light-emitting element described in any of Embodiments 2 to 4 is described with reference to FIGS. 2A and 2B. Note that FIG. 2A is a top view illustrating the light-emitting device and FIG. 2B is a cross-sectional view of FIG. 2A taken along lines A-B and C-D. This light-emitting device includes a driver circuit portion (source line driver circuit) 601, a pixel portion 602, and a driver circuit portion (gate line driver circuit) 603, which control light emission of the light-emitting element and denoted by dotted lines. Moreover, a reference numeral 604 denotes a sealing substrate; 605, a sealing material; and 607, a space surrounded by the sealing material 605.

Note that a lead wiring 608 is a wiring for transmitting signals to be input to the source line driver circuit 601 and the gate line driver circuit 603 and for receiving a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 2B. The driver circuit portion and the pixel portion are formed over an element substrate 610; the source line driver circuit 601, which is a driver circuit portion, and one of the pixels in the pixel portion 602 are illustrated here.

In the source line driver circuit 601, a CMOS circuit is formed in which an n-channel TFT 623 and a p-channel TFT 624 are combined. In addition, the driver circuit may be formed with any of a variety of circuits such as a CMOS circuit, a PMOS circuit, or an NMOS circuit. Although a driver-integrated type in which the driver circuit is formed over the substrate is described in this embodiment, the present invention is not limited to this type and the driver circuit can be formed outside the substrate.

The pixel portion 602 is formed with a plurality of pixels including a switching TFT 611, a current controlling TFT 612, and a first electrode 613 connected electrically with a drain of the current controlling TFT. An insulator 614 is formed to cover the end portions of the first electrode 613. Here, the insulator 614 is formed using a positive type photosensitive acrylic resin film.

In order to improve the coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 µm to 3 µm). As the insulator 614, either a negative photosensitive resin or a positive photosensitive resin can be used.

A layer 616 containing an organic compound and a second electrode 617 are formed over the first electrode 613. As a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked-layer structure enables low wiring resistance, favorable ohmic contact, and a function as an anode.

In addition, the layer 616 containing an organic compound is formed by any of a variety of methods such as an evaporation method using an evaporation mask, an inkjet method, and a spin coating method. The layer 616 containing an organic compound has the structure described in any of Embodiments 2 to 4. Further, for another material included in the layer 616 containing an organic compound, any of low molecular-weight compounds and polymeric compounds (including oligomers and dendrimers) may be used.

As a material used for the second electrode 617, which is formed over the layer 616 containing an organic compound and functions as a cathode, a material-having a low work function (e.g., Al, Mg, Li, Ca, or an alloy or a compound thereof, such as MgAg, MgIn, or AlLi) is preferably used. In the case where light generated in the layer 616 containing an organic compound is transmitted through the second electrode 617, a stack including a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the layer 616 containing an organic compound, and the second electrode 617. The light-emitting element has the structure described in any of Embodiments 2 to 4. In the light-emitting device in this embodiment, the pixel portion, which includes a plurality of light-emitting elements, may include both the light-emitting element described in any of Embodiments 2 to 4 and a light-emitting element having a different structure.

Further, the sealing substrate 604 is attached to the element substrate 610 with the sealing material 605, so that the light-emitting element 618 is provided in the space 607 surrounded by the element substrate 610, the sealing substrate 604, and the sealing material 605. The space 607 may be filled with filler, or may be filled with an inert gas (such as nitrogen or argon), or the sealing material 605. It is preferable that the sealing substrate be provided with a recessed portion and the desiccant 625 be provided in the recessed portion, in which case deterioration due to influence of moisture can be inhibited.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), polyester, acrylic, or the like can be used.

As described above, the light-emitting device which uses the light-emitting element described in any of Embodiments 2 to 4 can be obtained.

The light-emitting device in this embodiment is fabricated using the light-emitting element described in any of Embodiments 2 to 4 and thus can have favorable characteristics. Specifically, since the light-emitting element described in any of Embodiments 2 to 4 has favorable emission efficiency, the light-emitting device can have reduced power consumption. In addition, light in desired wavelength ranges can be easily provided by the light-emitting element described in any of Embodiments 2 to 4, which makes it possible to provide a versatile light-emitting device.

Figures 3A, 3B:
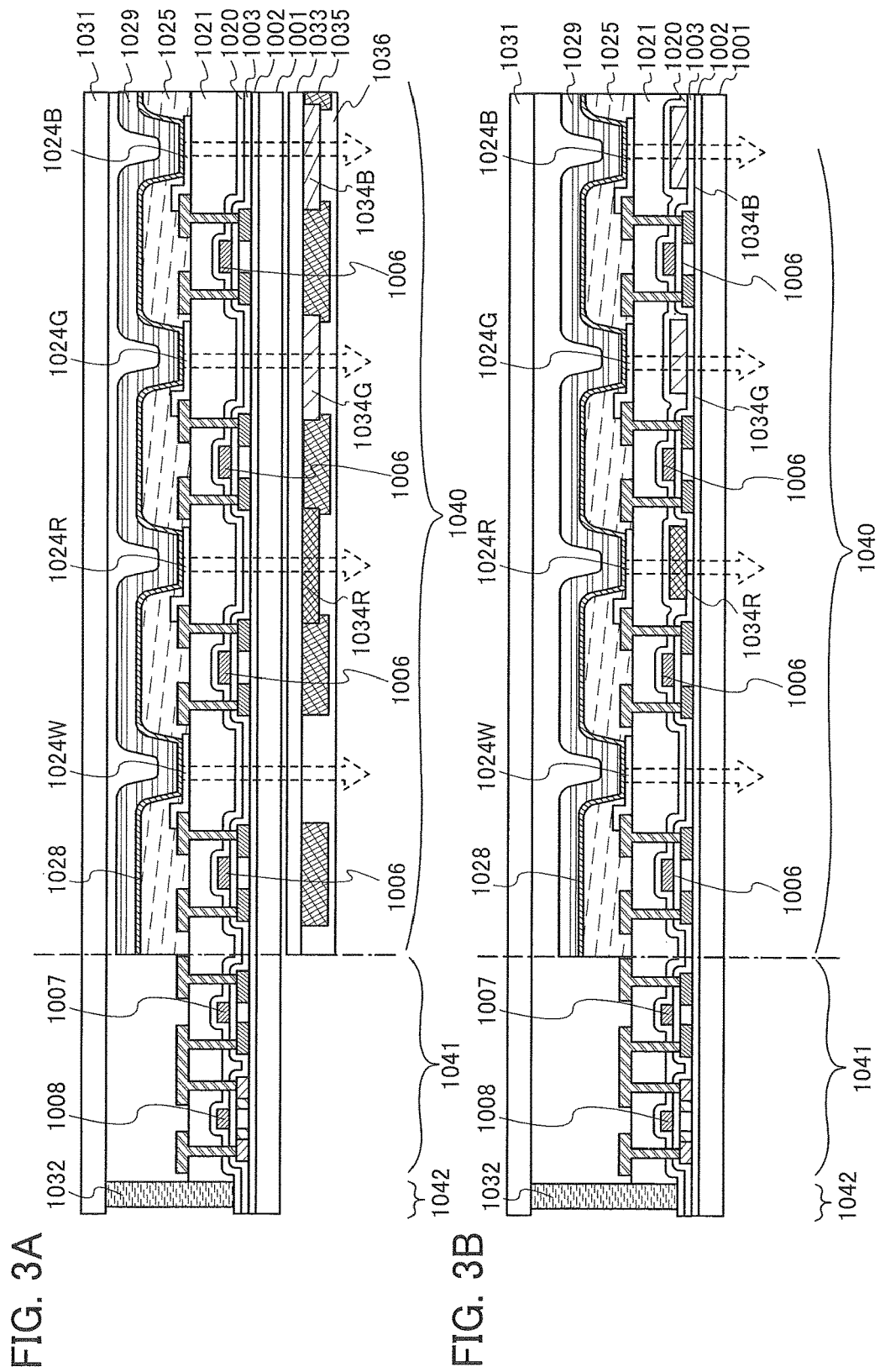
FIGS. 3A and 3B are conceptual diagrams of active matrix light-emitting devices.

FIGS. 3A and 3B each illustrate an example of a light-emitting device in which full color display is achieved by formation of a light-emitting element exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, a layer 1028 containing an organic compound, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, blue, or green, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
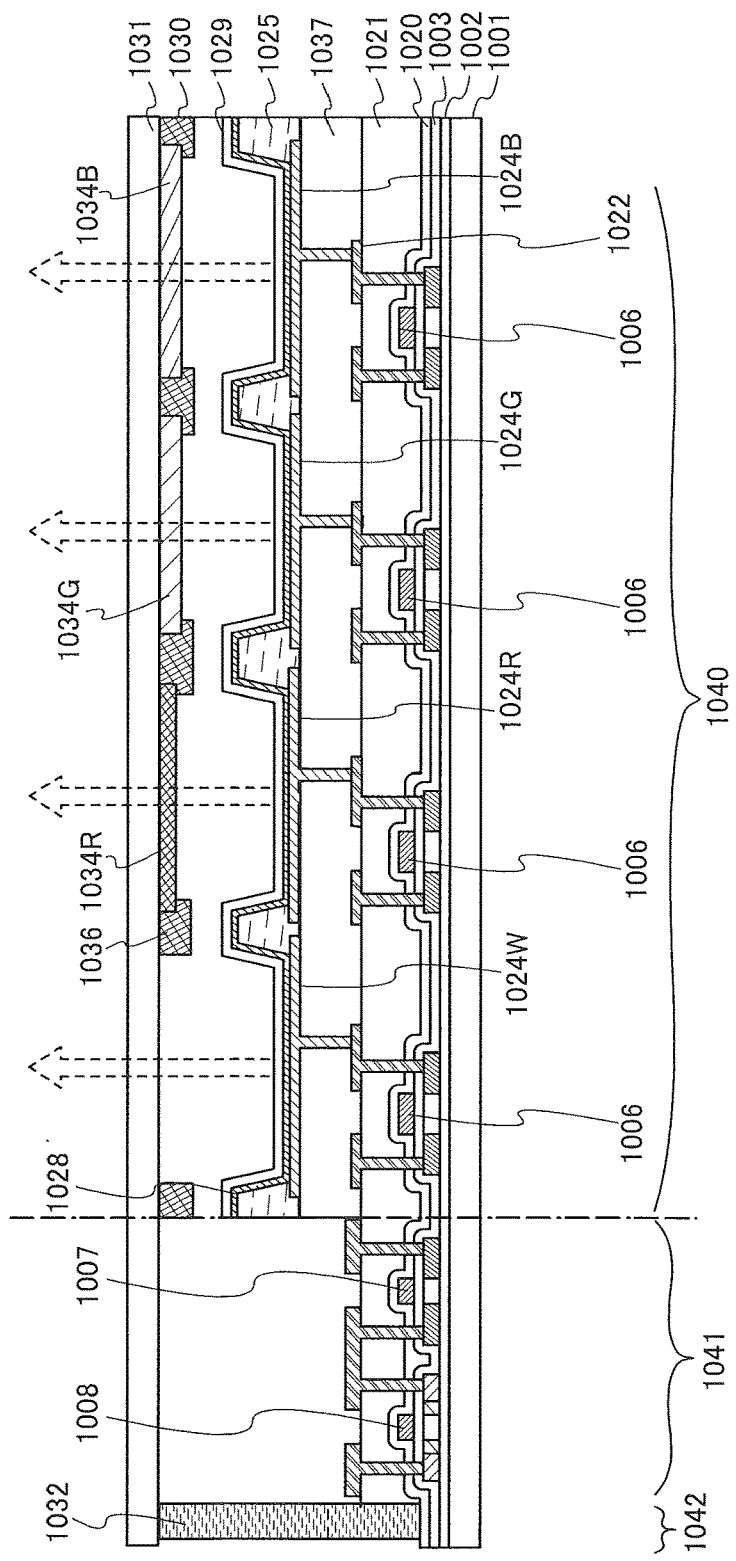
FIG. 4 is a conceptual diagram of an active matrix light-emitting device.

The above-described light-emitting device is a light-emitting device having a structure in which light is extracted from the substrate 1001 side where the TFTs are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any other known material.

The first electrodes 1024W, 1024R, 1024G, and 1024B of the light-emitting elements each function as an anode here, but may function as a cathode. Further, in the case of a light-emitting device having a top emission structure as illustrated in FIG. 4, the first electrodes are preferably reflective electrodes. The layer 1028 containing an organic compound is formed to have a structure similar to the structure of the layer 103 containing an organic compound, which is described in any of Embodiments 2 to 4, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) 1035 may be covered with the overcoat layer 1036. Note that a light-transmitting substrate is used as the sealing substrate 1031.

Further, although an example in which full color display is performed using four colors of red, green, blue, and white is shown here, there is no particular limitation and full color display using three colors of red, green, and blue may be performed.

The light-emitting device in this embodiment is manufactured using the light-emitting element described in any of Embodiments 2 to 4 and thus can have favorable characteristics. Specifically, since the light-emitting element described in any of Embodiments 2 to 4 has favorable emission efficiency, the light-emitting device can have reduced power consumption. In addition, light in desired wavelength ranges can be easily provided by the light-emitting element described in any of Embodiments 2 to 4, which makes it possible to provide a versatile light-emitting device.

Figure 5A:
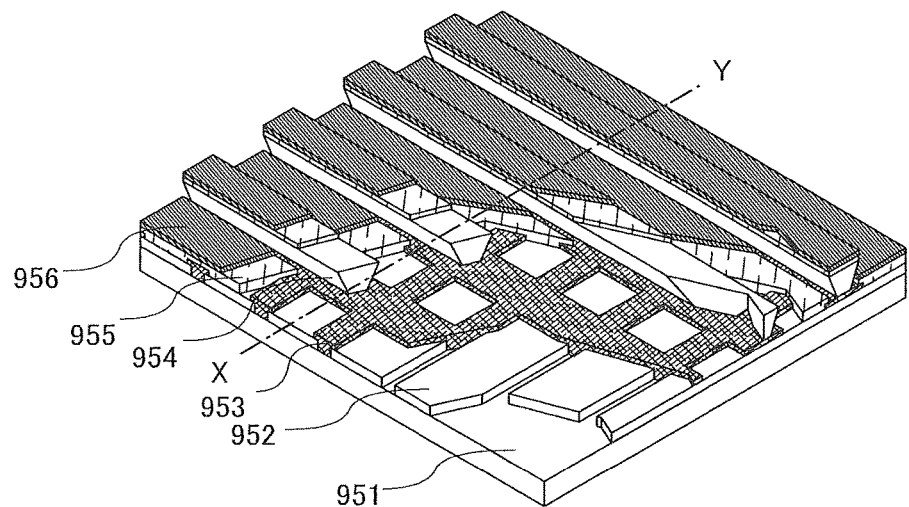
FIGS. 5A and 5B are conceptual diagrams of a passive matrix light-emitting device.
Figure 5B:
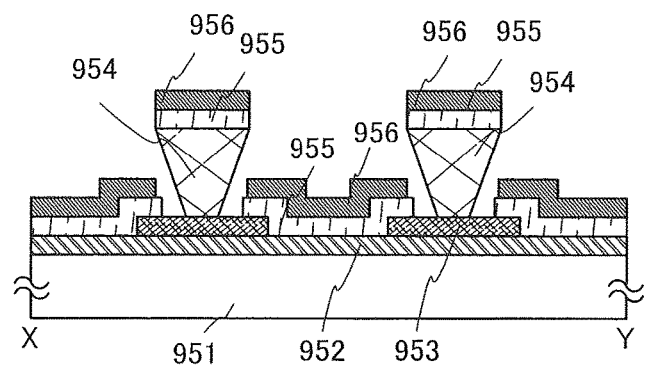

An active matrix light-emitting device is described above, whereas a passive matrix light-emitting device is described below. FIGS. 5A and 5B illustrate a passive matrix light-emitting device manufactured using the present invention. FIG. 5A is a perspective view of the light-emitting device, and FIG. 5B is a cross-sectional view of FIG. 5A taken along line X-Y. In FIGS. 5A and 5B, a layer 955 containing an organic compound is provided between an electrode 952 and an electrode 956 over a substrate 951. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953. The partition layer 954 thus provided can prevent defects in the light-emitting element due to static electricity or the like. Further, the passive matrix light-emitting device can also have lower power consumption by including the light-emitting element described in any of Embodiments 2 to 4, which has favorable emission efficiency. In addition, light in desired wavelength ranges can be easily provided by the light-emitting element described in any of Embodiments 2 to 4, which makes it possible to provide a versatile light-emitting device.

Since many minute light-emitting elements arranged in a matrix in the light-emitting device described above can each be controlled, the light-emitting device can be suitably used as a display device for displaying images.

This embodiment can be freely combined with any of other embodiments.

Embodiment 6

Figure 6A:
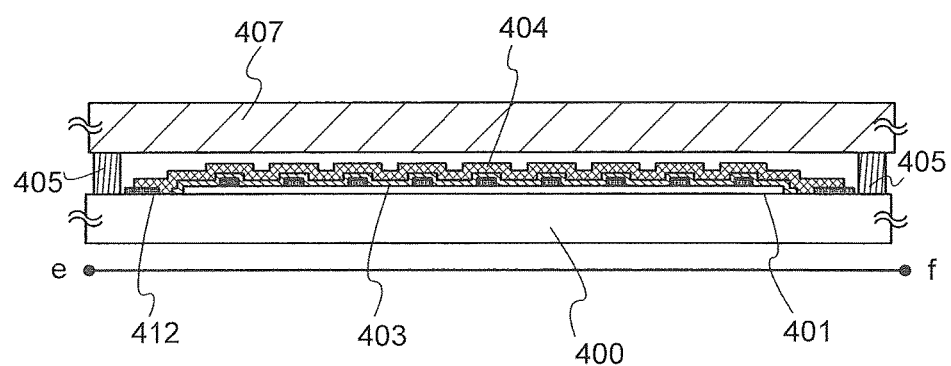
FIGS. 6A and 6B are conceptual diagrams of a lighting device.
Figure 6B:
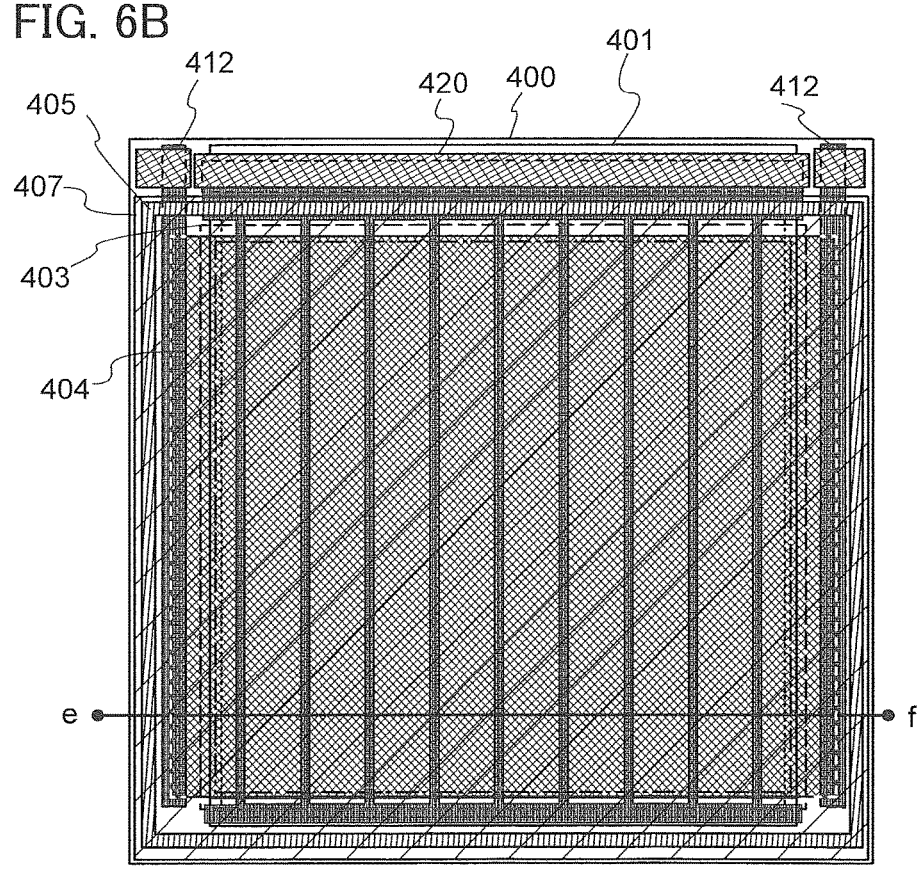

In this embodiment, an example in which the light-emitting element described in any of Embodiments 2 to 4 is used for a lighting device is described with reference to FIGS. 6A and 6B. FIG. 6B is a top view of the lighting device, and FIG. 6A is a cross-sectional view of FIG. 6B taken along line e-f.

In the lighting device in this embodiment, a first electrode 401 is formed over a substrate 400 which is a support and has a light-transmitting property. The first electrode 401 corresponds to the first electrode 101 in Embodiment 4. When light is extracted through the first electrode 401 side, the first electrode 401 is formed using a material having a light-transmitting property.

A pad 412 for applying voltage to a second electrode 404 is provided over the substrate 400.

A layer 403 containing an organic compound is formed over the first electrode 401. The structure of the layer 403 containing an organic compound corresponds to, for example, the structure of the layer 103 containing an organic compound in Embodiment 4, or the structure in which the light-emitting units 511 and 512 and the charge-generation layer 513 are combined. For these structures, the description in Embodiment 4 can be referred to.

The second electrode 404 is formed to cover the layer 403 containing an organic compound. The second electrode 404 corresponds to the second electrode 102 in Embodiment 4. The second electrode 404 is formed using a material having high reflectance when light is extracted through the first electrode 401 side. The second electrode 404 is connected to the pad 412, whereby voltage is applied thereto.

As described above, the lighting device described in this embodiment includes a light-emitting element including the first electrode 401, the layer 403 containing an organic compound, and the second electrode 404. Since the light-emitting element is inexpensive and excellent in durability, the lighting device in this embodiment can have high emission efficiency.

The light-emitting element having the above structure is fixed to a sealing substrate 407 with a sealing material 405 and sealing is performed, whereby the lighting device is completed. In addition, the sealing material 405 can be mixed with a desiccant which allows moisture to be adsorbed, increasing reliability.

When parts of the pad 412 and the first electrode 401 are extended to the outside of the sealing material 405, the extended parts can serve as external input terminals. An IC chip 420 mounted with a converter or the like may be provided over the external input terminals.

As described above, since the lighting device described in this embodiment includes the light-emitting element described in any of Embodiments 2 to 4, the lighting device can have high emission efficiency.

Embodiment 7

In this embodiment, examples of electronic devices each including the light-emitting element described in any of Embodiments 2 to 4 are described. The light-emitting element described in any of Embodiments 2 to 4 has high emission efficiency and accordingly, the electronic devices in this embodiment each of which includes the light-emitting element can have low power consumption.

Examples of the electronic device to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are described below.

Figure 7A:
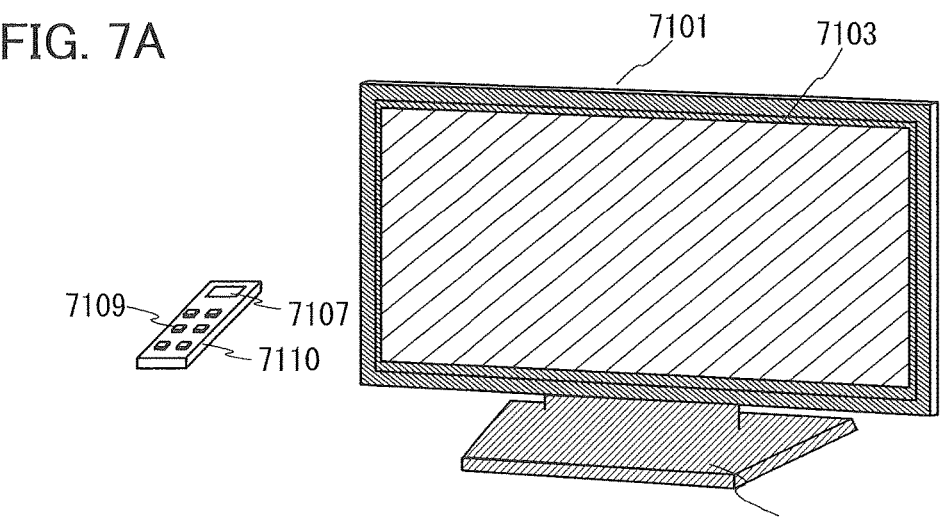
Figure 7A:
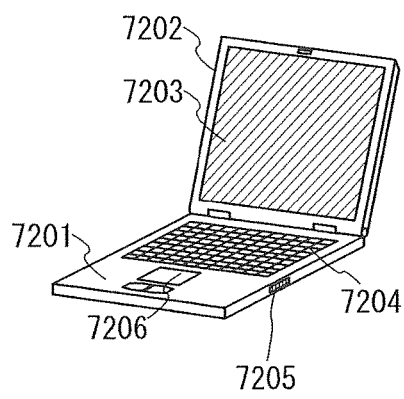
Figure 7A:
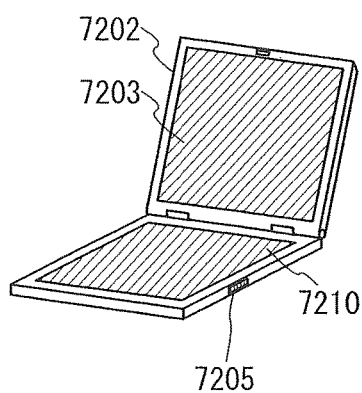

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements described in any of Embodiments 2 to 4 are arranged in a matrix. The light-emitting elements can have high emission efficiency. Therefore, the television device including the display portion 7103 which is formed using the light-emitting element can have low power consumption.

The television device can be operated with an operation switch of the housing 7101 or a separate remote controller 7110. With operation keys 7109 of the remote controller 7110, channels and volume can be controlled and images displayed on the display portion 7103 can be controlled. Further, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured using light-emitting elements arranged in a matrix in the display portion 7203, which are the same as that described in any of Embodiments 2 to 4. The computer illustrated in FIG. 7B1 may have a structure illustrated in FIG. 7B2. The computer illustrated in FIG. 7B2 is provided with a second display portion 7210 instead of the keyboard 7204 and the pointing device 7206. The second display portion 7210 is a touchscreen, and input can be performed by operation of display for input on the second display portion 7210 with a finger or a dedicated pen. The second display portion 7210 can also display images other than the display for input. The display portion 7203 may also be a touchscreen. Connecting the two screens with a hinge can prevent troubles; for example, the screens can be prevented from being cracked or broken while the computer is being stored or carried. Note that this computer is manufactured using light-emitting elements arranged in a matrix in the display portion 7203, which are the same as that described in any of Embodiments 2 to 4. Therefore, this computer having the display portion 7203 which is formed using the light-emitting elements consumes less power.

Figure 7C:
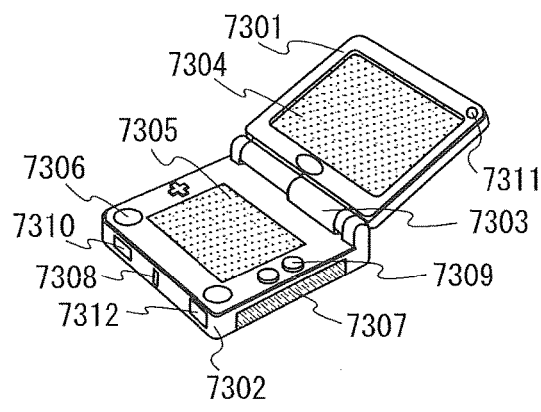

FIG. 7C illustrates a portable game machine, which includes two housings, a housing 7301 and a housing 7302, which are connected with a joint portion 7303 so that the portable game machine can be opened or folded. The housing 7301 incorporates a display portion 7304 including the light-emitting elements each of which is described in any of Embodiments 2 to 4 and which are arranged in a matrix, and the housing 7302 incorporates a display portion 7305. In addition, the portable game machine illustrated in FIG. 7C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion including the light-emitting elements each of which is described in any of Embodiments 2 to 4 and which are arranged in a matrix is used as at least either the display portion 7304 or the display portion 7305, or both, and the structure can include other accessories as appropriate. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above. The portable game machine having the display portion 7304 can have low power consumption because the light-emitting element described in any of Embodiments 2 to 4 is used in the display portion 7304.

Figure 7D:
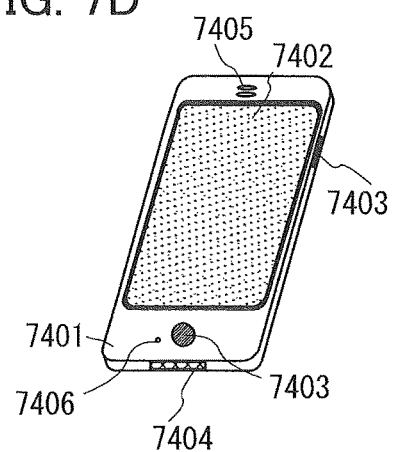

FIG. 7D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone has the display portion 7402 including the light-emitting elements each of which is described in any of Embodiments 2 to 4 and which are arranged in a matrix. Accordingly, the mobile phone can have low power consumption.

When the display portion 7402 of the mobile phone illustrated in FIG. 7D is touched with a finger or the like, data can be input into the mobile phone. In this case, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device which includes a sensor for detecting inclination, such as a gyroscope or an acceleration sensor, is provided inside the mobile phone, the direction of the mobile phone (whether the mobile phone is placed horizontally or vertically for a landscape mode or a portrait mode) is determined so that display on the screen of the display portion 7402 can be automatically switched.

The screen modes are switched by touching the display portion 7402 or operating the operation buttons 7403 of the housing 7401. Alternatively, the screen modes can be switched depending on the kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 8:
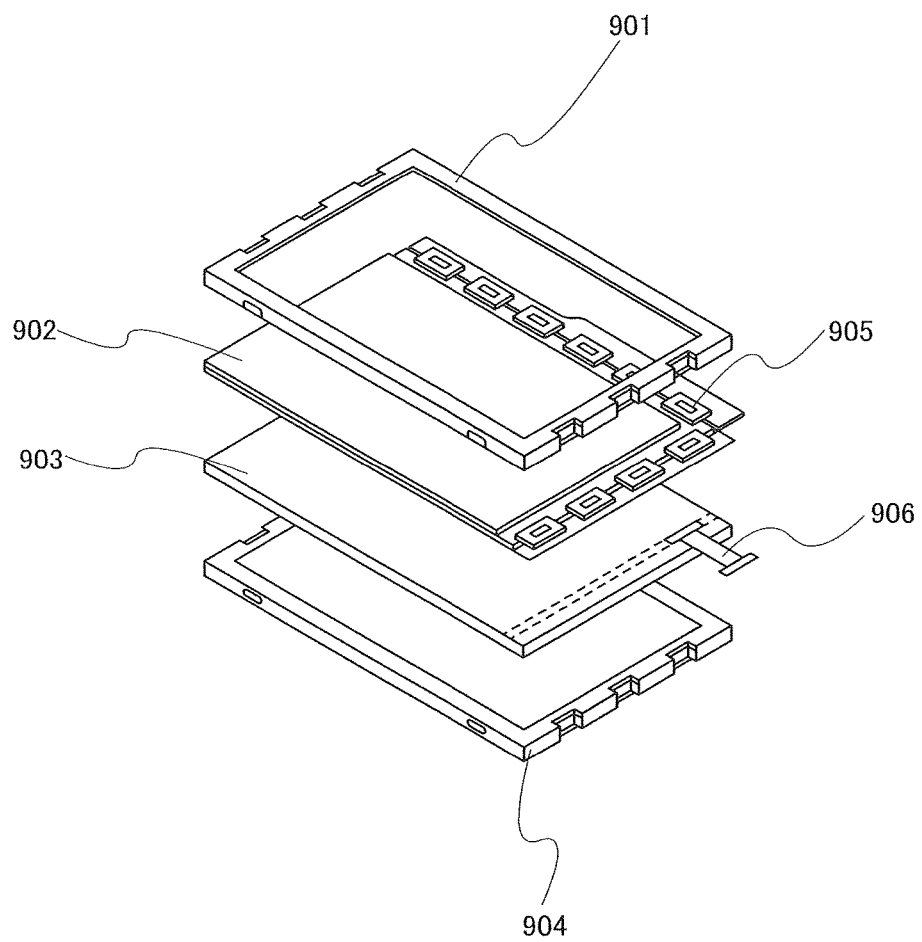
FIG. 8 illustrates an electronic device.

FIG. 8 illustrates an example of a liquid crystal display device using the light-emitting element described in any of Embodiments 2 to 4 for a backlight. The liquid crystal display device shown in FIG. 8 includes a housing 901, a liquid crystal layer 902, a backlight unit 903, and a housing 904. The liquid crystal layer 902 is connected to a driver IC 905. The light-emitting element described in any of Embodiments 2 to 4 is used for the backlight unit 903, to which current is supplied through a terminal 906.

The light-emitting element described in any of Embodiments 2 to 4 is used for the backlight of the liquid crystal display device; thus, the backlight can have reduced power consumption. In addition, the use of the light-emitting element described in any of Embodiments 2 to 4 enables manufacture of a planar-emission lighting device and further a larger-area planar-emission lighting device; therefore, the backlight can be a larger-area backlight, and the liquid crystal display device can also be a larger-area device. Furthermore, the light-emitting device using the light-emitting element described in any of Embodiments 2 to 4 can be thinner than a conventional one; accordingly, the display device can also be thinner.

Figure 9:
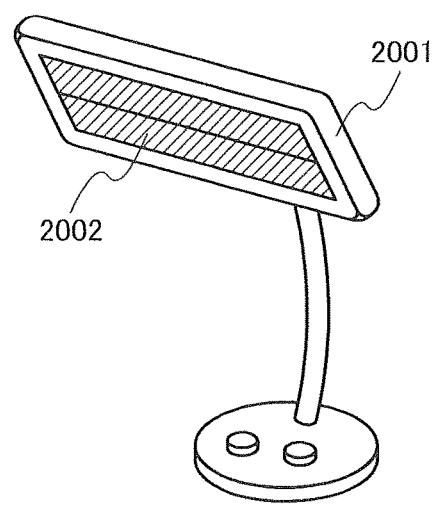
FIG. 9 illustrates a lighting device.

FIG. 9 illustrates an example in which the light-emitting element described in any of Embodiments 2 to 4 is used for a table lamp which is a lighting device. The table lamp illustrated in FIG. 9 includes a housing 2001 and a light source 2002, and the lighting device described in Embodiment 6 is used for the light source 2002.

Figure 10:
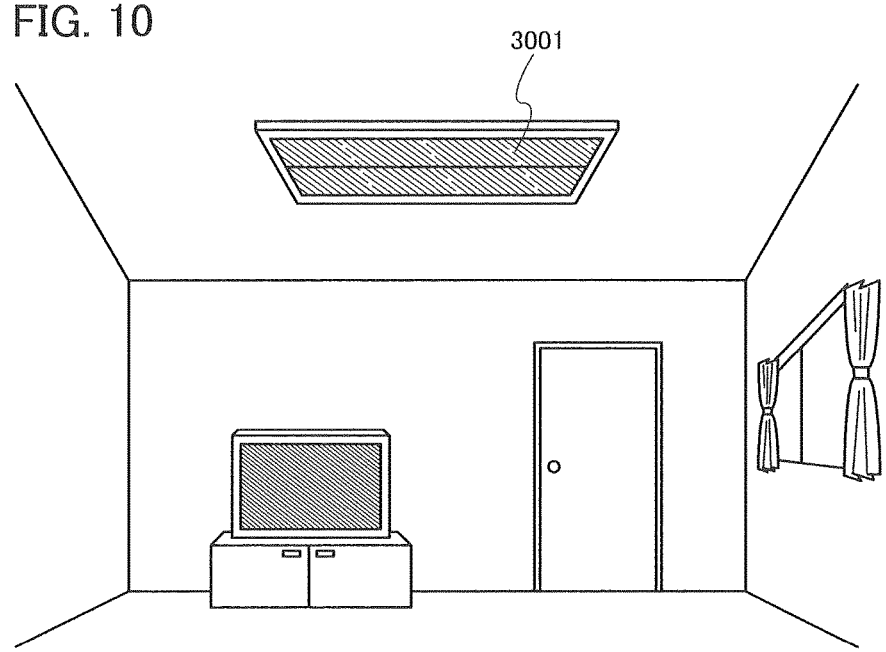
FIG. 10 illustrates a lighting device.

FIG. 10 illustrates an example in which the light-emitting element described in any of Embodiments 2 to 4 is used for an indoor lighting device 3001. Since the light-emitting element described in any of Embodiments 2 to 4 has low power consumption, a lighting device having low power consumption can be obtained. Further, since the light-emitting element described in any of Embodiments 2 to 4 can have a large area, the light-emitting element can be used for a large-area lighting device. Furthermore, since the light-emitting element described in any of Embodiments 2 to 4 is thin, the light-emitting element can be used for a lighting device having a reduced thickness.

Figure 11:
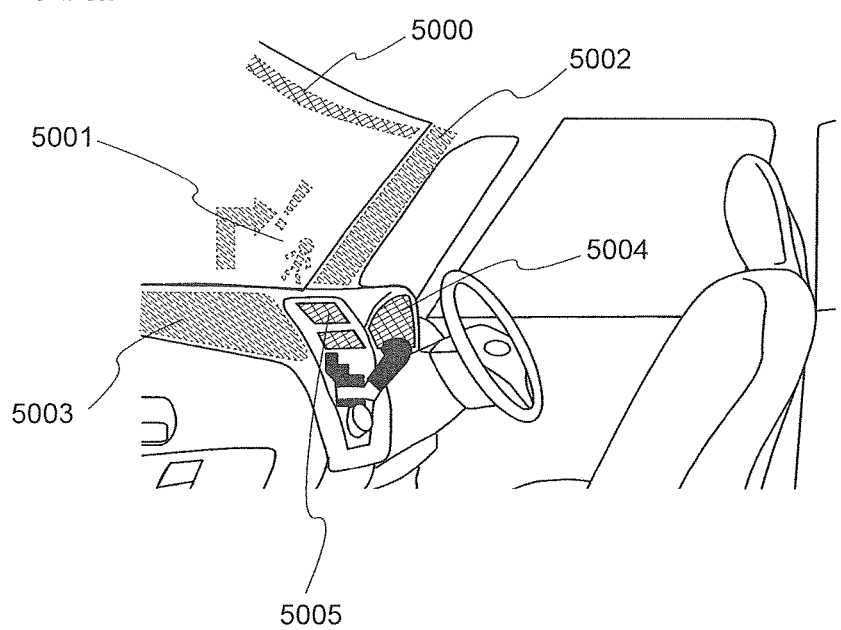
FIG. 11 illustrates in-vehicle display devices and lighting devices.

The light-emitting element described in any of Embodiments 2 to 4 can also be used for an automobile windshield or an automobile dashboard. FIG. 11 illustrates one mode in which the light-emitting element described in any of Embodiments 2 to 4 is used for an automobile windshield and an automobile dashboard. Display regions 5000 to 5005 each include the light-emitting element described in any of Embodiments 2 to 4.

The display regions 5000 and the display region 5001 display devices which are provided in the automobile windshield and in which the light-emitting elements described in any of Embodiments 2 to 4 are incorporated. The light-emitting element described in any of Embodiments 2 to 4 can be formed into what is called a see-through display device, through which the opposite side can be seen, by including a first electrode and a second electrode formed of electrodes having light-transmitting properties. Such see-through display devices can be provided even in the automobile windshield, without hindering the vision. Note that in the case where a transistor for driving or the like is provided, a transistor having a light-transmitting property, such as an organic transistor using an organic semiconductor material or a transistor using an oxide semiconductor, is preferably used.

A display device incorporating the light-emitting element described in any of Embodiments 2 to 4 is provided in the display region 5002 in a pillar portion. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Further, such information can also be shown by the display regions 5000 to 5003. Note that the display regions 5000 to 5005 can also be used as lighting devices.

The light-emitting element described in any of Embodiments 2 to 4 can have low power consumption.

For that reason, load on a battery is small even when a number of large screens such as the display regions 5000 to 5005 are provided, which provides comfortable use. For that reason, the light-emitting device and the lighting device each of which includes the light-emitting element described in any of Embodiments 2 to 4 can be suitably used as an in-vehicle light-emitting device and an in-vehicle lighting device.

Figure 12A:
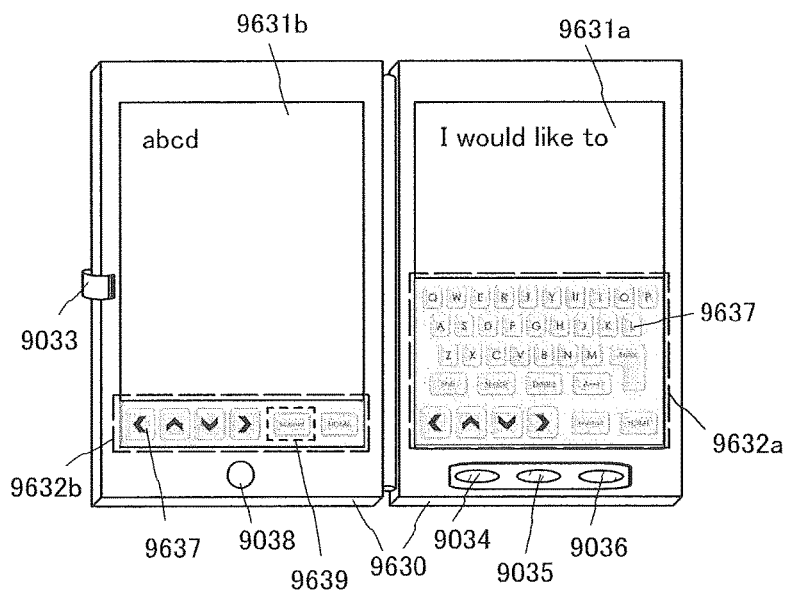
FIGS. 12A to 12C illustrate an electronic device.
Figure 12B:
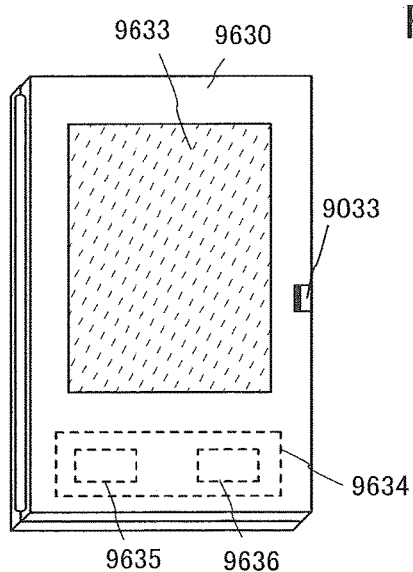

FIGS. 12A and 12B illustrate an example of a foldable tablet terminal. The tablet terminal is opened in FIG. 12A. The tablet terminal includes a housing 9630, a display portion 9631a, a display portion 9631b, a display mode switch 9034, a power switch 9035, a power saver switch 9036, a clasp 9033, and an operation switch 9038. Note that in the tablet terminal, one or both of the display portion 9631a and the display portion 9631b is/are formed using a light-emitting device which includes the light-emitting element described in any of Embodiments 2 to 4.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard can be displayed on the entire region of the display portion 9631a so that the display portion 9631a is used as a touchscreen, and the display portion 9631b can be used as a display screen.

Like the display portion 9631a, part of the display portion 9631b can be a touchscreen region 9632b. A switching button 9639 for showing/hiding a keyboard of the touchscreen is touched with a finger, a stylus, or the like, so that keyboard buttons can be displayed on the display portion 9631b.

Touch input can be performed in the touchscreen region 9632a and the touchscreen region 9632b at the same time.

The display mode switch 9034 can switch the display between portrait mode, landscape mode, and the like, and between monochrome display and color display, for example. With the power saver switch 9036, the luminance of display can be optimized in accordance with the amount of external light at the time when the tablet terminal is in use, which is detected with an optical sensor incorporated in the tablet terminal. The tablet terminal may include another detection device such as a sensor for detecting orientation (e.g., a gyroscope or an acceleration sensor) in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, one of them may be a display panel that can display higher-definition images than the other.

The tablet terminal is folded in FIG. 12B. The tablet terminal includes the housing 9630, a solar cell 9633, a charge and discharge control circuit 9634, a battery 9635, and a DC-to-DC converter 9636. Note that FIG. 12B illustrates an example in which the charge and discharge control circuit 9634 includes the battery 9635 and the DC-to-DC converter 9636.

Since the tablet terminal can be folded, the housing 9630 can be closed when not in use. Thus, the display portions 9631a and 9631b can be protected, thereby providing a tablet terminal with high endurance and high reliability for long-term use.

In addition, the tablet terminal illustrated in FIGS. 12A and 12B can have a function of displaying various kinds of information (e.g., a still image, a moving image, and a text image) on the display portion, a function of displaying a calendar, the date, the time, or the like on the display portion, a touch input function of operating or editing information displayed on the display portion by touch input, a function of controlling processing by various kinds of software (programs), and the like.

The solar cell 9633, which is attached on the surface of the tablet terminal, supplies electric power to a touchscreen, a display portion, an image signal processor, and the like. Note that the solar cell 9633 is preferably provided on one or two surfaces of the housing 9630, in which case the battery 9635 can be charged efficiently.

Figure 12C:
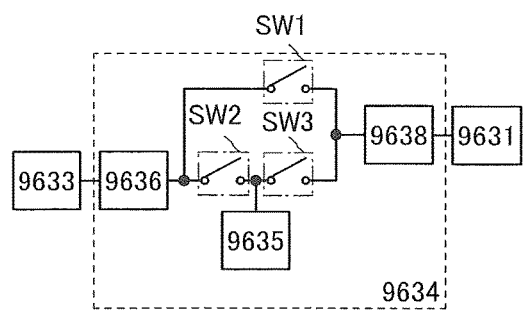

The structure and operation of the charge and discharge control circuit 9634 illustrated in FIG. 12B are described with reference to a block diagram of FIG. 12C. FIG. 12C shows the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 in FIG. 12B.

First, an example of operation in the case where power is generated by the solar cell 9633 using external light is described. The voltage of power generated by the solar cell is raised or lowered by the DC-to-DC converter 9636 so that the power has voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. In addition, when display on the display portion 9631 is not performed, the switch SW1 is turned off and a switch SW2 is turned on so that charge of the battery 9635 may be performed.

Although the solar cell 9633 is described as an example of a power generation unit, the power generation unit is not particularly limited, and the battery 9635 may be charged by another power generation unit such as a piezoelectric element or a thermoelectric conversion element (Peltier element). The battery 9635 may be charged by a non-contact power transmission module which is capable of charging by transmitting and receiving power by wireless (without contact), or any of the other charge unit used in combination, and the power generation unit is not necessarily provided.

One embodiment of the present invention is not limited to the tablet terminal having the shape illustrated in FIGS. 12A to 12C as long as the display portion 9631 is included.

Note that the structure described in this embodiment can be combined with any of the structures described in Embodiments 1 to 6 as appropriate.

As described above, the application range of the light-emitting element described in any of Embodiments 2 to 4 is so wide that this light-emitting element can be applied to electronic devices in a variety of fields. By using the light-emitting element described in any of Embodiments 2 to 4, an electronic device having low power consumption can be obtained.

Example 1

In this example, a method for synthesizing N-(1,1'-biphenyl-4-yl)-N-[4-(dibenzofuran-4-yl)phenyl]-9,9-dimethyl-9H-fluoren-2-amine (abbreviation: FrBBiF-II) represented by Structural Formula (100) will be described.

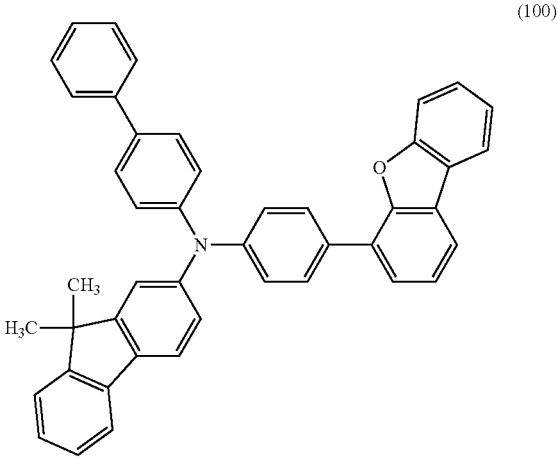 [SMILES: CC1(C)c2ccccc2-c2ccc(N(c3ccc(-c4ccccc4)cc3)c3ccc(-c4cccc5c4oc4ccccc45)cc3)cc21]

First, 2.1 g (6.6 mmol) of 4-(4-bromophenyl)dibenzofuran, 2.4 g (6.7 mmol) of N-(1,1'-biphenyl-4-yl)-9,9-dimethyl-9H-fluoren-2-amine, and 1.9 g (20 mmol) of sodium tert-butoxide were put in a 200-mL three-neck flask and the air in the flask was replaced with nitrogen. To this mixture, 33 mL of toluene, 0.30 mL of a 10% hexane solution of tri(tert-butyl)phosphine, and 48 mg (0.1 mmol) of bis(dibenzylideneacetone)palladium(0) were added, and stirring was performed at 90° C. for 7.5 hours. After the stirring, suction filtration through Florisil (produced by Wako Pure Chemical Industries, Ltd., Catalog No. 540-00135), Celite (produced by Wako Pure Chemical Industries, Ltd., Catalog No. 531-16855), and alumina was carried out to give a filtrate. The filtrate was concentrated to give a solid. The solid was purified by silica gel column chromatography (the developing solvent was hexane and toluene in a ratio of 3:1) to give a solid. The solid was recrystallized from toluene and hexane, so that 3.2 g of an objective solid was obtained in a yield of 81%. A reaction scheme of this reaction is shown below.

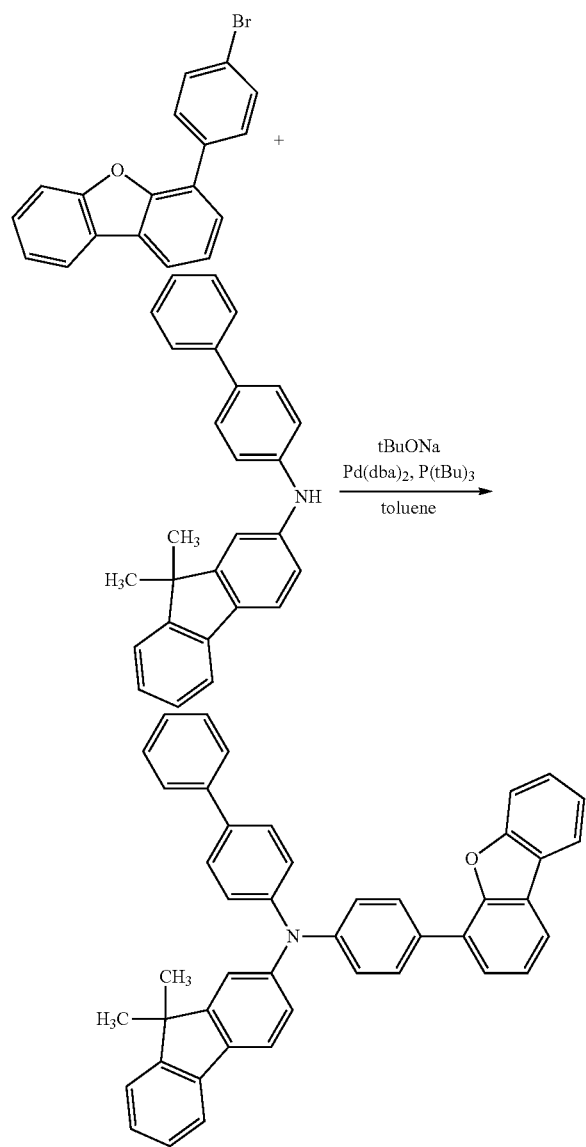

Using a train sublimation method, 1.0 g of the obtained solid was purified by sublimation. In the purification by sublimation, the pressure was 2.6 Pa, the flow rate of argon gas was 5.0 mL/min, and the temperature of the heating was 289° C. After the purification by sublimation, 0.99 g of a solid which was the object of the synthesis was obtained at a collection rate of 95%.

Results of measurement of the obtained solid by nuclear magnetic resonance ($^1$H NMR) are shown below.

$^1$H NMR (CDCl$_3$, 500 MHz): δ=1.46 (s, 6H), 7.18 (dd, J=8.5 Hz, 2.5 Hz, 1H), 7.26-7.48 (m, 14H), 7.53-7.56 (m, 2H), 7.60-7.68 (m, 6H), 7.86-7.91 (m, 3H), 7.99 (d, J=7.5 Hz, 1H).

Thermogravimetry-differential thermal analysis (TG-DTA) of the obtained FrBBiF-II was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 393° C., which is indicative of high heat resistance.

Figure 13A:
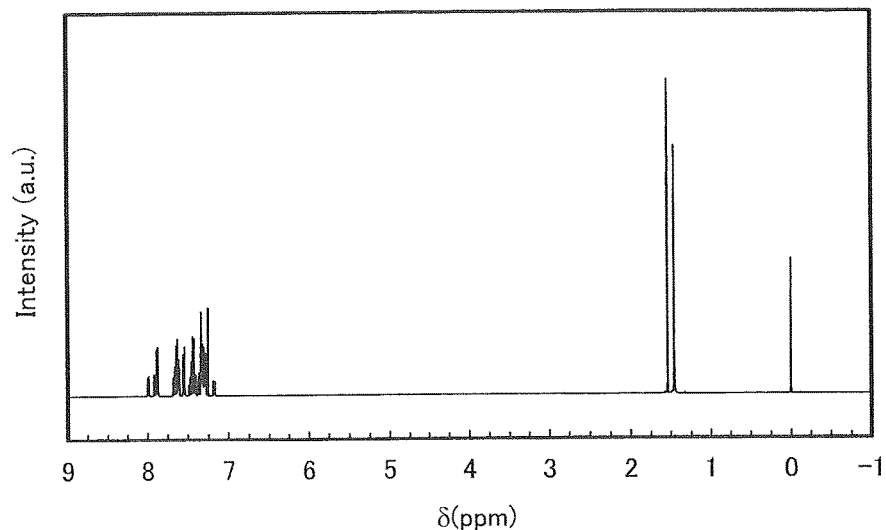
FIGS. 13A and 13B are NMR charts of FrBBiF-II.
Figure 13B:
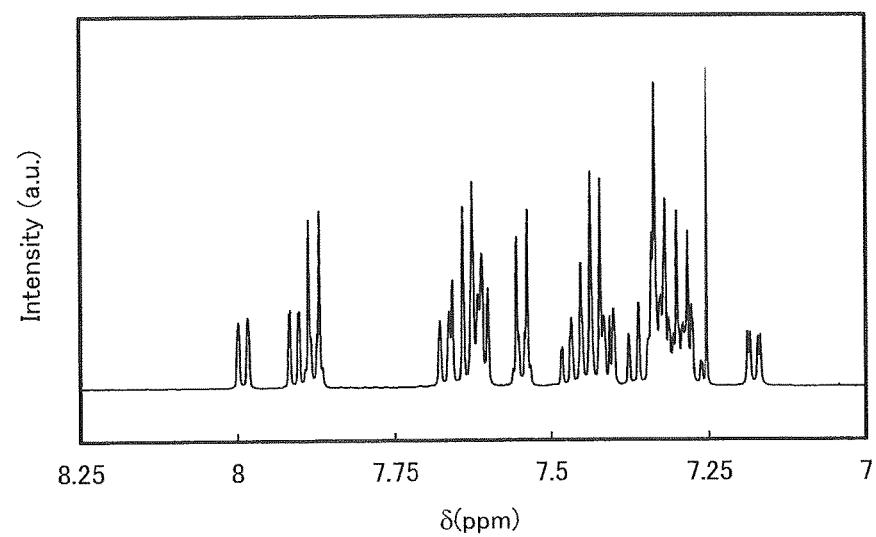

FIGS. 13A and 13B are NMR charts. Note that FIG. 13B shows an enlarged part of FIG. 13A in the range of 7.00 ppm to 8.25 ppm. The measurement results confirmed that N-(1,1'-biphenyl-4-yl)-N-[4-(dibenzofuran-4-yl)phenyl]-9,9-dimethyl-9H-fluoren-2-amine (abbreviation: FrBBiF-II), which was the target substance, was obtained.

<<Physical Properties of FrBBiF-II>>

Figure 14A:
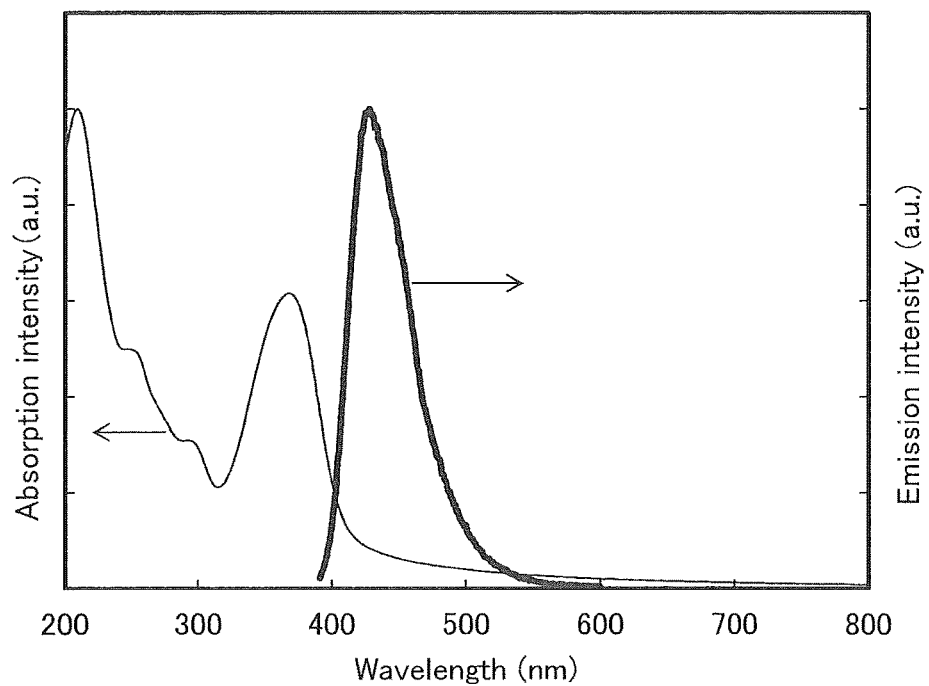
FIGS. 14A and 14B show absorption spectra and emission spectra of FrBBiF-II.
Figure 14B:
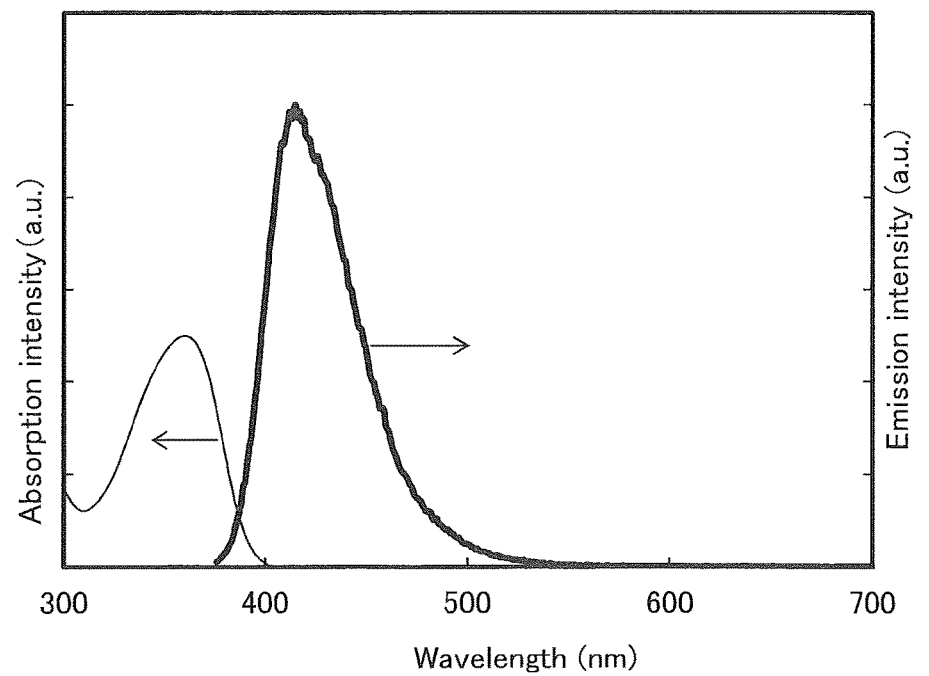

FIG. 14A shows an absorption spectrum and an emission spectrum of FrBBiF-II in a toluene solution of FrBBiF-II, and FIG. 14B shows an absorption spectrum and an emission spectrum of a thin film of FrBBiF-II. The spectra were measured with a UV-visible spectrophotometer (V550, produced by JASCO Corporation). The spectra of FrBBiF-II in the toluene solution of FrBBiF-II were measured with a toluene solution of FrBBiF-II put in a quartz cell. The spectra of the thin film were measured with a sample prepared by deposition of FrBBiF-II on a quartz substrate by evaporation. Note that in the case of the absorption spectrum of FrBBiF-II in the toluene solution of FrBBiF-II, the absorption spectrum obtained by subtraction of the absorption spectra of the quartz cell and toluene from the measured spectra is shown in the drawing and that in the case of the absorption spectrum of the thin film of FrBBiF-II, the absorption spectrum obtained by subtraction of the absorption spectrum of the quartz substrate from the measured spectra is shown in the drawing.

As shown in FIG. 14A, in the case of FrBBiF-II in the toluene solution, an absorption peak was observed at approximately 360 nm, and an emission wavelength peak was observed at approximately 415 nm (excitation wavelength: 366 nm). As shown in FIG. 14B, in the case of the thin film of FrBBiF-II, absorption peaks were observed at approximately 368 nm, 294 nm, 266 nm, 247 nm, and 209 nm, and an emission wavelength peak was observed at approximately 428 nm (excitation wavelength: 376 nm). Thus, it was found that absorption and light emission of FrBBiF-II occur in extremely short wavelength regions.

The ionization potential of FrBBiF-II in a thin film state was measured by photoelectron spectroscopy (the measuring instrument: AC-2, manufactured by Riken Keiki, Co., Ltd.) in the air. The obtained value of the ionization potential was converted into a negative value, so that the HOMO level of FrBBiF-II was determined to be −5.61 eV. From the data of the absorption spectrum of the thin film in FIG. 14B, the absorption edge of FrBBiF-II, which was obtained from Tauc plot with an assumption of direct transition, was 3.11 eV. Therefore, the optical energy gap of FrBBiF-II in a solid state was estimated at 3.11 eV; from the values of the HOMO level obtained above and this energy gap, the LUMO level of FrBBiF-II was estimated at −2.50 eV. This reveals that FrBBiF-II in the solid state has an energy gap as wide as 3.11 eV.

Furthermore, FrBBiF-II was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode.

Figure 15:
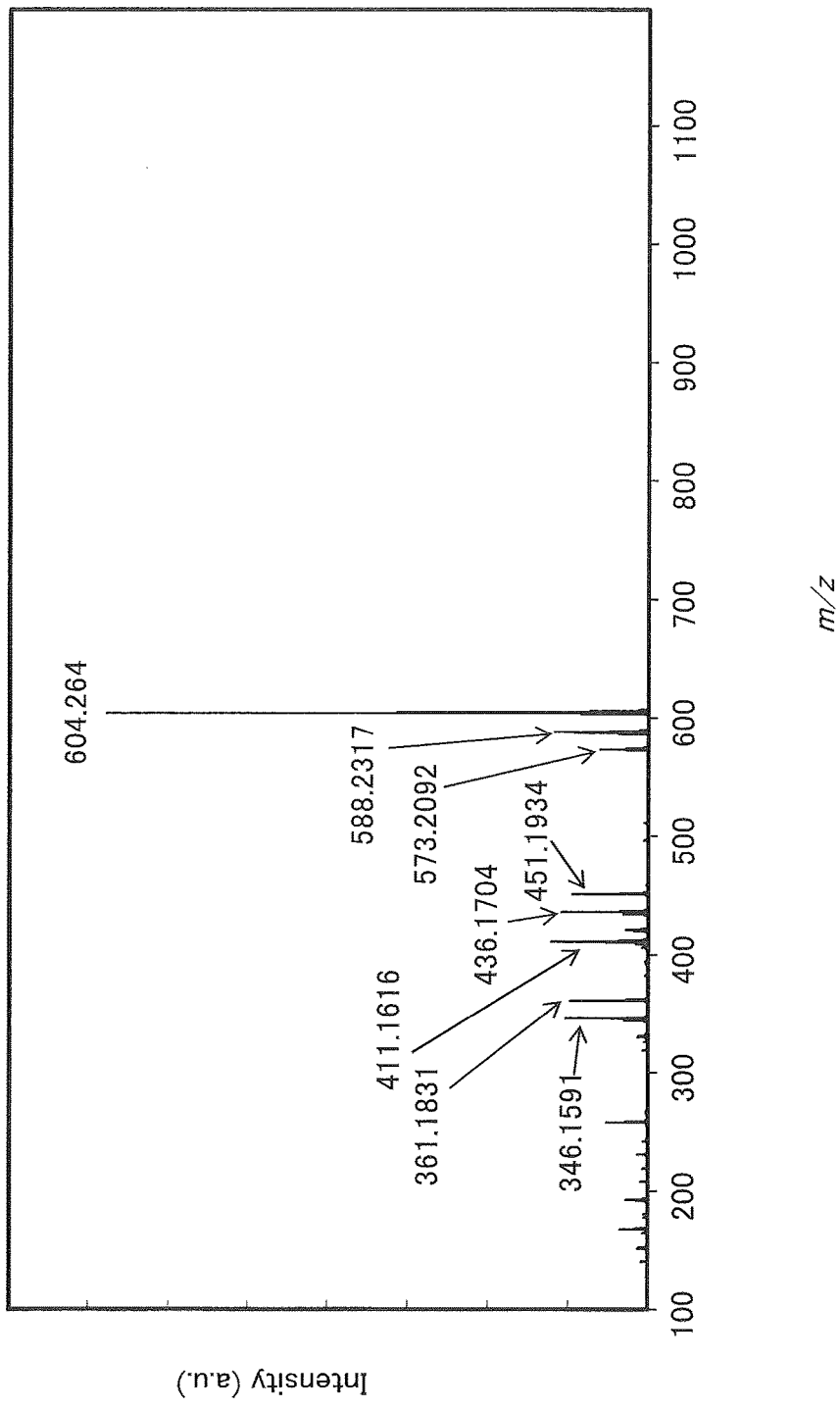
FIG. 15 shows results of LC/MS analysis of FrBBiF-II.

A component which underwent the ionization under the above-mentioned conditions was collided with an argon gas in a collision cell to dissociate into product ions. Energy (collision energy) for the collision with argon was 50 eV. A mass range for the measurement was m/z=100 to 1200. FIG. 15 shows the results.

Example 2

In this example, the light-emitting element (a light-emitting element 1) described in Embodiment 2 will be described. Note that in the light-emitting element 1, N-(1,1'-biphenyl-4-yl)-N-[4-(dibenzofuran-4-yl)phenyl]-9,9-dimethyl-9H-fluoren-2-amine (abbreviation: FrBBiF-II), which is the organic compound described in Embodiment 1, was used as the second organic compound in the light-emitting layer 113, and 4,6-bis[3-(9H-carbazol-9-yl)phenyl]pyrimidine (abbreviation: 4,6mCzP2Pm) was used as the first organic compound. Chemical formulae of materials used in this example are shown below.

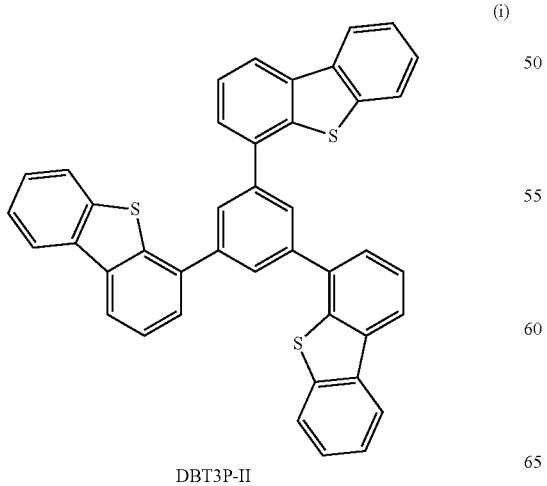

DBT3P-II (i)

-continued

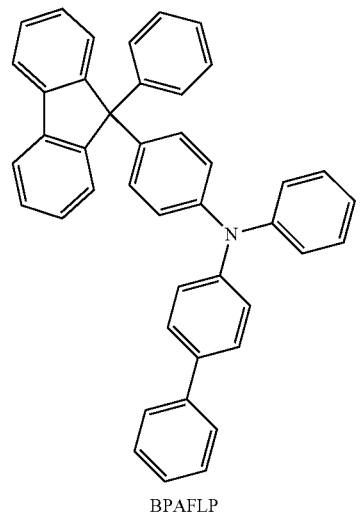

BPAFLP (ii)

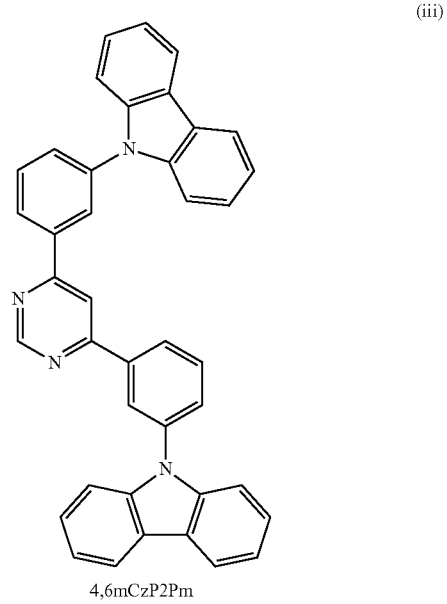

4,6mCzP2Pm (iii)

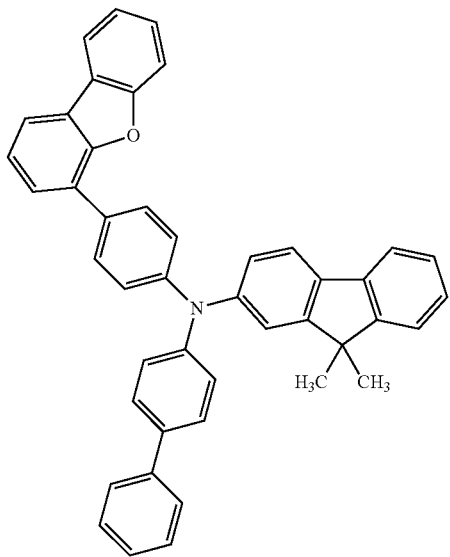

FrBBiF-II (100)

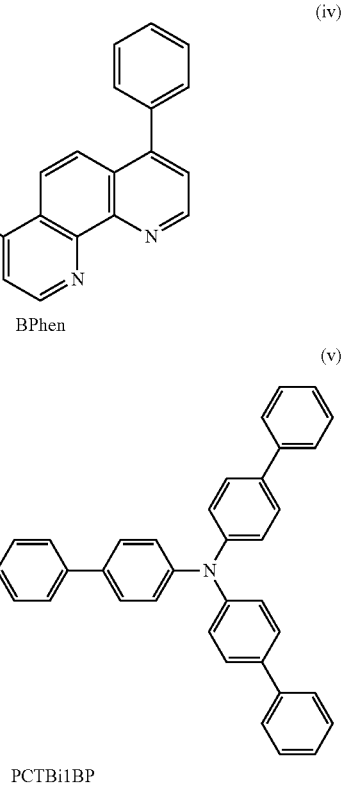

BPhen (iv)

PCTBi1BP (v)

(Method for Fabricating Light-Emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to approximately $10^{-4}$ Pa. After that, over the first electrode 101, 4,4',4''-(benzene-1,3,5-triyl)tri(dibenzothiophene) (abbreviation: DBT3P-II) represented by Structural Formula (i) and molybdenum(VI) oxide were deposited by co-evaporation by an evaporation method using resistance heating, so that the hole-injection layer 111 was formed. The thickness of the hole-injection layer 111 was set to 20 nm, and the weight ratio of DBT3P-II to molybdenum oxide was adjusted to 4:2. Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) which is represented by Structural Formula (ii) was formed to a thickness of 20 nm over the hole-injection layer 111 to form the hole-transport layer 112.

Further, over the hole-transport layer 112, 4,6-bis[3-(9H-carbazol-9-yl)phenyl]pyrimidine (abbreviation: 4,6mCzP2Pm) represented by Structural Formula (iii) and N-(1,1'-biphenyl-4-yl)-N-[4-(dibenzofuran-4-yl)phenyl]-9,9-dimethyl-9H-fluoren-2-amine (abbreviation: FrBBiF-II) represented by Structural Formula (100) were deposited by co-evaporation to a thickness of 40 nm such that the weight ratio of 4,6mCzP2Pm to FrBBiF-II was 0.8:0.2, whereby the light-emitting layer 113 was formed.

Then, the electron-transport layer 114 was formed over the light-emitting layer 113 in such a way that a 15 nm thick film of 4,6mCzP2Pm was formed and a 15 nm thick film of bathophenanthroline (abbreviation: BPhen) represented by Structural Formula (iv) was formed.

After the formation of the electron-transport layer 114, lithium fluoride (LiF) was deposited by evaporation to a thickness of 1 nm, so that the electron-injection layer 115 was formed. Lastly, aluminum was deposited by evaporation to a thickness of 200 nm to form the second electrode 102 functioning as a cathode. Thus, the light-emitting element 1 in this example was fabricated.

Note that in all the above evaporation steps, evaporation was performed by a resistance-heating method.

(Method for Fabricating Comparative Light-Emitting Element 1)

A comparative light-emitting element 1 was fabricated in a manner similar to that of the light-emitting element 1 except that FrBBiF-II was replaced with bis(biphenyl-4-yl)[4'-(9-phenyl-9H-carbazol-3-yl)biphenyl-4-yl]amine (abbreviation: PCTBi1BP) represented by Structural Formula (v) and the thickness of the film of Bphen was set to 10 nm.

The light-emitting element 1 and the comparative light-emitting element 1 were each sealed using a glass substrate in a glove box containing a nitrogen atmosphere so as not to be exposed to the air (specifically, a sealing material was applied onto an outer edge of the element and heat treatment was performed at 80° C. for 1 hour at the time of sealing). Then, initial characteristics of these light-emitting elements were measured. Note that the measurements were carried out at room temperature (in an atmosphere kept at 25° C.).

Figure 16:
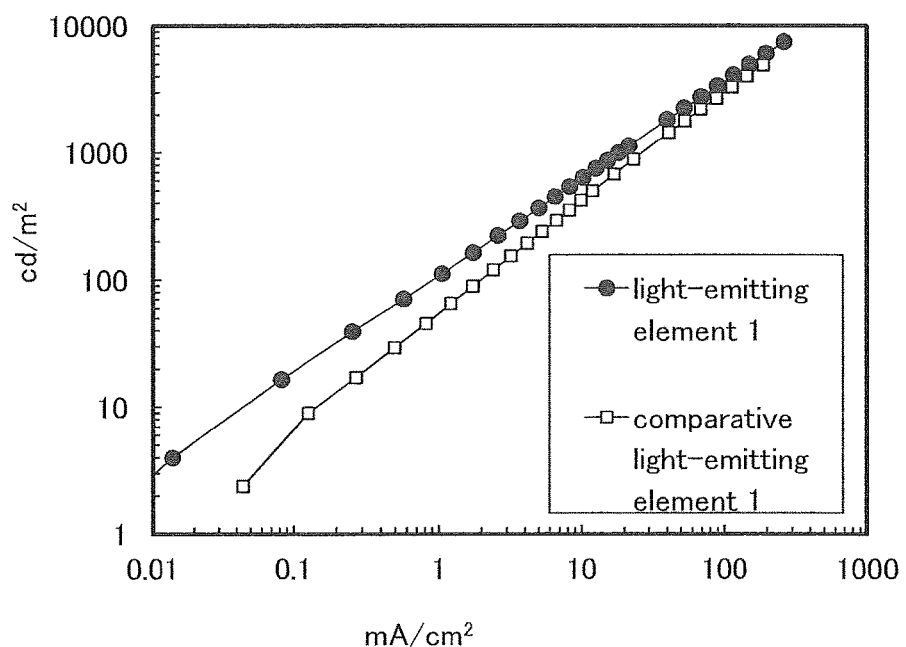
FIG. 16 shows current density-luminance characteristics of a light-emitting element 1 and a comparative light-emitting element 1.
Figure 17:
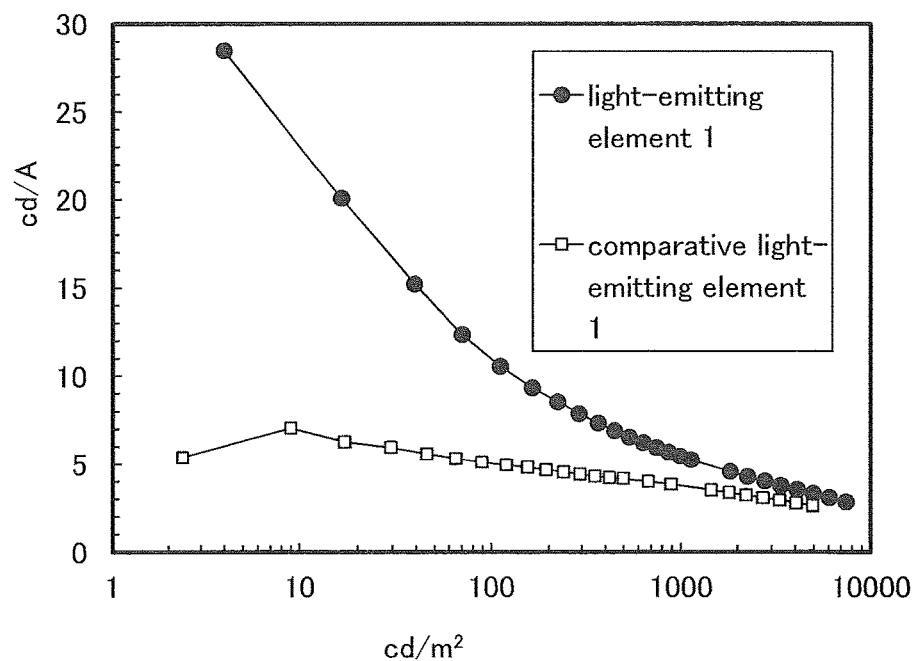
FIG. 17 shows luminance-current efficiency characteristics of a light-emitting element 1 and a comparative light-emitting element 1.
Figure 18:
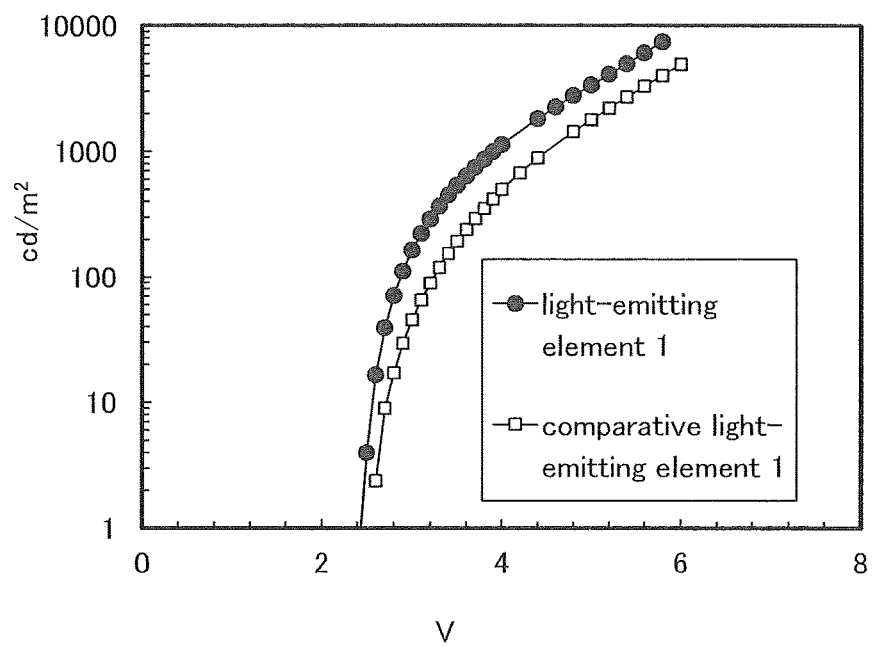
FIG. 18 shows voltage-luminance characteristics of a light-emitting element 1 and a comparative light-emitting element 1.
Figure 19:
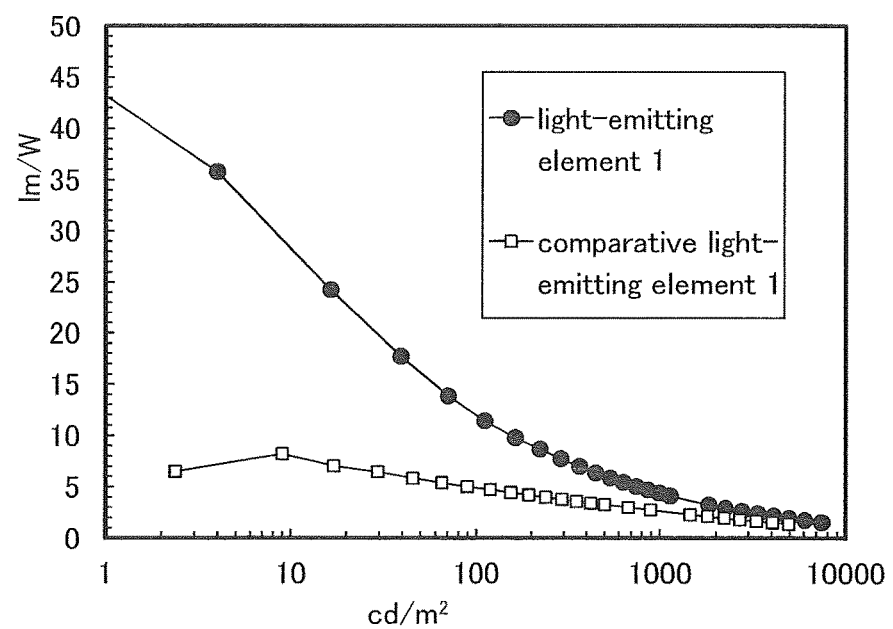
FIG. 19 shows luminance-power efficiency characteristics of a light-emitting element 1 and a comparative light-emitting element 1.
Figure 20:
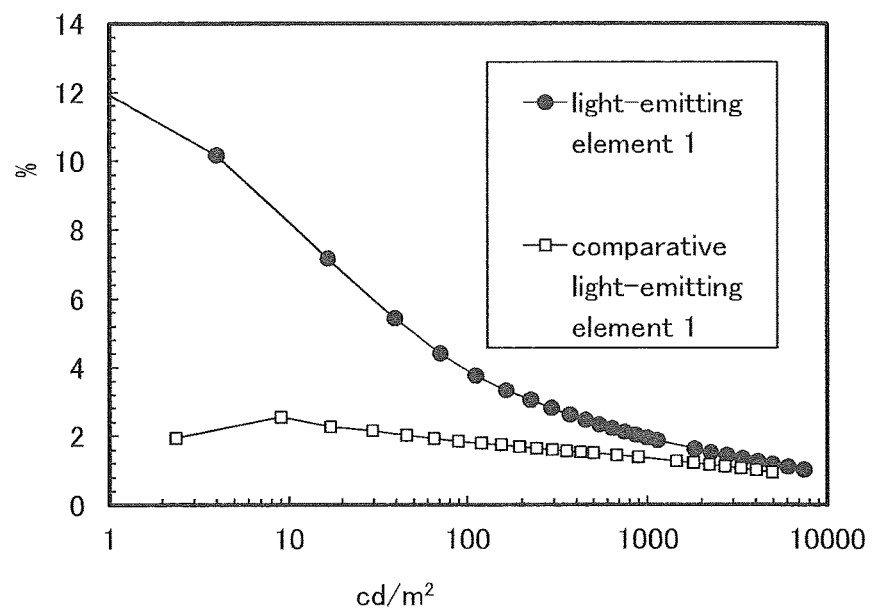
FIG. 20 shows luminance-external quantum efficiency characteristics of a light-emitting element 1 and a comparative light-emitting element 1.
Figure 21:
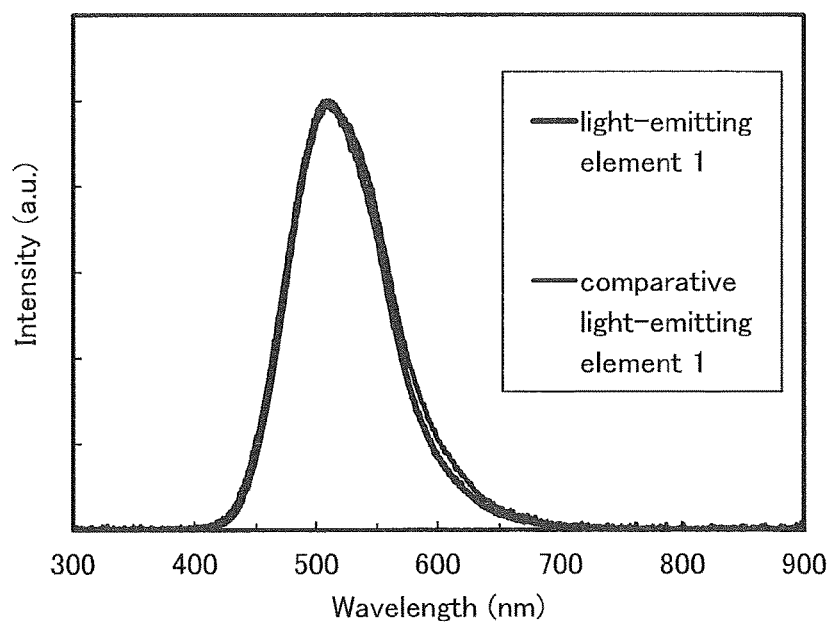
FIG. 21 shows emission spectra of a light-emitting element 1 and a comparative light-emitting element 1.

FIG. 16 shows current density-luminance characteristics of the light-emitting element 1 and the comparative light-emitting element 1; FIG. 17 shows luminance-current efficiency characteristics thereof; FIG. 18 shows voltage-luminance characteristics thereof; FIG. 19 shows luminance-power efficiency characteristics thereof; FIG. 20 shows luminance-external quantum efficiency characteristics thereof; and FIG. 21 shows emission spectra thereof.

Table 1 shows values of major characteristics of the light-emitting element 1 and the comparative light-emitting element 1 at approximately 1000 cd/m².

TABLE 1

|  | Voltage (V) | Current (mA) | Current Density (mA/cm²) | Chromaticity x | Chromaticity y | Current Efficiency (cd/A) | Power Efficiency (lm/W) | External Quantum Efficiency (%) |
|---|---|---|---|---|---|---|---|---|
| Light-emitting Element 1 | 3.9 | 0.73 | 18.2 | 0.25 | 0.49 | 5.5 | 4.4 | 1.9 |
| Comparative Light-emitting Element 1 | 4.4 | 0.93 | 23.2 | 0.23 | 0.45 | 3.8 | 2.7 | 1.4 |

The above results show that the light-emitting element 1 using FrBBiF-II, which is the organic compound described in Embodiment 1, has favorable characteristics. Specifically, according to FIG. 20 showing the external quantum efficiencies, the light-emitting element 1 has an efficiency far exceeding 5% in a low-luminance region. It is said that the extraction efficiency of a light-emitting element like the light-emitting element in this example which is not designed to enhance extraction efficiency is approximately 20% to 30%. The theoretical limit of the internal quantum efficiency of fluorescence, which is based on the generation ratio of singlet excitons generated by current excitation, is 25%. Thus, the theoretical limit of the external quantum efficiency of a fluorescent light-emitting element is calculated to be 5% to 7.5%. It can be found that the external quantum efficiency of the light-emitting element 1 in a low-luminance region far exceeds the theoretical limit.

The above results suggest that an exciplex formed by the first organic compound and the second organic compound (4,6mCzP2Pm and FrBBiF-II) emits light with high efficiency and that the light includes delayed fluorescence components. The light-emitting element 1 was able to emit light with high emission efficiency owing to delayed fluorescence that occurred efficiently via reverse intersystem crossing from a triplet excited state to a singlet excited state.

It was also found that the light-emitting element 1 is a light-emitting element with low drive voltage.

In contrast, the comparative light-emitting element 1 including PCTBi1BP, whose structure is similar to that of FrBBiF-II, has low efficiency. This is probably because the $T_1$ level of PCTBi1BP was lowered owing to its structure in which the biphenyldiyl group connects the 9-phenylcarbazol-3-yl group and the nitrogen atom of the amine, i.e., a structure including a terphenyl skeleton, in which the number of phenyl groups is one more than the number of phenyl groups in a biphenyl skeleton. It can be thus considered that the $T_1$ level of PCTBi1BP became lower than that of the exciplex and the excitation energy of the exciplex was deactivated, leading to such an insufficient efficiency.

Example 3

In this example, the light-emitting element (a light-emitting element 2) described in Embodiment 3 will be described. Note that in the light-emitting element 2, N-(1,1'-biphenyl-4-yl)-N-[4-(dibenzofuran-4-yl)phenyl]-9,9-dimethyl-9H-fluoren-2-amine (abbreviation: FrBBiF-II), which is the organic compound described in Embodiment 1, was used as the second organic compound in the light-emitting layer 113, 2-[3'-(dibenzothiophen-4-yl)biphenyl-3-yl]dibenzo[f,h]quinoxaline (abbreviation: 2mDBTBPDBq-II) was used as the first organic compound, and bis[2-(6-tert-butyl-4-pyrimidinyl-κN3)phenyl-κC](2,4-pentanedionato-κ²O,O')iridium(I II) (abbreviation: [Ir(tBuppm)₂(acac)]) was used as an emission center substance emitting phosphorescence. Chemical formulae of materials used in this example are shown below.

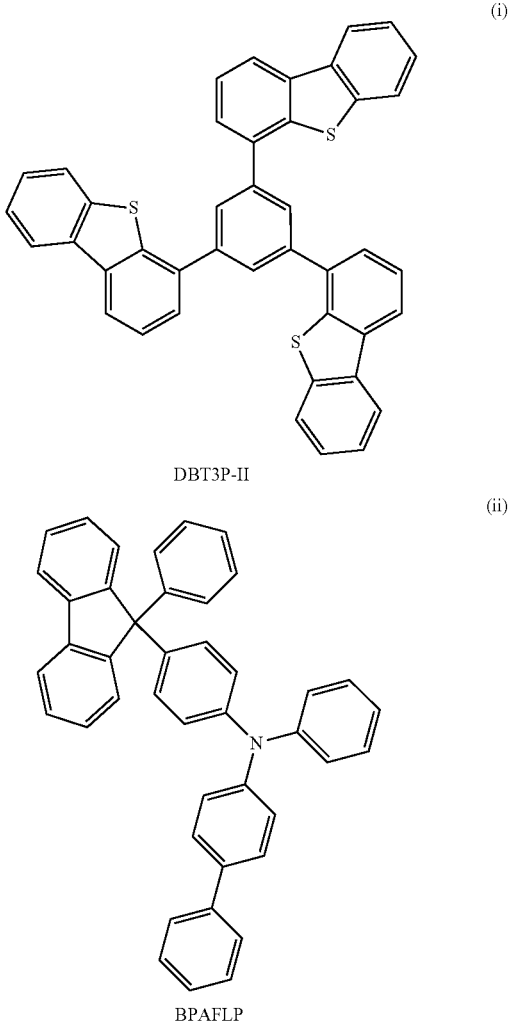

(i) DBT3P-II (ii) BPAFLP

-continued

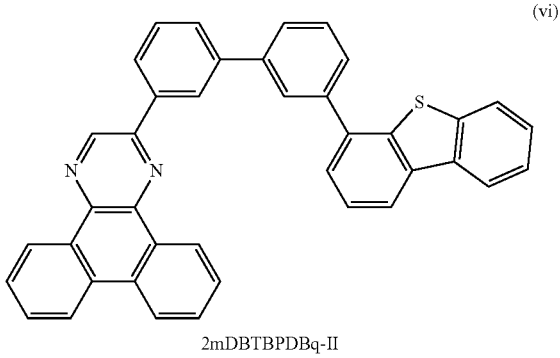

2mDBTBPDBq-II (vi)

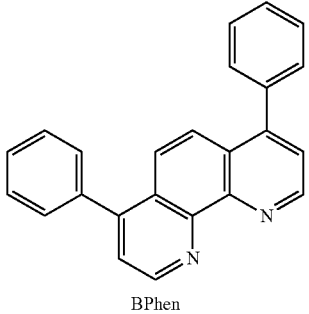

BPhen (iv)

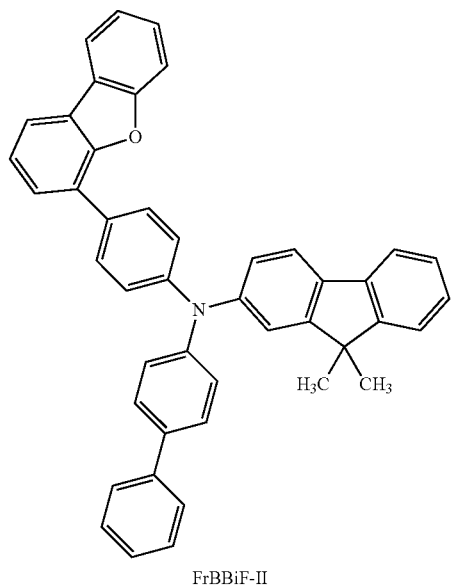

FrBBiF-II (100)

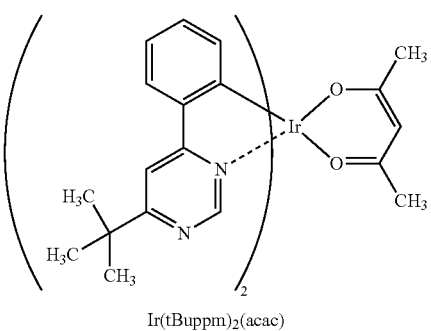

Ir(tBuppm)₂(acac) (vii)

(Method for Fabricating Light-Emitting Element 2)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to approximately $10^{-4}$ Pa. After that, over the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation by an evaporation method using resistance heating, so that the hole-injection layer 111 was formed. The thickness of the hole-injection layer 111 was set to 20 nm, and the weight ratio of DBT3P-II to molybdenum oxide was adjusted to 4:2. Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) which is represented by Structural Formula (ii) was formed to a thickness of 20 nm over the hole-injection layer 111 to form the hole-transport layer 112.

Further, the light-emitting layer 113 was formed over the hole-transport layer 112 in the following manner: 2-[3'-(dibenzothiophen-4-yl)biphenyl-3-yl]dibenzo[f,h]quinoxaline (abbreviation: 2mDBTBPDBq-II) represented by Structural Formula (vi), N-(1,1'-biphenyl-4-yl)-N-[4-(dibenzofuran-4-yl)phenyl]-9,9-dimethyl-9H-fluoren-2-amine (abbreviation: FrBBiF-II) represented by Structural Formula (100), and bis[2-(6-tert-butyl-4-pyrimidinyl-N3)phenyl-κC](2,4-pentanedionato-κ²O,O')iridium(I II) (abbreviation: [Ir(tBuppm)$_2$(acac)]) represented by Structural Formula (vii) were deposited by co-evaporation to a thickness of 20 nm such that the weight ratio of 2mDBTBPDBq-II to FrBBiF-II and [Ir(tBuppm)$_2$(acac)] was 0.7:0.3:0.05; then, 2mDBTBPDBq-II, FrBBiF-II, and [Ir(tBuppm)$_2$(acac)] were deposited by co-evaporation to a thickness of 20 nm such that the weight ratio of 2mDBTBPDBq-II to FrBBiF-II and [Ir(tBuppm)$_2$(acac)] was 0.8:0.2:0.05.

Then, the electron-transport layer 114 was formed over the light-emitting layer 113 in such a way that a 10 nm thick film of 2mDBTBPDBq-II was formed and a 20 nm thick film of bathophenanthroline (abbreviation: BPhen) represented by Structural Formula (iv) was formed.

After the formation of the electron-transport layer 114, lithium fluoride (LiF) was deposited by evaporation to a thickness of 1 nm, so that the electron-injection layer 115 was formed. Lastly, aluminum was deposited by evaporation to a thickness of 200 nm to form the second electrode 102 functioning as a cathode. Thus, the light-emitting element 2 in this example was fabricated.

Note that in all the above evaporation steps, evaporation was performed by a resistance-heating method.

The light-emitting element 2 was sealed using a glass substrate in a glove box containing a nitrogen atmosphere so as not to be exposed to the air (specifically, a sealing material was applied onto an outer edge of the element and heat treatment was performed at 80° C. for 1 hour at the time of sealing). Then, initial characteristics of the light-emitting element were measured. Note that the measurement was carried out at room temperature (in an atmosphere kept at 25° C.).

Figure 22:
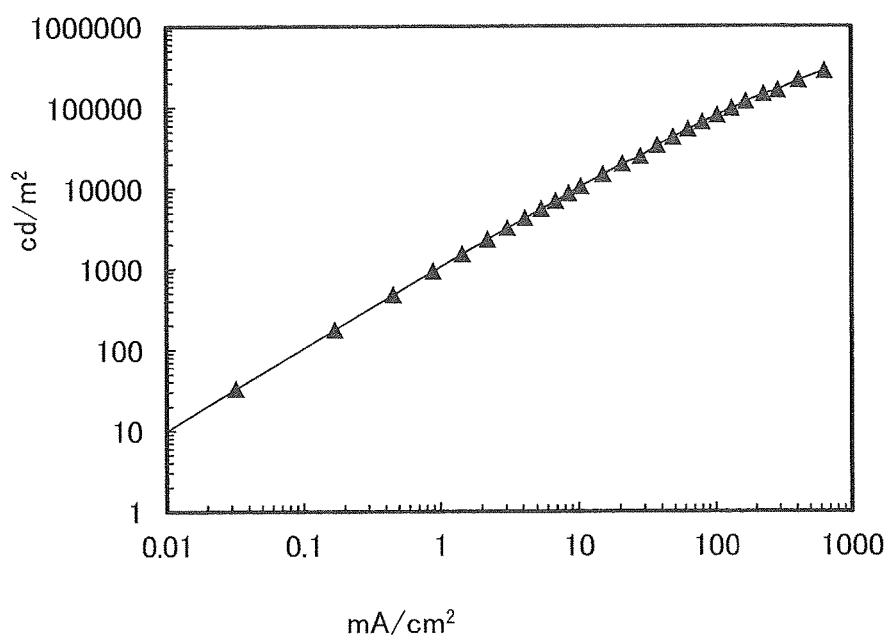
FIG. 22 shows current density-luminance characteristics of a light-emitting element 2.
Figure 23:
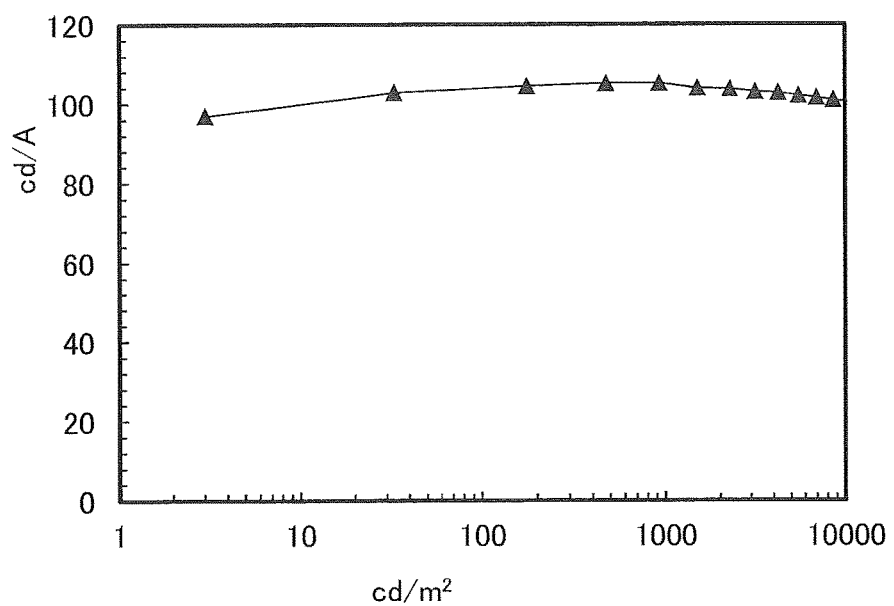
FIG. 23 shows luminance-current efficiency characteristics of a light-emitting element 2.
Figure 24:
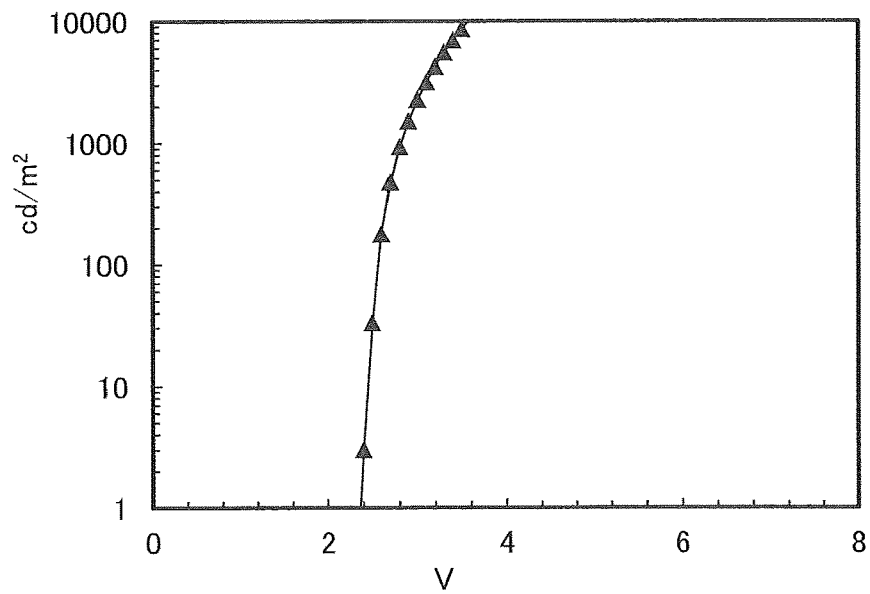
FIG. 24 shows voltage-luminance characteristics of a light-emitting element 2.
Figure 25:
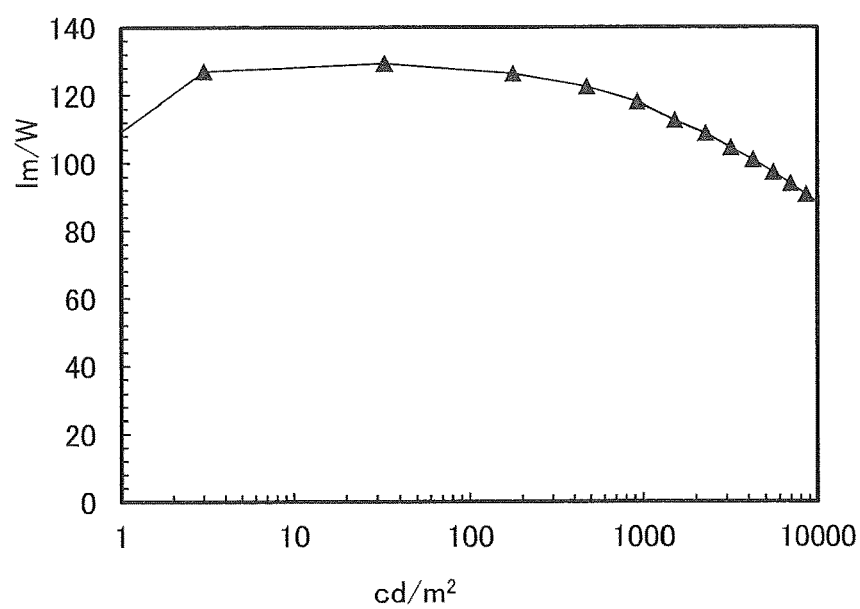
FIG. 25 shows luminance-power efficiency characteristics of a light-emitting element 2.
Figure 26:
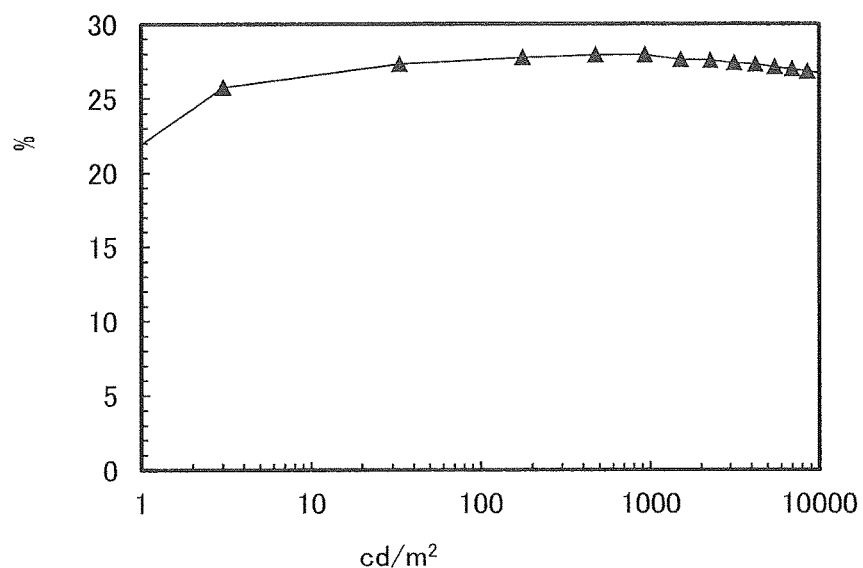
FIG. 26 shows luminance-external quantum efficiency characteristics of a light-emitting element 2.
Figure 27:
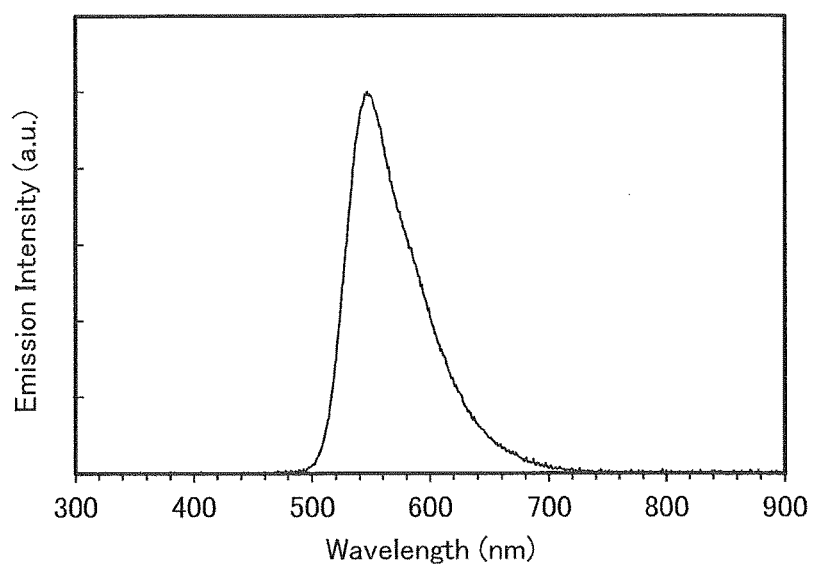
FIG. 27 shows an emission spectrum of a light-emitting element 2.

FIG. 22 shows current density-luminance characteristics of the light-emitting element 2; FIG. 23 shows luminance-current efficiency characteristics thereof; FIG. 24 shows voltage-luminance characteristics thereof; FIG. 25 shows luminance-power efficiency characteristics thereof; FIG. 26 shows luminance-external quantum efficiency characteristics thereof; and FIG. 27 shows an emission spectrum thereof.

Table 2 shows values of major characteristics of the light-emitting element 2 at approximately 1000 cd/m².

The above results show that the light-emitting element 2 using FrBBiF-II, which is the organic compound described in Embodiment 1, has extremely favorable characteristics also when a light-emitting substance emitting yellowish green phosphorescence is used as an emission center substance.

In particular, the external quantum efficiency was excellent; the value was kept high even in a high-luminance region. Besides, the drive voltage was low, and as a result, an extremely high power efficiency of 120 lm/W or more was achieved.

Figure 28:
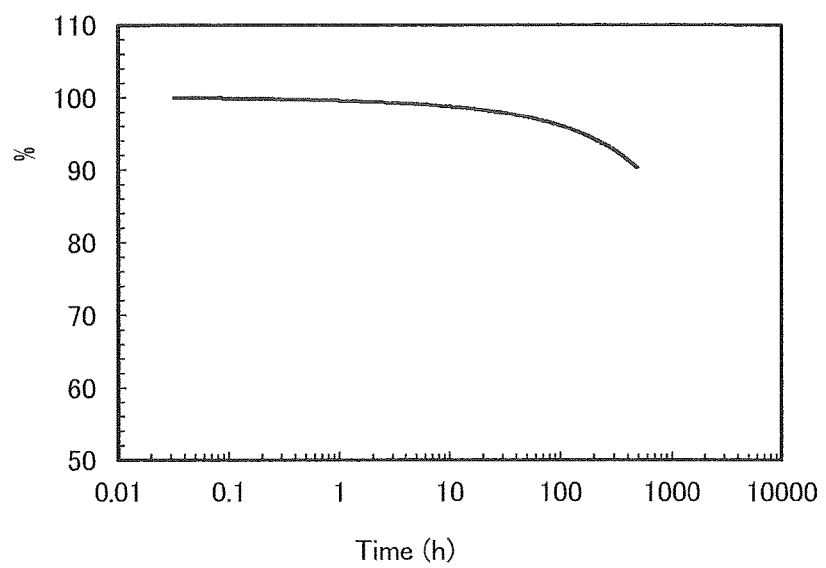
FIG. 28 shows time dependence of normalized luminance of a light-emitting element 2.

A reliability test was carried out, and the results thereof are shown in FIG. 28. In the reliability test, the light-emitting element 2 was driven under the conditions where the initial luminance was set to 5000 cd/m² and the current density was constant. FIG. 28 shows a change in normalized luminance where the initial luminance is 100%. The results show that a decrease in luminance over driving time of the light-emitting element 2 is small, and thus the light-emitting element 2 has favorable reliability.

Example 4

In this example, a light-emitting element (a light-emitting element 3) in which N-(1,1'-biphenyl-4-yl)-N-[4-(dibenzofuran-4-yl)phenyl]-9,9-dimethyl-9H-fluoren-2-amine (abbreviation: FrBBiF-II) is used in a hole-transport layer will be described. Chemical formulae of substances used in this example are shown below.

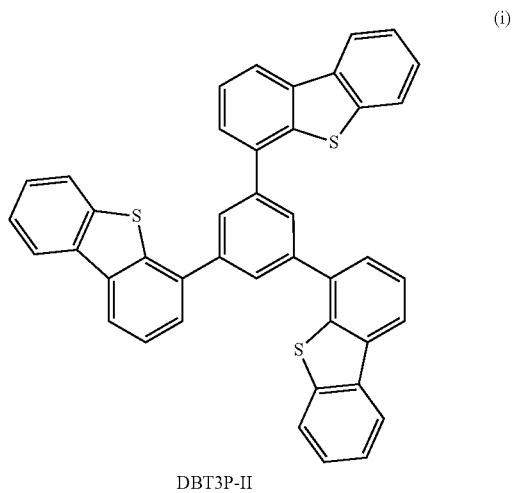

(i)

DBT3P-II

TABLE 2

| | Voltage (V) | Current (mA) | Current Density (mA/cm²) | Chromaticity x | Chromaticity y | Current Efficiency (cd/A) | Power Efficiency (lm/W) | External Quantum Efficiency (%) |
|---|---|---|---|---|---|---|---|---|
| Light-emitting Element 2 | 2.8 | 0.04 | 0.9 | 0.42 | 0.57 | 105.2 | 118.0 | 27.9 |

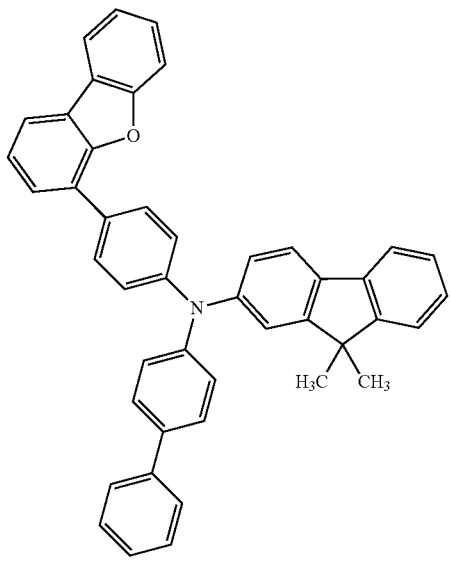

FrBBiF-II

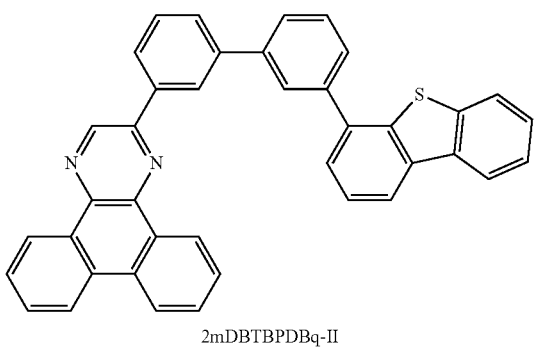

2mDBTBPDBq-II

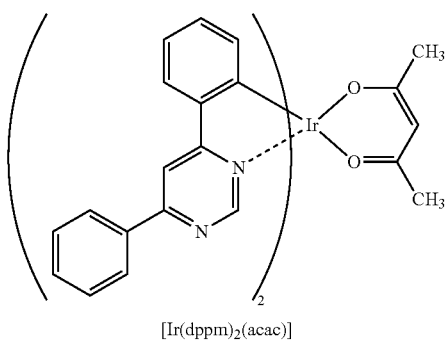

[Ir(dppm)₂(acac)]

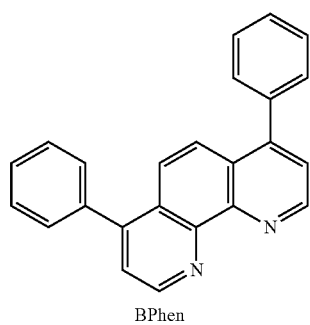

BPhen

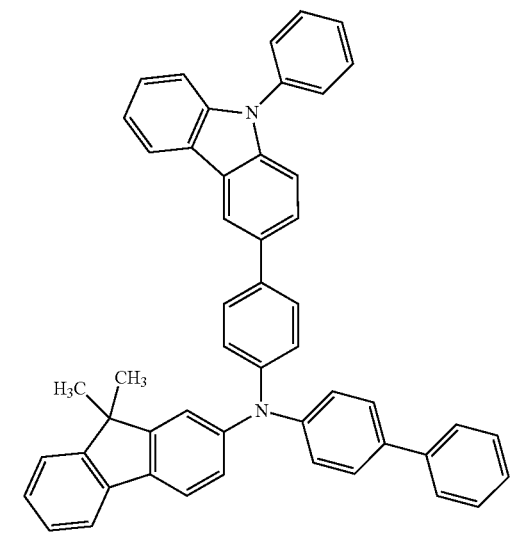

PCBBiF (Method for Fabricating Light-Emitting Element 3)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to approximately $10^{-4}$ Pa. After that, over the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation by an evaporation method using resistance heating, so that the hole-injection layer 111 was formed. The thickness of the hole-injection layer 111 was set to 20 nm, and the weight ratio of DBT3P-II to molybdenum oxide was adjusted to 4:2. Note that the co-evaporation method refers to an evaporation method in which evaporation is carried out from a plurality of evaporation sources at the same time in one treatment chamber.

Next, a film of N-(1,1'-biphenyl-4-yl)-N-[4-(dibenzofuran-4-yl)phenyl]-9,9-dimethyl-9H-fluoren-2-amine (abbreviation: FrBBiF-II) represented by Structural Formula (100) was formed to a thickness of 20 nm over the hole-injection layer 111 to form the hole-transport layer 112.

Further, the light-emitting layer 113 was formed over the hole-transport layer 112 in the following manner: 2-[3'-

(dibenzothiophen-4-yl)biphenyl-3-yl]dibenzo[f,h]quinoxaline (abbreviation: 2mDBTBPDBq-II) represented by Structural Formula (vi), N-(1,1'-biphenyl-4-yl)-N-[4-(9-phenyl-9H-carbazol-3-yl)phenyl]-9,9-dimethyl-9H-fluor en-2-amine (abbreviation: PCBBiF) represented by Structural Formula (viii), and (acetylacetonato)bis(4,6-diphenylpyrimidinato)iridium(III) (abbreviation: [Ir(dppm)$_2$(acac)]) represented by Structural Formula (ix) were deposited by co-evaporation to a thickness of 20 nm such that the weight ratio of 2mDBTBPDBq-II to PCBBiF and [Ir(dppm)$_2$(acac)] was 0.7:0.3:0.05; then, 2mDBTBPDBq-II, PCBBiF, and [Ir(dppm)$_2$(acac)] were deposited by co-evaporation to a thickness of 20 nm such that the weight ratio of 2mDBT-BPDBq-II to PCBBiF and [Ir(dppm)$_2$(acac)] was 0.8:0.2:0.05.

Then, the electron-transport layer 114 was formed over the light-emitting layer 113 in such a way that a 20 nm thick film of 2mDBTBPDBq-II was formed and a 10 nm thick film of bathophenanthroline (abbreviation: BPhen) represented by Structural Formula (iv) was formed.

After the formation of the electron-transport layer 114, lithium fluoride (LiF) was deposited by evaporation to a thickness of 1 run, so that the electron-injection layer 115 was formed. Lastly, aluminum was deposited by evaporation to a thickness of 200 nm to form the second electrode 102 functioning as a cathode. Thus, the light-emitting element 3 in this example was fabricated.

Note that in all the above evaporation steps, evaporation was performed by a resistance-heating method.

The light-emitting element 3 was sealed using a glass substrate in a glove box containing a nitrogen atmosphere so as not to be exposed to the air (specifically, a sealing material was applied onto an outer edge of the element and heat treatment was performed at 80° C. for 1 hour at the time of sealing). Then, initial characteristics of the light-emitting element were measured. Note that the measurement was carried out at room temperature (in an atmosphere kept at 25° C.).

Figure 29:
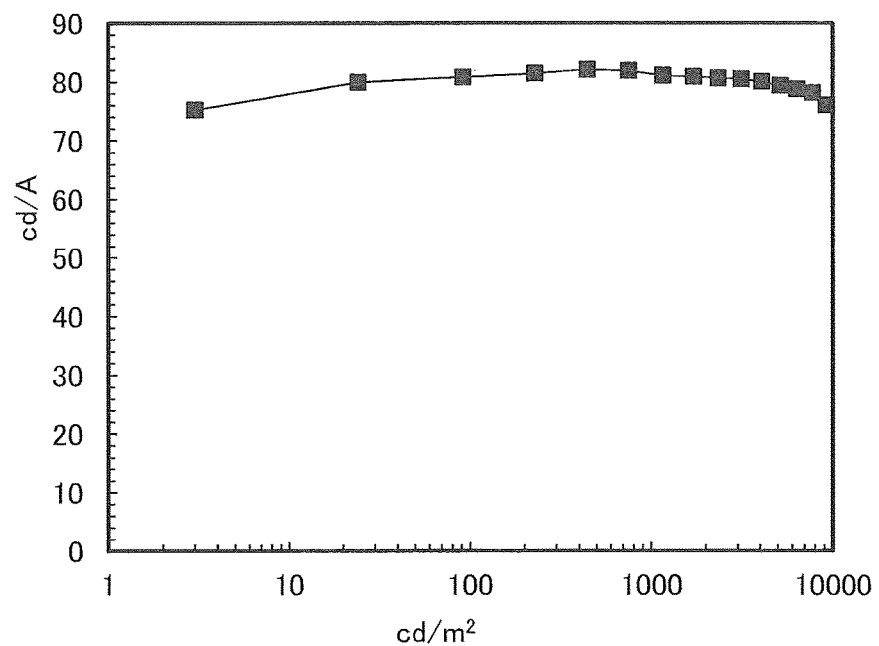
FIG. 29 shows luminance-current efficiency characteristics of a light-emitting element 3.
Figure 30:
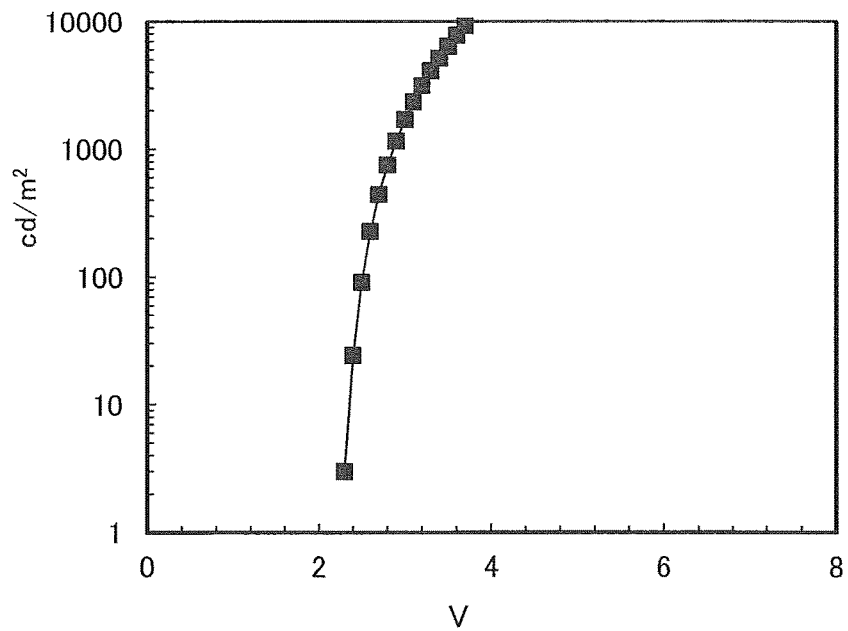
FIG. 30 shows voltage-luminance characteristics of a light-emitting element 3.
Figure 31:
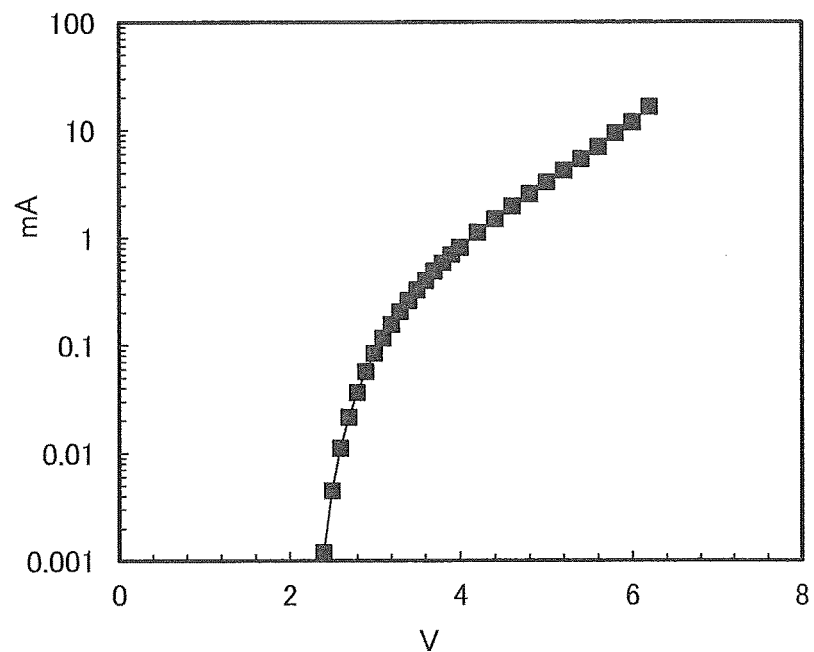
FIG. 31 shows voltage-current characteristics of a light-emitting element 3.
Figure 32:
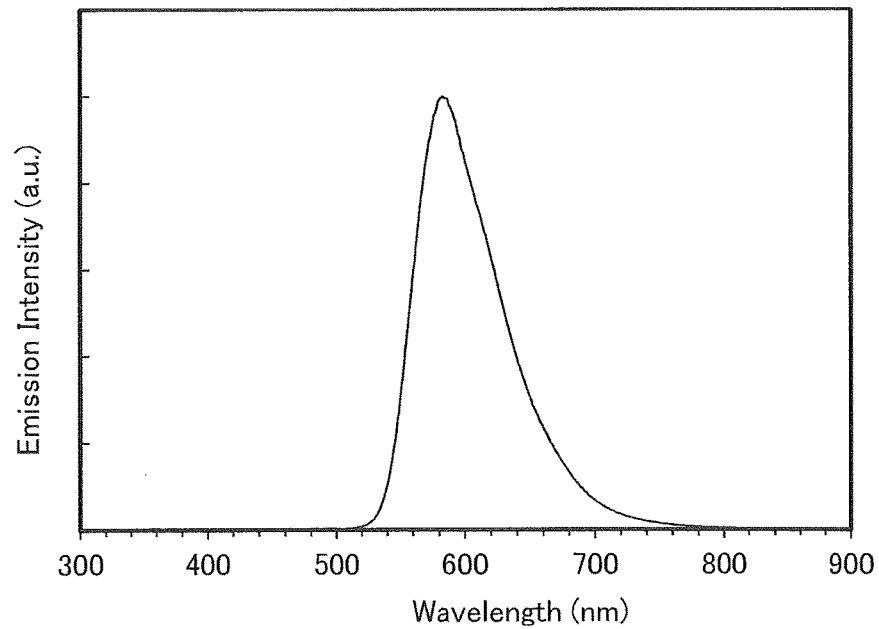
FIG. 32 shows an emission spectrum of a light-emitting element 3.

FIG. 29 shows luminance-current efficiency characteristics of the light-emitting element 3; FIG. 30 shows voltage-luminance characteristics thereof; FIG. 31 shows voltage-current characteristics thereof; and FIG. 32 shows an emission spectrum thereof.

Table 3 shows values of major characteristics of the light-emitting element 3 at approximately 1000 cd/m$^2$.

Figure 33:
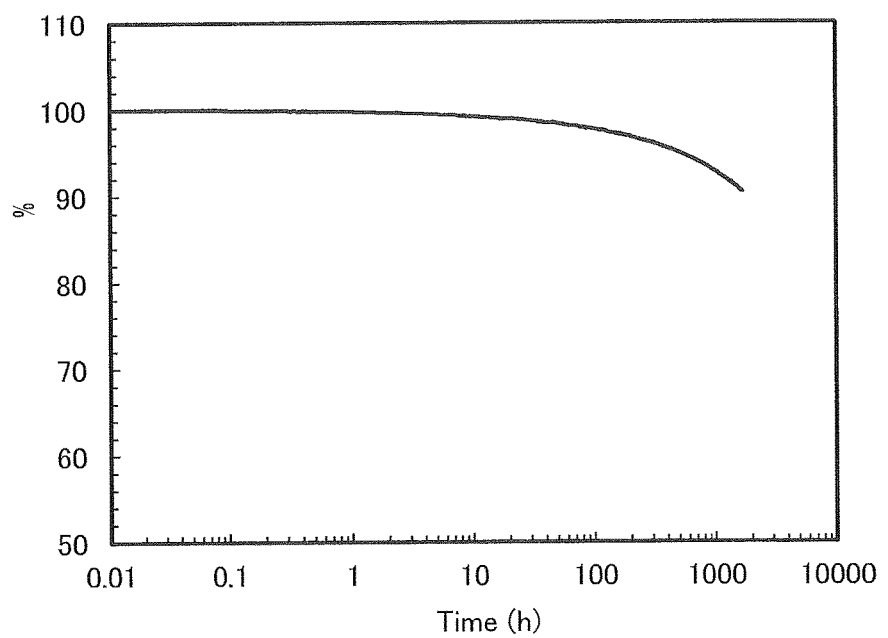
FIG. 33 shows time dependence of normalized luminance of a light-emitting element 3.

A reliability test was carried out, and the results thereof are shown in FIG. 33. In the reliability test, the light-emitting element 3 was driven under the conditions where the initial luminance was set to 5000 cd/m$^2$ and the current density was constant. FIG. 33 shows a change in normalized luminance where the initial luminance is 100%. The results show that a decrease in luminance over driving time of the light-emitting element 3 is small, and thus the light-emitting element 3 has favorable reliability.

Example 5

In this example, a method for synthesizing N-(1,1'-biphenyl-4-yl)-N-[4-(dibenzothiophen-4-yl)phenyl]-9,9-dimethyl-9H-fluoren-2-amine (abbreviation: ThBBiF) represented by Structural Formula (200) will be described.

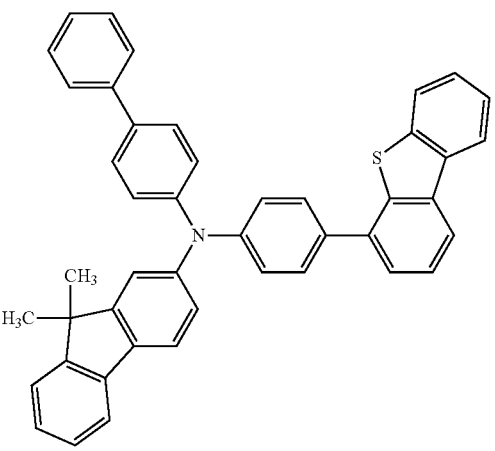

(200)

First, 2.2 g (6.4 mmol) of 4-(4-bromophenyl)dibenzothiophene, 2.5 g (6.8 mmol) of N-(1,1'-biphenyl-4-yl)-9,9-dimethyl-9H-fluoren-2-amine, and 1.9 g (19.4 mmol) of sodium tert-butoxide were put in a 200-mL three-neck flask and the air in the flask was replaced with nitrogen. To this mixture were added 33.0 mL of toluene and 0.4 mL of a 10% hexane solution of tri(tert-butyl)phosphine, the temperature was set to 60° C., and 37 mg (0.1 mmol) of bis(dibenzylideneacetone)palladium(0) was added; then, the temperature was raised to 80° C. and stirring was performed for 2.0

TABLE 3

| | Voltage (V) | Current (mA) | Current Density (mA/cm$^2$) | Chromaticity x | Chromaticity y | Current Efficiency (cd/A) | Power Efficiency (lm/W) | External Quantum Efficiency (%) |
|---|---|---|---|---|---|---|---|---|
| Light-emitting Element 3 | 2.9 | 0.06 | 1.4 | 0.56 | 0.44 | 81 | 88 | 30 |

The above results show that the light-emitting element 3 in which the hole-transport layer includes FrBBiF-II, which is the organic compound described in Embodiment 1, has extremely favorable characteristics when a light-emitting substance emitting orange phosphorescence is used as an emission center substance.

In particular, the external quantum efficiency was excellent; the value was kept high even in a high-luminance region.

hours. After the stirring, suction filtration through Florisil, Celite, and alumina was carried out to give a filtrate. The filtrate was concentrated to give a solid. The solid was purified by silica gel column chromatography (the developing solvent was hexane and toluene in a ratio of 3:1) to give a solid. The solid was recrystallized from toluene and hexane, so that 3.4 g of an objective solid was obtained in a yield of 85%.

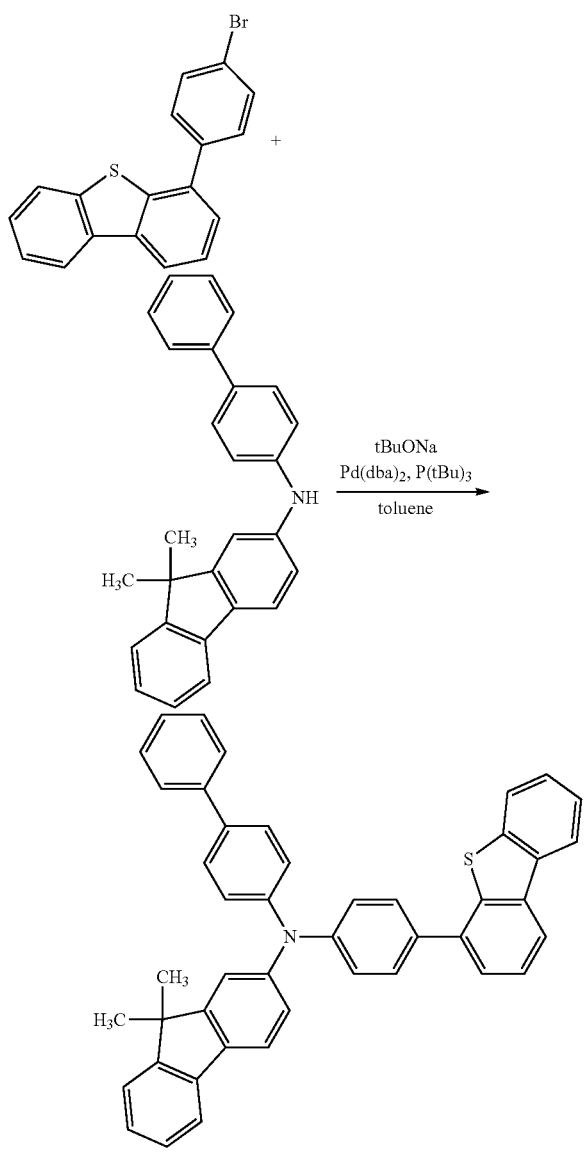

Using a train sublimation method, 1.5 g of the obtained solid was purified by sublimation. In the purification by sublimation, under a pressure of 2.8 Pa and with an argon gas flow rate of 5.0 mL/min, the solid was heated at 256° C. for 16.0 hours and then at 265° C. for 2.0 hours. After the purification by sublimation, 1.4 g of a solid which was the object of the synthesis was obtained at a collection rate of 95%.

Results of measurement of the obtained solid by nuclear magnetic resonance ($^1$H NMR) are shown below.

$^1$H NMR (CDCl$_3$, 500 MHz): δ=1.47 (s, 6H), 7.18 (dd, J=8.3 Hz, 2.5 Hz, 1H), 7.27-7.35 (m, 8H), 7.41-7.50 (m, 5H), 7.51-7.57 (m, 4H), 7.61-7.68 (m, 6H), 7.84-7.88 (m, 1H), 8.14 (dd, J=7.5 Hz, 1.0 Hz, 1H), 8.17-8.21 (m, 1H).

Figure 34A:
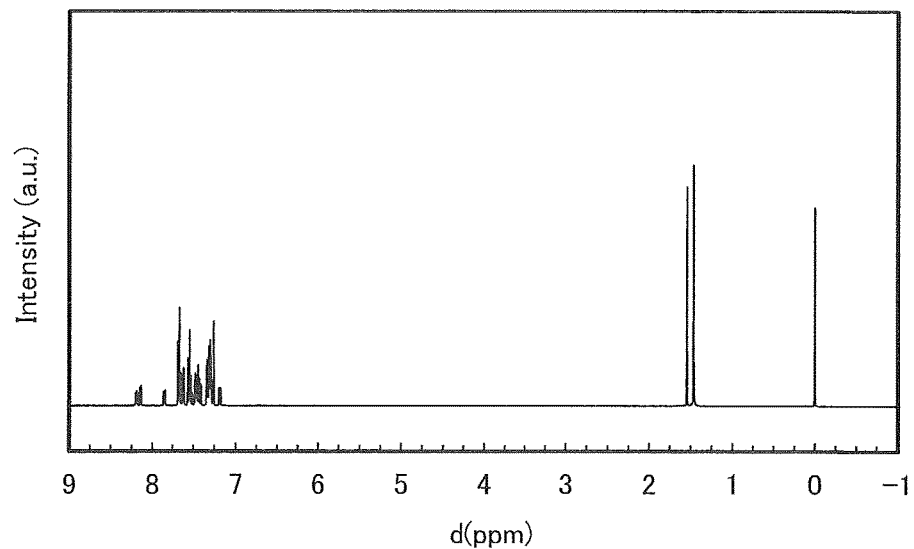
FIGS. 34A and 34B are NMR charts of ThBBiF.
Figure 34B:
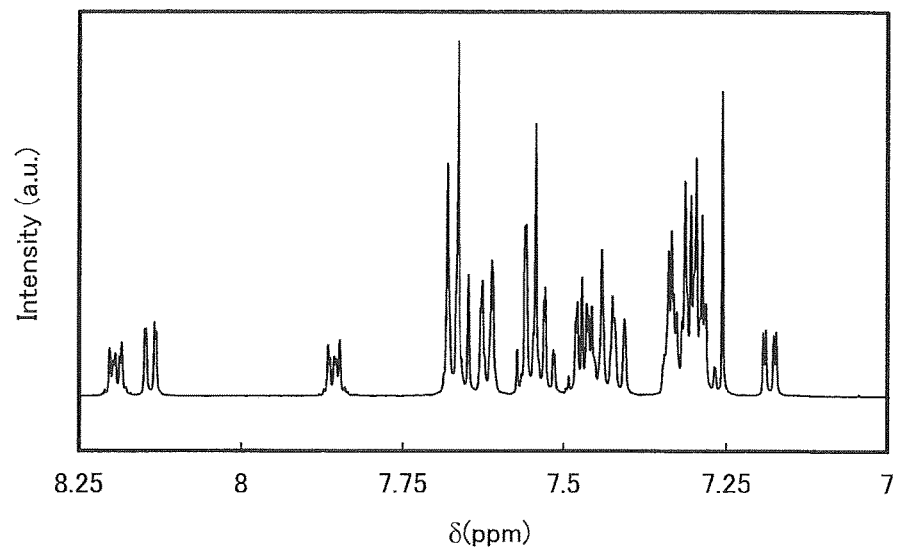

FIGS. 34A and 34B are NMR charts. Note that FIG. 34B shows an enlarged part of FIG. 34A in the range of 7.00 ppm to 8.25 ppm. The measurement results confirmed that N-(1,1'-biphenyl-4-yl)-N-[4-(dibenzothiophen-4-yl)phenyl]-9,9-dimethyl-9H-fluoren-2-amine (abbreviation: ThBBiF), which was the target substance, was obtained.

Thermogravimetry-differential thermal analysis (TG-DTA) of the obtained ThBBiF was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 403° C., which is indicative of high heat resistance.

Furthermore, ThBBiF was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode.

Figure 35:
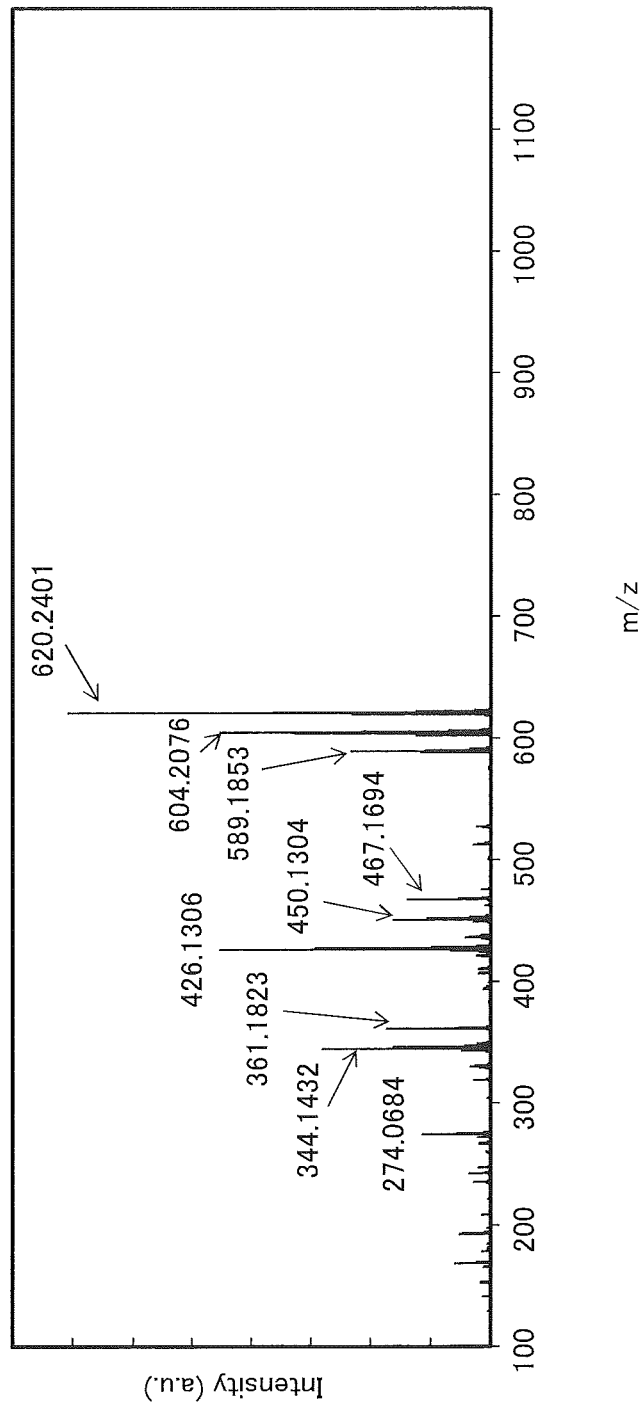
FIG. 35 shows results of LC/MS analysis of ThBBiF.

A component which underwent the ionization under the above-mentioned conditions was collided with an argon gas in a collision cell to dissociate into product ions. Energy (collision energy) for the collision with argon was 50 eV. A mass range for the measurement was m/z=100 to 1200. FIG. 35 shows the results.

<<Physical Properties of ThBBiF>>

Figure 36A:
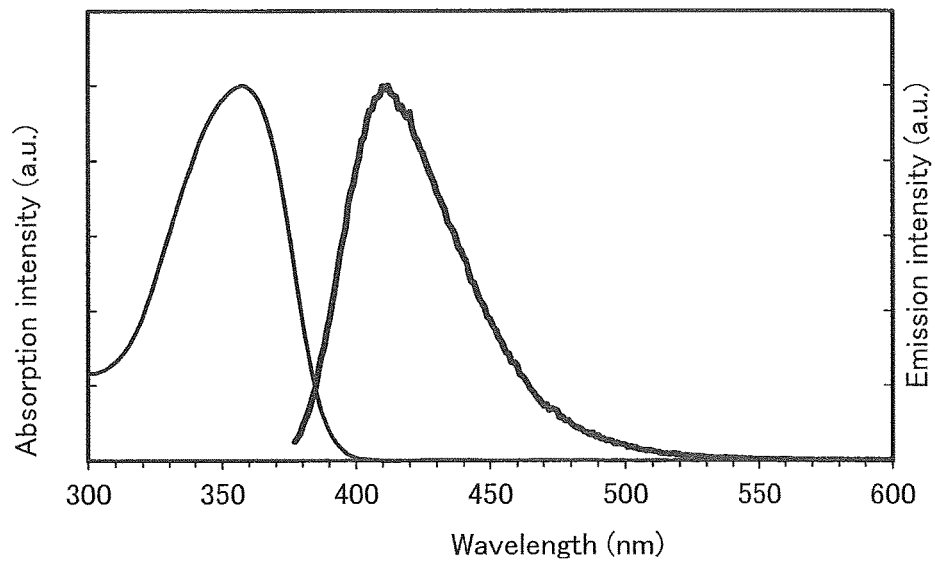
FIGS. 36A and 36B show absorption spectra and emission spectra of ThBBiF.
Figure 36B:
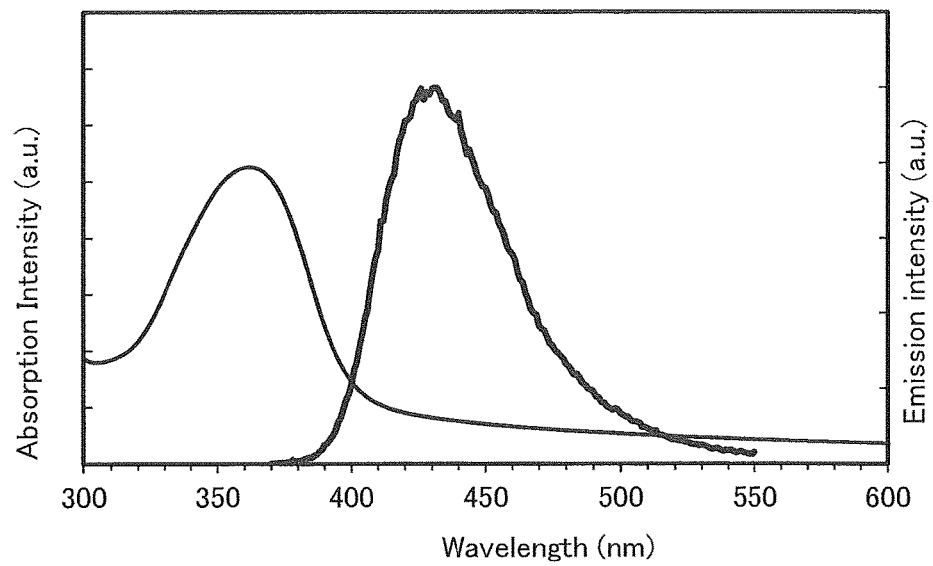

FIG. 36A shows an absorption spectrum and an emission spectrum of ThBBiF in a toluene solution of ThBBiF, and FIG. 36B shows an absorption spectrum and an emission spectrum of a thin film of ThBBiF. The spectra were measured with a UV-visible spectrophotometer (V550, produced by JASCO Corporation). The spectra of ThBBiF in the toluene solution of ThBBiF were measured with a toluene solution of ThBBiF put in a quartz cell. The spectra of the thin film were measured with a sample prepared by deposition of ThBBiF on a quartz substrate by evaporation. Note that in the case of the absorption spectrum of ThBBiF in the toluene solution of ThBBiF, the absorption spectrum obtained by subtraction of the absorption spectra of the quartz cell and toluene from the measured spectra is shown in the drawing and that in the case of the absorption spectrum of the thin film of ThBBiF, the absorption spectrum obtained by subtraction of the absorption spectrum of the quartz substrate from the measured spectra is shown in the drawing.

As shown in FIG. 36A, in the case of ThBBiF in the toluene solution, an absorption peak was observed at approximately 358 nm, and an emission wavelength peak was observed at approximately 411 nm (excitation wavelength: 362 nm). As shown in FIG. 36B, in the case of the thin film of ThBBiF, absorption peaks were observed at approximately 362 nm, 289 nm, 242 nm, and 210 nm, and an emission wavelength peak was observed at approximately 431 nm (excitation wavelength: 363 nm). Thus, it was found that absorption and light emission of ThBBiF occur in extremely short wavelength regions.

The ionization potential of ThBBiF in a thin film state was measured by photoelectron spectroscopy (the measuring instrument: AC-2, manufactured by Riken Keiki, Co., Ltd.) in the air. The obtained value of the ionization potential was converted into a negative value, so that the HOMO level of ThBBiF was determined to be −5.60 eV. From the data of the absorption spectrum of the thin film in FIG. 36B, the absorption edge of ThBBiF, which was obtained from Tauc plot with an assumption of direct transition, was 3.15 eV. Therefore, the optical energy gap of ThBBiF in a solid state was estimated at 3.15 eV; from the values of the HOMO level obtained above and this energy gap, the LUMO level of ThBBiF was estimated at −2.45 eV. This reveals that ThBBiF in the solid state has an energy gap as wide as 3.15 eV.

Example 6

In this example, the light-emitting element (a light-emitting element 4) described in Embodiment 3 will be described. Note that in the light-emitting element 4, N-(1,1'-biphenyl-4-yl)-N-[4-(dibenzothiophen-4-yl)phenyl]-9,9-dimethyl-9H-fluoren-2-amine (abbreviation: ThBBiF), which is the organic compound described in Embodiment 1, was used as the second organic compound in the light-emitting layer 113, 2-[3'-(dibenzothiophen-4-yl)biphenyl-3-yl]dibenzo[f,h]quinoxaline (abbreviation: 2mDBTBPDBq-II) was used as the first organic compound, and bis[2-(6-tert-butyl-4-pyrimidinyl-N3)phenyl-κC](2,4-pentanedionato-κ²O,O')iridium(I II) (abbreviation: [Ir(tBuppm)₂(acac)]) was used as an emission center substance emitting phosphorescence. Chemical formulae of materials used in this example are shown below.

(i)

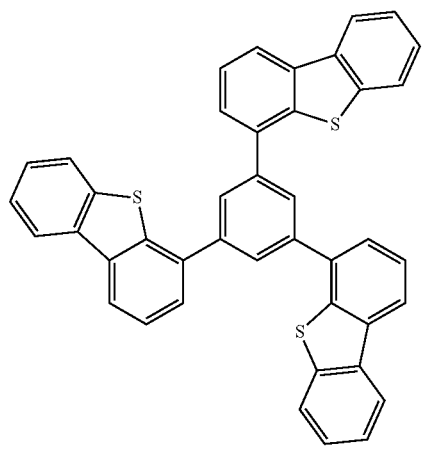

DBT3P-II (ii)

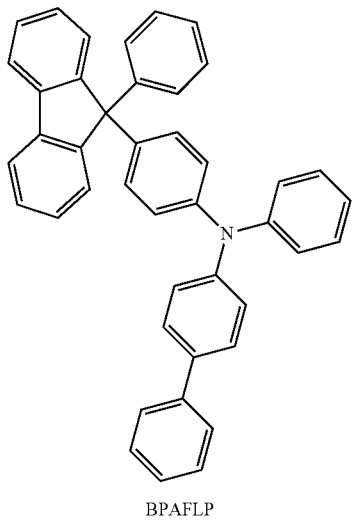

BPAFLP

-continued (vi)

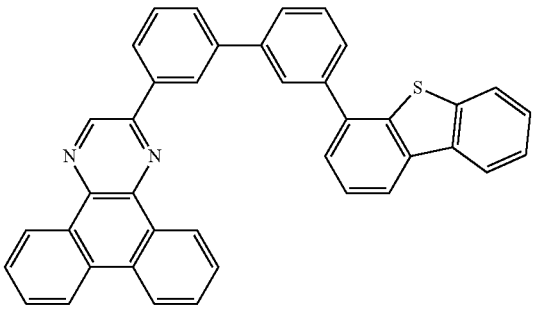

2mDBTBPDBq-II (vii)

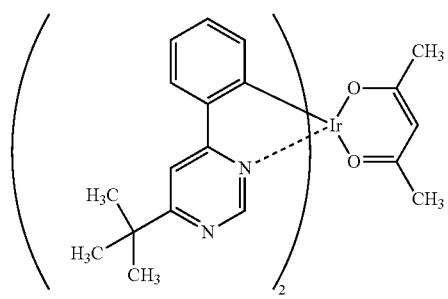

Ir(tBuppm)₂(acac)

(200)

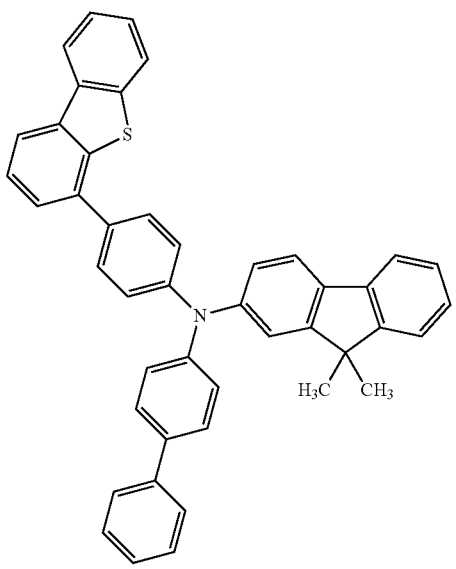

ThBBiF (iv)

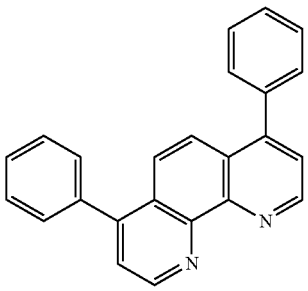

BPhen (Method for Fabricating Light-Emitting Element 4)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to approximately $10^{-4}$ Pa. After that, over the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation by an evaporation method using resistance heating, so that the hole-injection layer 111 was formed. The thickness of the hole-injection layer 111 was set to 20 nm, and the weight ratio of DBT3P-II to molybdenum oxide was adjusted to 4:2.

Next, a film of 4-phenyl-4'-(9-phenylfluoren-9-yl)triphenylamine (abbreviation: BPAFLP) which is represented by Structural Formula (ii) was formed to a thickness of 20 run over the hole-injection layer 111 to form the hole-transport layer 112.

Further, the light-emitting layer 113 was formed over the hole-transport layer 112 in the following manner: 2-[3'-(dibenzothiophen-4-yl)biphenyl-3-yl]dibenzo[f,h]quinoxaline (abbreviation: 2mDBTBPDBq-II) represented by Structural Formula (vi), N-(1,1'-biphenyl-4-yl)-N-[4-(dibenzothiophen-4-yl)phenyl]-9,9-dimethyl-9H-fluoren-2-amine (abbreviation: ThBBiF) represented by Structural Formula (200), and bis[2-(6-tert-butyl-4-pyrimidinyl-N3)phenyl-κC](2,4-pentanedionato-κ²O,O')iridium(I II) (abbreviation: [Ir(tBuppm)$_2$(acac)]) represented by Structural Formula (vii) were deposited by co-evaporation to a thickness of 20 nm such that the weight ratio of 2mDBTBPDBq-II to ThBBiF and [Ir(tBuppm)$_2$(acac)] was 0.7:0.3:0.05; then, 2mDBTBPDBq-II, ThBBiF, and [Ir(tBuppm)$_2$(acac)] were deposited by co-evaporation to a thickness of 20 nm such that the weight ratio of 2mDBTBPDBq-II to ThBBiF and [Ir(tBuppm)$_2$(acac)] was 0.8:0.2:0.05.

Then, the electron-transport layer 114 was formed over the light-emitting layer 113 in such a way that a 20 nm thick film of 2mDBTBPDBq-II was formed and a 10 nm thick film of bathophenanthroline (abbreviation: BPhen) represented by Structural Formula (iv) was formed.

After the formation of the electron-transport layer 114, lithium fluoride (LiF) was deposited by evaporation to a thickness of 1 nm, so that the electron-injection layer 115 was formed. Lastly, aluminum was deposited by evaporation to a thickness of 200 nm to form the second electrode 102 functioning as a cathode. Thus, the light-emitting element 4 in this example was fabricated.

Note that in all the above evaporation steps, evaporation was performed by a resistance-heating method.

The light-emitting element 4 was sealed using a glass substrate in a glove box containing a nitrogen atmosphere so as not to be exposed to the air (specifically, a sealing material was applied onto an outer edge of the element and heat treatment was performed at 80° C. for 1 hour at the time of sealing). Then, initial characteristics of the light-emitting element were measured. Note that the measurement was carried out at room temperature (in an atmosphere kept at 25° C.).

Figure 37:
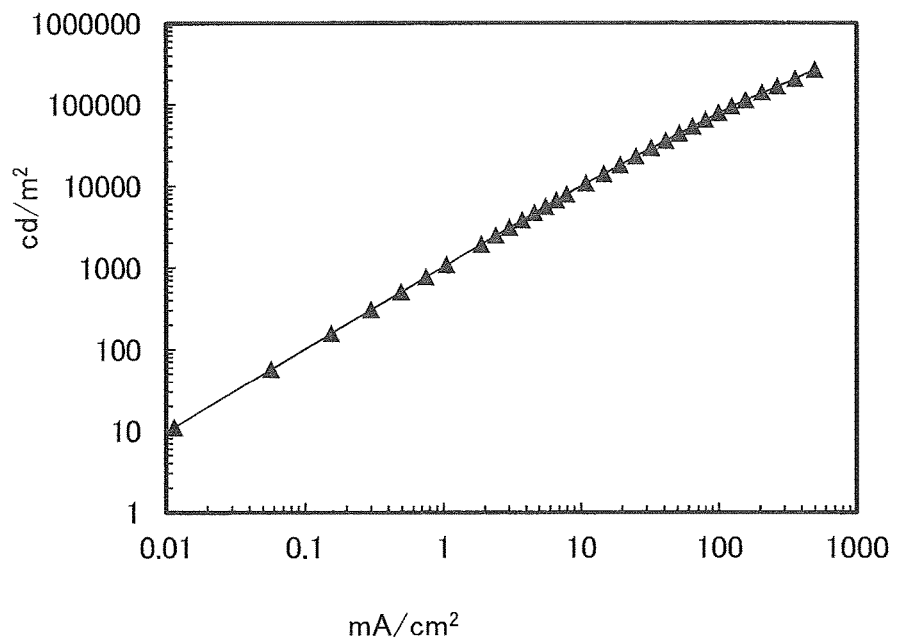
FIG. 37 shows current density-luminance characteristics of a light-emitting element 4.
Figure 38:
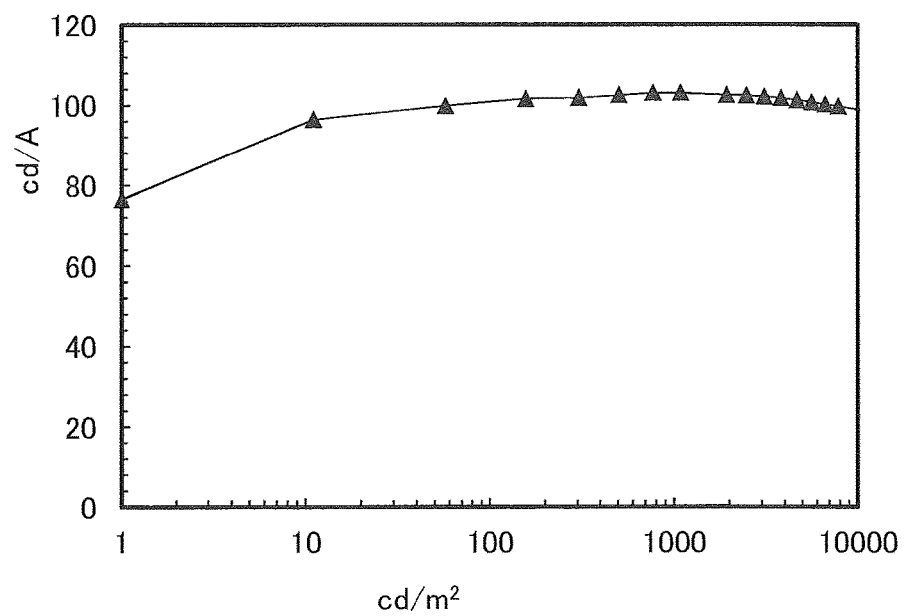
FIG. 38 shows luminance-current efficiency characteristics of a light-emitting element 4.
Figure 39:
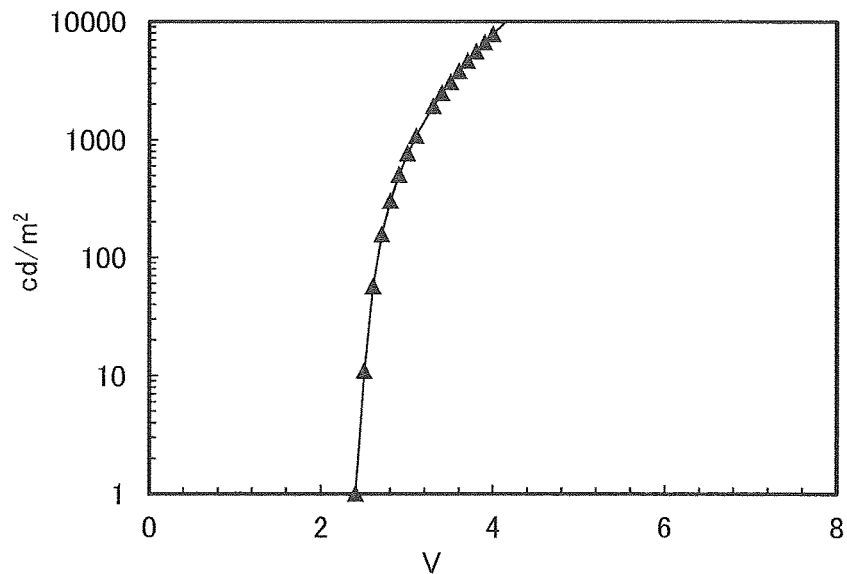
FIG. 39 shows voltage-luminance characteristics of a light-emitting element 4.
Figure 40:
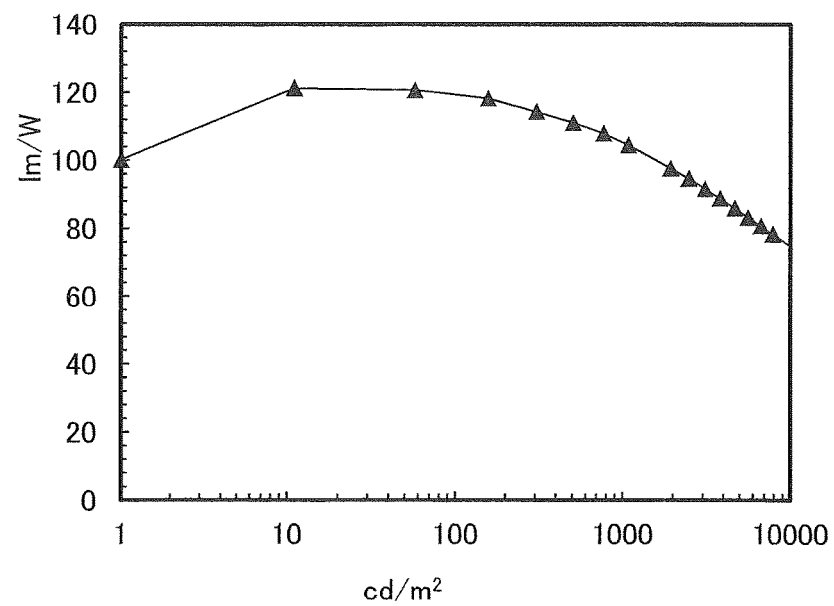
FIG. 40 shows luminance-power efficiency characteristics of a light-emitting element 4.
Figure 41:
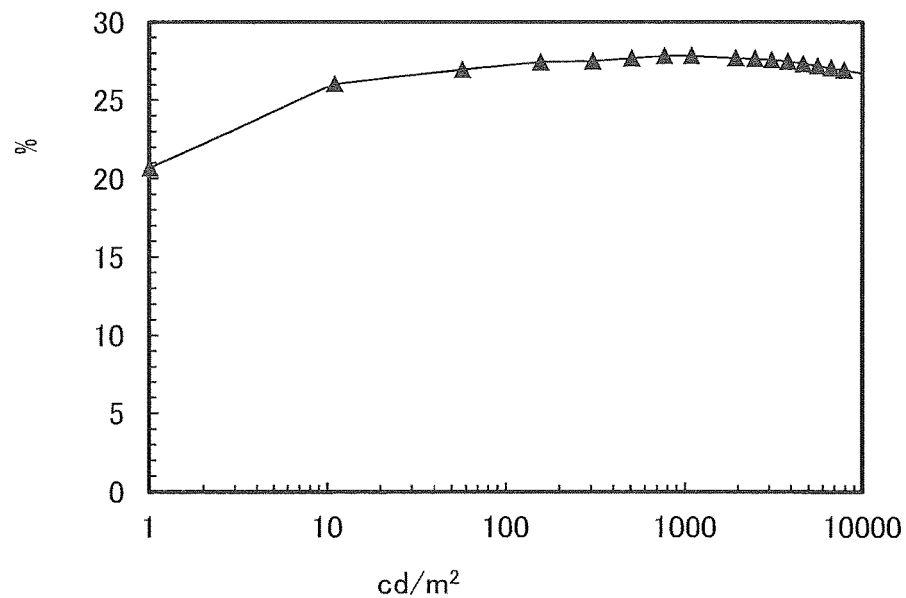
FIG. 41 shows luminance-external quantum efficiency characteristics of a light-emitting element 4.
Figure 42:
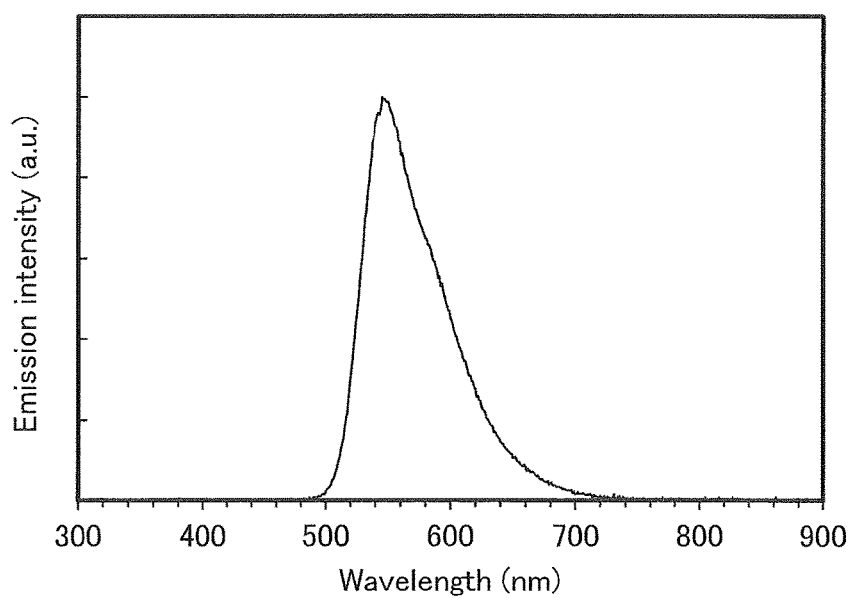
FIG. 42 shows an emission spectrum of a light-emitting element 4.

FIG. 37 shows current density-luminance characteristics of the light-emitting element 4; FIG. 38 shows luminance-current efficiency characteristics thereof; FIG. 39 shows voltage-luminance characteristics thereof; FIG. 40 shows luminance-power efficiency characteristics thereof; FIG. 41 shows luminance-external quantum efficiency characteristics thereof; and FIG. 42 shows an emission spectrum thereof.

Table 4 shows values of major characteristics of the light-emitting element 4 at approximately 1000 cd/m².

TABLE 4

| | Voltage (V) | Current (mA) | Current Density (mA/cm²) | Chromaticity x | Chromaticity y | Current Efficiency (cd/A) | Power Efficiency (lm/W) | External Quantum Efficiency (%) |
|---|---|---|---|---|---|---|---|---|
| Light-emitting Element 4 | 3.1 | 0.04 | 1.1 | 0.42 | 0.56 | 103 | 104 | 28 |

The above results show that the light-emitting element 4 using ThBBiF, which is the organic compound described in Embodiment 1, has extremely favorable characteristics also when a light-emitting substance emitting yellowish green phosphorescence is used as an emission center substance.

In particular, the external quantum efficiency was excellent; the value was kept high even in a high-luminance region. Besides, the drive voltage was low, and as a result, an extremely high power efficiency of 120 lm/W or more was achieved.

Figure 43:
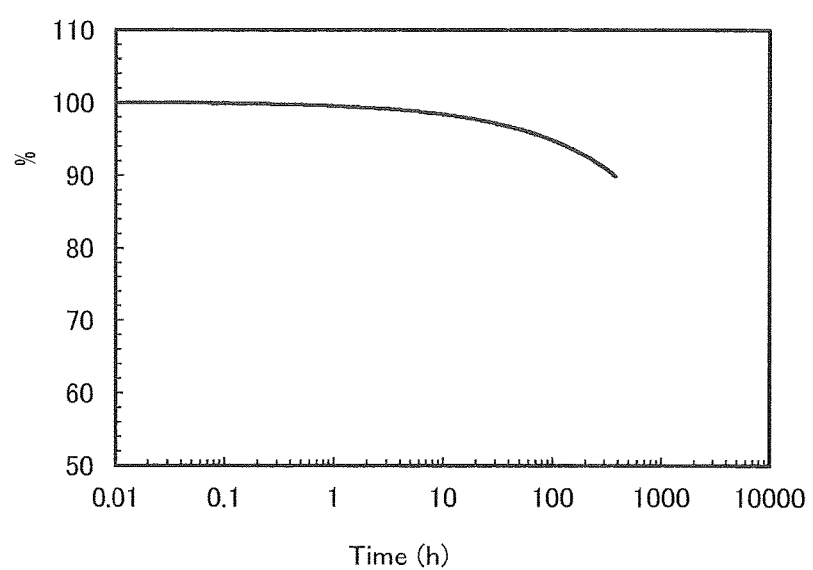
FIG. 43 shows time dependence of normalized luminance of a light-emitting element 4.

A reliability test was carried out, and the results thereof are shown in FIG. 43. In the reliability test, the light-emitting element 4 was driven under the conditions where the initial luminance was set to 5000 cd/m² and the current density was constant. FIG. 43 shows a change in normalized luminance where the initial luminance is 100%. The results show that a decrease in luminance over driving time of the light-emitting element 4 is small, and thus the light-emitting element 4 has favorable reliability.

Example 7

In this example, the light-emitting element (a light-emitting element 5) described in Embodiment 2 will be described. Note that in the light-emitting element 5, N-(1,1'-biphenyl-4-yl)-N-[4-(dibenzothiophen-4-yl)phenyl]-9,9-dimethyl-9H-fluoren-2-amine (abbreviation: ThBBiF), which is the organic compound described in Embodiment 1, was used as the second organic compound in the light-emitting layer 113, and 4,6-bis[3-(9H-carbazol-9-yl)phenyl]pyrimidine (abbreviation: 4,6mCzP2Pm) was used as the first organic compound. Chemical formulae of materials used in this example are shown below.

(i)

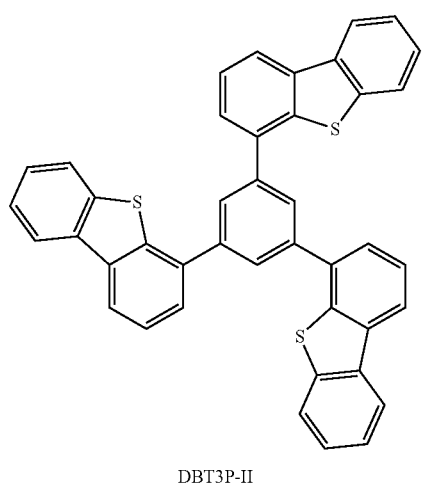

DBT3P-II (ii)

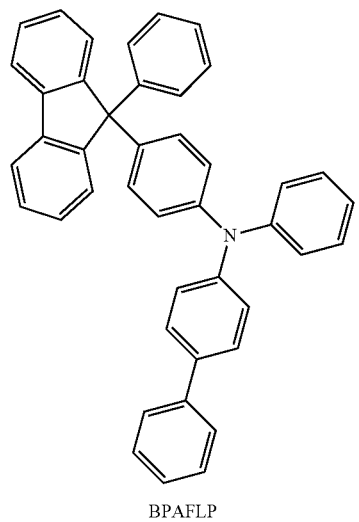

BPAFLP

-continued (iii)

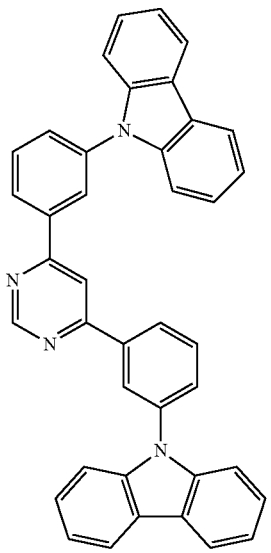

4,6mCzP2Pm (200)

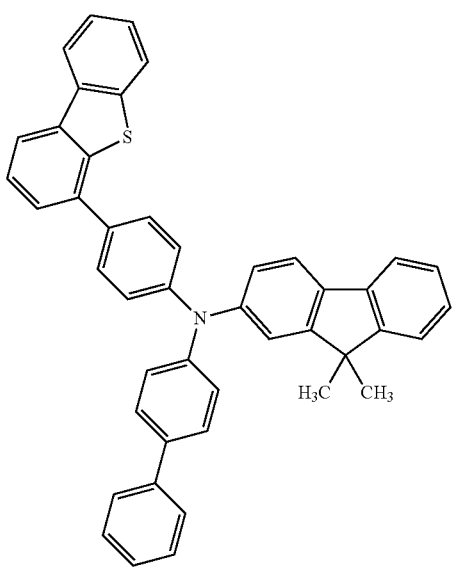

ThBBiF (iv)

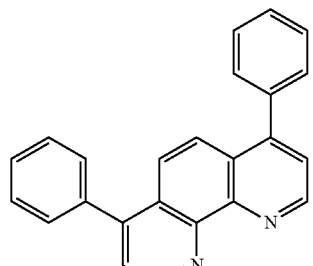

BPhen (Method for Fabricating Light-Emitting Element 5)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to approximately $10^{-4}$ Pa. After that, over the first electrode 101, 4,4',4"-(benzene-1,3,5-triyl)tri(dibenzothiophene) (abbreviation: DBT3P-II) represented by Structural Formula (i) and molybdenum(VI) oxide were deposited by co-evaporation by an evaporation method using resistance heating, so that the hole-injection layer 111 was formed. The thickness of the hole-injection layer 111 was set to 20 nm, and the weight ratio of DBT3P-II to molybdenum oxide was adjusted to 4:2. Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) which is represented by Structural Formula (ii) was formed to a thickness of 20 nm over the hole-injection layer 111 to form the hole-transport layer 112.

Further, over the hole-transport layer 112, 4,6-bis[3-(9H-carbazol-9-yl)phenyl]pyrimidine (abbreviation: 4,6mCzP2Pm) represented by Structural Formula (iii) and N-(1,1'-biphenyl-4-yl)-N-[4-(dibenzothiophen-4-yl)phenyl]-9,9-dimethyl-9H-fluoren-2-amine (abbreviation: ThBBiF) represented by Structural Formula (200) were deposited by co-evaporation to a thickness of 40 nm such that the weight ratio of 4,6mCzP2Pm to ThBBiF was 0.8:0.2, whereby the light-emitting layer 113 was formed.

Then, the electron-transport layer 114 was formed over the light-emitting layer 113 in such a way that a 20 nm thick film of 4,6mCzP2Pm was formed and a 10 nm thick film of bathophenanthroline (abbreviation: BPhen) represented by Structural Formula (iv) was formed.

After the formation of the electron-transport layer 114, lithium fluoride (LiF) was deposited by evaporation to a thickness of 1 run, so that the electron-injection layer 115 was formed. Lastly, aluminum was deposited by evaporation to a thickness of 200 nm to form the second electrode 102 functioning as a cathode. Thus, the light-emitting element 5 in this example was fabricated.

Note that in all the above evaporation steps, evaporation was performed by a resistance-heating method.

The light-emitting element 5 was sealed using a glass substrate in a glove box containing a nitrogen atmosphere so as not to be exposed to the air (specifically, a sealing material was applied onto an outer edge of the element and heat treatment was performed at 80° C. for 1 hour at the time of sealing). Then, initial characteristics of the light-emitting element were measured. Note that the measurement was carried out at room temperature (in an atmosphere kept at 25° C.).

Figure 44:
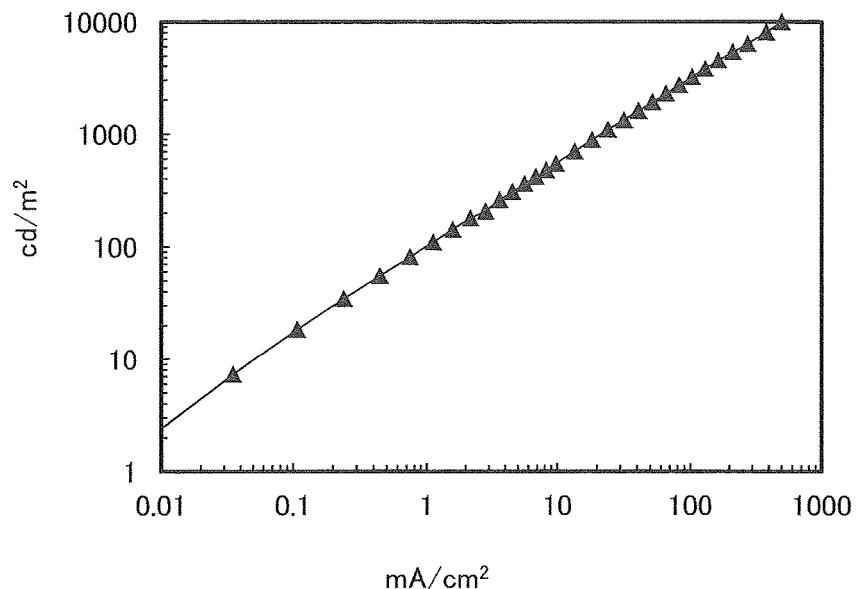
FIG. 44 shows current density-luminance characteristics of a light-emitting element 5.
Figure 45:
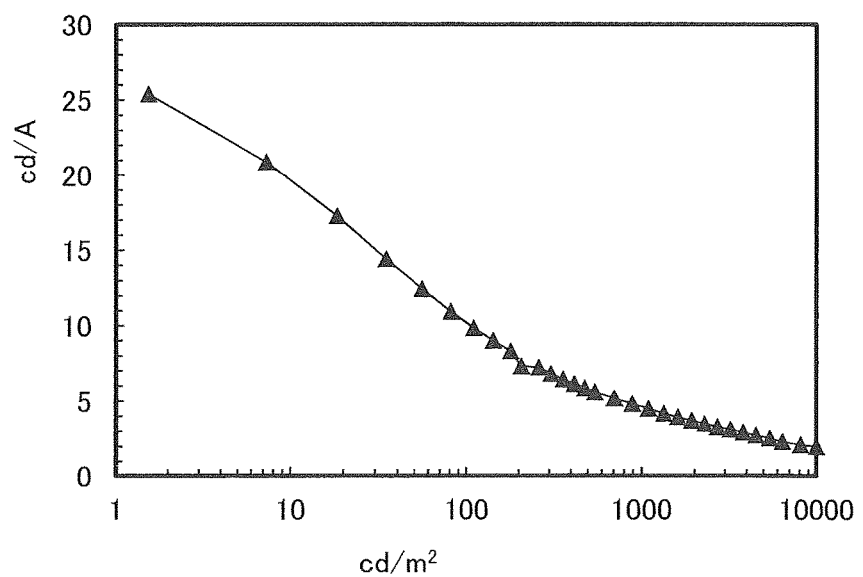
FIG. 45 shows luminance-current efficiency characteristics of a light-emitting element 5.
Figure 46:
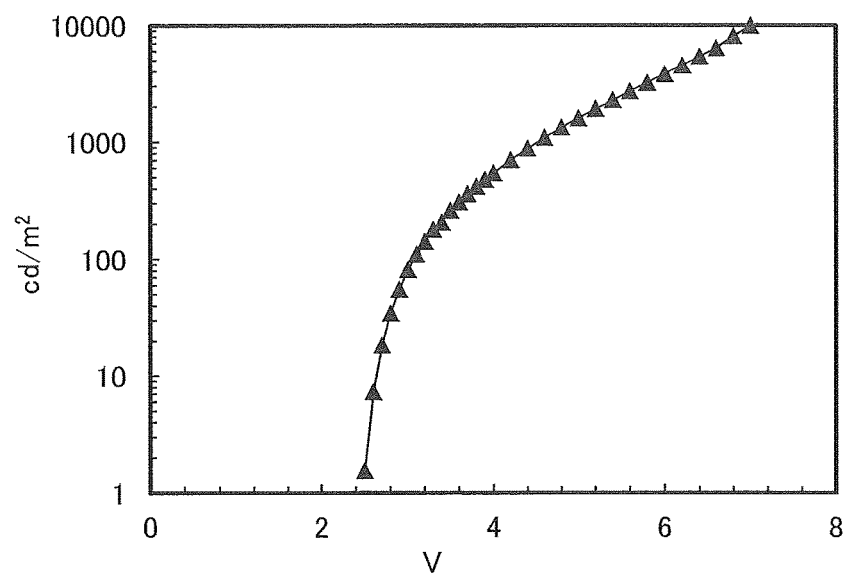
FIG. 46 shows voltage-luminance characteristics of a light-emitting element 5.
Figure 47:
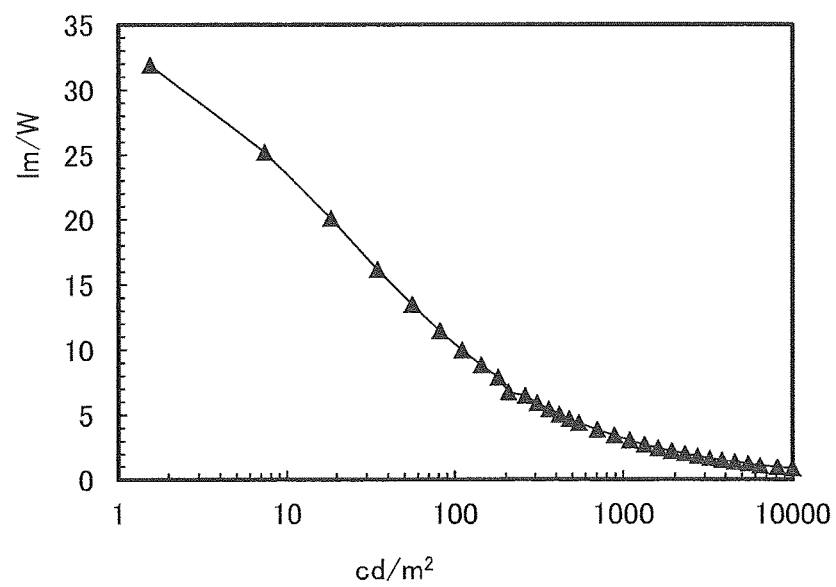
FIG. 47 shows luminance-power efficiency characteristics of a light-emitting element 5.
Figure 48:
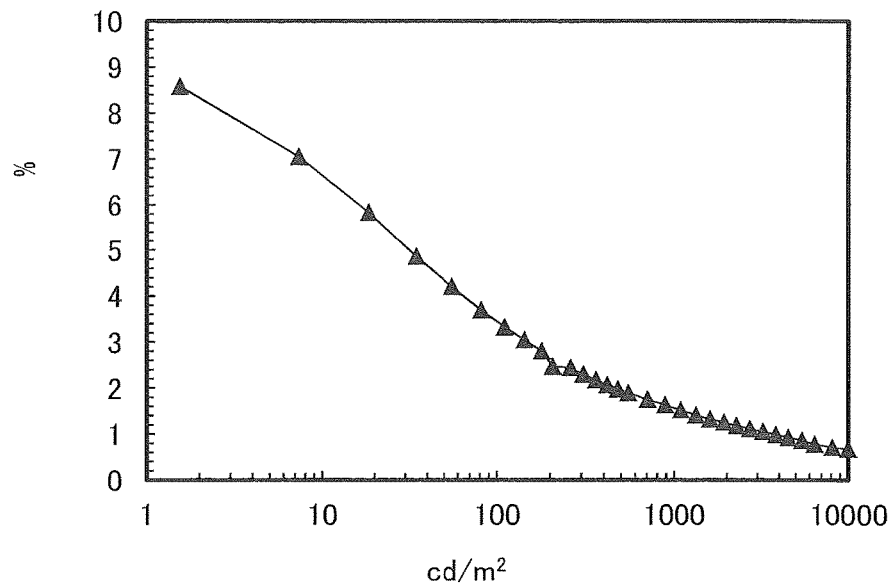
FIG. 48 shows luminance-external quantum efficiency characteristics of a light-emitting element 5.
Figure 49:
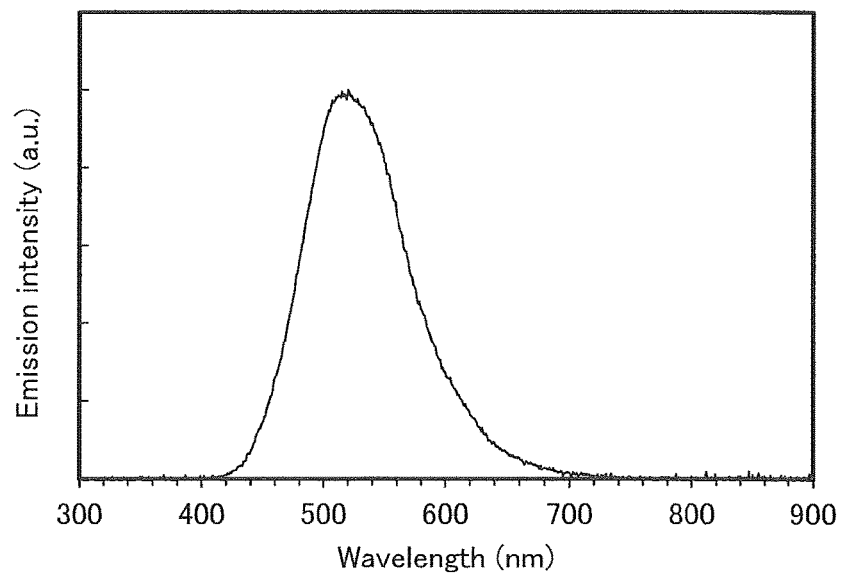
FIG. 49 shows an emission spectrum of a light-emitting element 5.

FIG. 44 shows current density-luminance characteristics of the light-emitting element 5; FIG. 45 shows luminance-current efficiency characteristics thereof; FIG. 46 shows voltage-luminance characteristics thereof; FIG. 47 shows luminance-power efficiency characteristics thereof; FIG. 48 shows luminance-external quantum efficiency characteristics thereof; and FIG. 49 shows emission spectra thereof.

Table 5 shows values of major characteristics of the light-emitting element 5 at approximately 1000 cd/m².

TABLE 5

|  | Voltage (V) | Current (mA) | Current Density (mA/cm²) | Chromaticity x | Chromaticity y | Current Efficiency (cd/A) | Power Efficiency (lm/W) | External Quantum Efficiency (%) |
|---|---|---|---|---|---|---|---|---|
| Light-emitting Element 5 | 4.6 | 0.97 | 24.2 | 0.25 | 0.46 | 4.5 | 3.1 | 1.5 |

The above results show that the light-emitting element 5 using ThBBiF, which is the organic compound described in Embodiment 1, has favorable characteristics. Specifically, according to FIG. 48 showing the external quantum efficiency, the light-emitting element 5 has an efficiency far exceeding 5% in a low-luminance region. It is said that the extraction efficiency of a light-emitting element like the light-emitting element in this example which is not designed to enhance extraction efficiency is approximately 20% to 30%. The theoretical limit of the internal quantum efficiency of fluorescence, which is based on the generation ratio of singlet excitons generated by current excitation, is 25%. Thus, the theoretical limit of the external quantum efficiency of a fluorescent light-emitting element is calculated to be 5% to 7.5%. It can be found that the external quantum efficiency of the light-emitting element 5 in a low-luminance region exceeds the theoretical limit.

The above results suggest that an exciplex formed by the first organic compound and the second organic compound (4,6mCzP2Pm and ThBBiF) emits light with high efficiency and that the light includes delayed fluorescence components. The light-emitting element 5 was able to emit light with high emission efficiency owing to delayed fluorescence that occurred efficiently via reverse intersystem crossing from a triplet excited state to a singlet excited state.

REFERENCE NUMERALS

101: first electrode, 102: second electrode, 103: layer containing an organic compound, 111: hole-injection layer, 112: hole-transport layer, 113: light-emitting layer, 114: electron-transport layer, 115: electron-injection layer, 400: substrate, 401: first electrode, 403: layer containing an organic compound, 404: second electrode, 405: sealing material, 407: sealing substrate, 412: pad, 420: IC chip, 501: first electrode, 502: second electrode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealing material, 607: space, 608: wiring, 609: FPC (flexible printed circuit), 610: element substrate, 611: switching TFT, 612: current controlling TFT, 613: first electrode, 614: insulator, 616: layer containing an organic compound, 617: second electrode, 618: light-emitting element, 623: n-channel TFT, 624: p-channel TFT, 625: desiccant, 901: housing, 902: liquid crystal layer, 903: backlight unit, 904: housing, 905: driver IC, 906: terminal, 951: substrate, 952: electrode, 953: insulating layer, 954: partition layer, 955: layer containing an organic compound, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode of a light-emitting element, 1024R: first electrode of a light-emitting element, 1024G: first electrode of a light-emitting element, 1024B: first electrode of a light-emitting element, 1025: partition, 1028: layer containing an organic compound, 1029: second electrode of a light-emitting element, 1031: sealing substrate, 1032: sealing material, 1033: transparent base material, 1034R: red coloring layer, 1034G: green coloring layer, 1034B: blue coloring layer, 1035: black layer (black matrix), 1036: overcoat layer, 1037: third interlayer insulating film, 1040: pixel portion, 1041: driver circuit portion, 1042: peripheral portion, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone, 9033: clasp, 9034: switch, 9035: power switch, 9036: power saver switch, 9038: operation switch, 9630: housing, 9631: display portion, 9631a: display portion, 9631b: display portion, 9632a: touchscreen region, 9632b: touchscreen region, 9633: solar cell, 9634: charge and discharge control circuit, 9635: battery, 9636: DC-to-DC converter, 9637: operation key, 9638: converter, and 9639: button.

This application is based on Japanese Patent Application serial no. 2013-064278 filed with Japan Patent Office on Mar. 26, 2013, the entire contents of which are hereby incorporated by reference.

What is claimed is:

1. A host material for a light-emitting substance, the host material comprising:
an organic compound represented by a formula (G1):

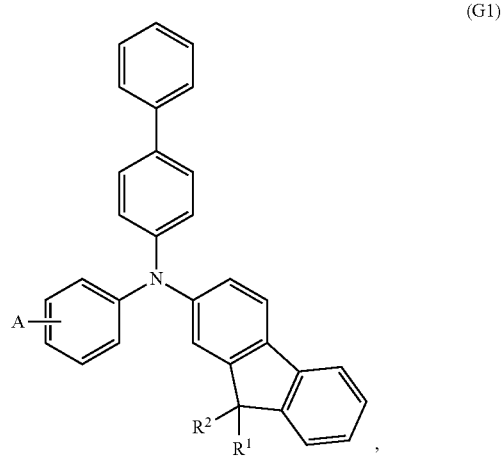

(G1)

wherein:
A represents one of a dibenzofuranyl group and a dibenzothiophenyl group; and
$R^1$ and $R^2$ each separately represents an alkyl group having 1 to 6 carbon atoms, and
wherein the host material is configured to provide excitation energy of the host material to the light-emitting substance.

2. The host material according to claim 1, wherein the organic compound is represented by a formula (G2):

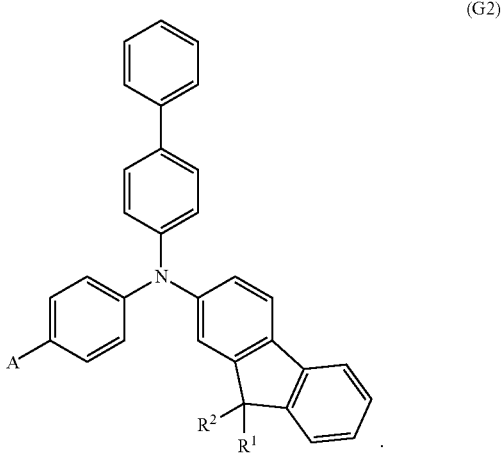

(G2)

3. The host material according to claim 1, wherein A represents one of groups represented by formulae (A-1) to (A-4):

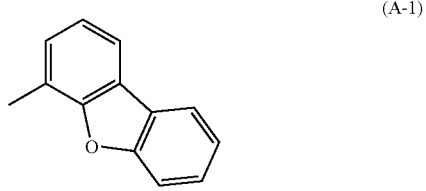

(A-1)

-continued (A-2)
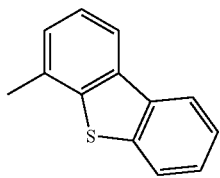

(A-3)
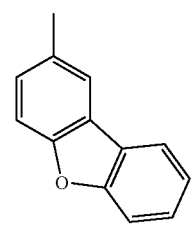

(A-4)
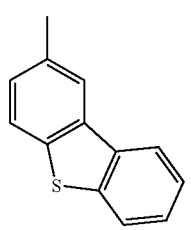

4. The host material according to claim 1, wherein A represents a group represented by a formula (A-1) or (A-2):

(A-1)
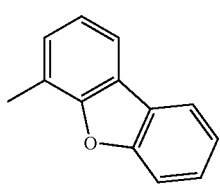

(A-2)
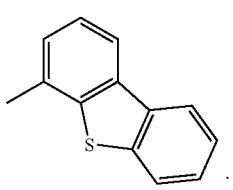

5. The host material according to claim 1, wherein A represents a group represented by a formula (A-1):

(A-1)
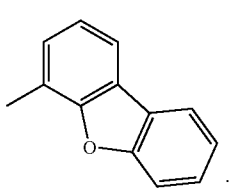

6. The host material according to claim 1, wherein $R^1$ and $R^2$ each separately represent one of groups represented by formulae (R-1) to (R-12):

(R-1)

(R-2)

(R-3)

(R-4)

(R-5)

(R-6)

(R-7)

(R-8)

(R-9)

(R-10)

(R-11)

(R-12)

7. The host material according to claim 1, wherein both $R^1$ and $R^2$ are methyl groups.

8. The host material according to claim 1, wherein the organic compound is represented by a formula (100):

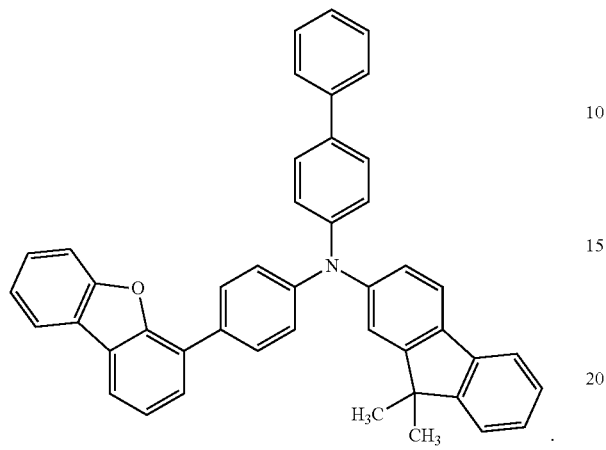

(100)

9. The host material according to claim 1, wherein the light-emitting substance is a phosphorescent substance.

10. The host material according to claim 1,
wherein the host material is a mixture comprising the organic compound and a first compound, and
wherein the first compound has an electron transport property.

11. The host material according to claim 1,
wherein the host material is a mixture comprising the organic compound and a first compound, and
wherein the first compound is a nitrogen-containing heteroaromatic compound.

12. A method for use of the host material according to claim 1, comprising the step of:
co-evaporating the organic compound and the light-emitting substance.

13. A host material for a light-emitting substance, the host material comprising:
an organic compound represented by a formula (G1):

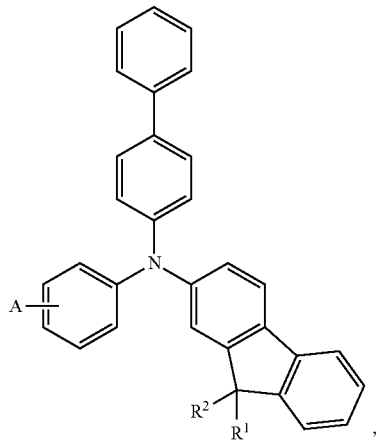

(G1)

wherein:
A represents one of a dibenzofuranyl group and a dibenzothiophenyl group;
$R^1$ and $R^2$ each separately represent an alkyl group having 1 to 6 carbon atoms; and
the organic compound is capable of forming an exciplex with a nitrogen-containing heteroaromatic compound, and
wherein the exciplex is configured to provide excitation energy of the host material to the light-emitting substance.

14. The host material according to claim 13, wherein the organic compound is represented by a formula (G2):

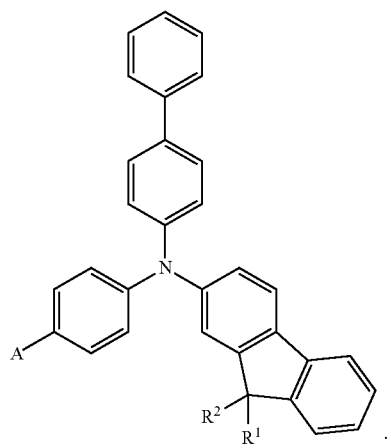

(G2)

15. The host material according to claim 13, wherein A represents one of groups represented by formulae (A-1) to (A-4):

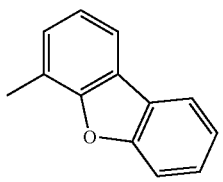

(A-1)

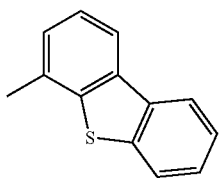

(A-2)

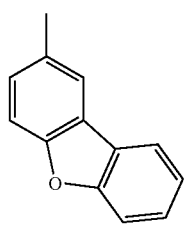

(A-3)

-continued
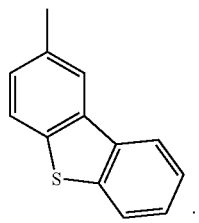
(A-4)
16. The host material according to claim 13,
wherein the organic compound is capable to form an exciplex by a first compound,
wherein a HOMO level of the first compound is deeper than a HOMO level of the organic compound, and
wherein a LUMO level of the first compound is deeper than a LUMO level of the organic compound.
* * * * *